United States Patent
Katzenellenbogen et al.

(10) Patent No.: US 11,673,866 B2
(45) Date of Patent: Jun. 13, 2023

(54) ESTROGEN RECEPTOR BETA LIGANDS FOR THE PREVENTION AND TREATMENT OF MULTIPLE SCLEROSIS (MS) AND OTHER DEMYELINATING, INFLAMMATORY AND NEURODEGENERATIVE DISEASES

(71) Applicants: The Board of Trustees of the University of Illinois, Urbana, IL (US); The Regents of the University of California, Oakland, CA (US)

(72) Inventors: John A. Katzenellenbogen, Urbana, IL (US); Seema K. Tiwari-Woodruff, Riverside, CA (US); Sung Hoon Kim, Champaign, IL (US); Benita Katzenellenbogen, Urbana, IL (US)

(73) Assignees: The Board of Trustees of the University of Illinois, Urbana, IL (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 17/054,878

(22) PCT Filed: May 23, 2019

(86) PCT No.: PCT/US2019/033824
§ 371 (c)(1),
(2) Date: Nov. 12, 2020

(87) PCT Pub. No.: WO2019/226936
PCT Pub. Date: Nov. 28, 2019

(65) Prior Publication Data
US 2021/0230121 A1    Jul. 29, 2021

Related U.S. Application Data

(60) Provisional application No. 62/675,508, filed on May 23, 2018.

(51) Int. Cl.
| | | |
|---|---|---|
| *C07D 231/56* | (2006.01) | |
| *C07D 409/04* | (2006.01) | |
| *C07D 409/10* | (2006.01) | |
| *A61P 25/28* | (2006.01) | |

(52) U.S. Cl.
CPC ............ *C07D 231/56* (2013.01); *A61P 25/28* (2018.01); *C07D 409/04* (2013.01); *C07D 409/10* (2013.01)

(58) Field of Classification Search
CPC ................ C07D 231/56; C07D 409/04; C07D 409/10
See application file for complete search history.

(56) References Cited

U.S. PATENT DOCUMENTS

| | | |
|---|---|---|
| 7,960,563 B2 | 6/2011 | Johnson et al. |
| 2004/0102435 A1 | 5/2004 | Barlaam et al. |
| 2004/0167127 A1 | 8/2004 | Steffan et al. |
| 2011/0112142 A1 | 5/2011 | Noteberg et al. |

FOREIGN PATENT DOCUMENTS

| | | |
|---|---|---|
| WO | WO03051860 A2 | 6/2003 |
| WO | WO2010030787 A1 | 3/2010 |

OTHER PUBLICATIONS

De Angelis et al. J. Med. Chem. 2005, 48, 1132-1144 (Year: 2005).*
European Patent Office Partial Search Report for Application No. 19808511.0 dated Oct. 7, 2021 (19 pages).
Schopfer et al., "Toward Selective ERbeta agonists for central nervous system disorders: synthesis and characterization of aryl benzthiophenes", J. Med. Chem., 2002, vol. 45, pp. 1399-1401.
European Patent Office Extended Search Report for Application No. 19808511.0 dated Jan. 14, 2022 (16 pages).
Banks et al., "Invited Commentary: Hormone therapy risks and benefits—The Women's Health Initiative findings and the postmenopausal estrogen timing hypothesis", Am J Epidemiol, vol. 170, No. 1, 2009, pp. 24-28.
Barun et al., "Treatment of multiple sclerosis with anti-CD20 antibodies", Clin Immunol, 2012, vol. 142, pp. 31-37.
Beringer et al., "IL-17 in Chronic Inflammation: From Discovery to Targeting", Trends Mol Med, 2016, vol. 22, pp. 230-241.
Burns et al., "Estrogen receptors and human disease: an update", Arch Toxicol, 2012, vol. 86, pp. 1491-1504.
Crawford et al., "Assaying the functional effects of demyelination and remyelination: revisiting field potential recordings", J Neurosci Methods, 2009, vol. 182, pp. 25-33.
Crawford et al., "Functional recovery of callosal axons following demyelination: a critical window", Neuroscience, vol. 164, 2009, pp. 1407-1421.
Crawford et al., "Oestrogen receptor beta ligand: a novel treatment to enhance endogenous functional remyelination", Brain, vol. 133, 2010, pp. 2999-3016.
Cua et al., "Self-antigen-induced Th2 responses in experimental allergic encephalomyelitis (EAE)-resistant mice. Th2-mediated suppression of autoimmune disease", J Immunol, vol. 155, 1995, pp. 4052-4059.
De Filippo et al., "Neutrophil chemokines KC and macrophage-inflammatory protein-2 are newly synthesized by tissue macrophages using distinct TLR signaling pathways", Journal of Immunology, 2008, vol. 180, pp. 4308-4315.
De Waal et al., "Effects of IL-13 on phenotype, cytokine production, and cytotoxic function of human monocytes. Comparison with IL-4 and modulation by IFN-gamma or IL-10", J Immunol, vol. 151, No. 11, 1993, pp. 6370-6381.

(Continued)

*Primary Examiner* — Matthew P Coughlin
(74) *Attorney, Agent, or Firm* — Michael Best & Friedrich LLP

(57) ABSTRACT

4-Hydroxyphenyl-2H-indazol-5-ol compounds are estrogen receptor beta ligands that have immunomodulatory properties and increase oligodendrocyte survival, differentiation, and remyelination. The compounds, compositions, and kits are useful in the treatment of multiple sclerosis and endometriosis.

27 Claims, 30 Drawing Sheets

(56) References Cited

OTHER PUBLICATIONS

Denic et al., "The relevance of animal models in multiple sclerosis research", Pathophysiology, vol. 18, 2011, pp. 21-29.
Du et al., "Estrogen receptor-beta ligand treatment modulates dendritic cells in the target organ during autoimmune demyelinating disease", Eur J Immunol, 2011, vol. 41, pp. 140-150.
Filipovic et al., "The effect of CXCL1 on human fetal oligodendrocyte progenitor cells", Glia, vol. 56, 2008, pp. 1-15.
Fletcher et al., "T cells in multiple sclerosis and experimental autoimmune encephalomyelitis", Clin Exp Immunol, 2010, vol. 162, pp. 1-11.
Hasselmann et al., "Consistent induction of chronic experimental autoimmune encephalomyelitis in C57BL/6 mice for the longitudinal study of pathology and repair", J Neurosci Methods, vol. 284, 2017, pp. 71-84.
Hewitt et al., "Oestrogen receptor knockout mice: roles for oestrogen receptors alpha and beta in reproductive tissues", Reproduction, vol. 125, 2003, pp. 143-149.
Inoue et al., "An interferon-beta-resistant and NLRP3 inflammasome-independent subtype of EAE with neuronal damage", Nat Neurosci, vol. 19, No. 12, 2016, pp. 1599-1609.
Jansson et al., "Estrogen-mediated immunosuppression in autoimmune diseases", Inflamm Res, vol. 47, 1998, pp. 290-301.
Khalaj, "Nudging oligodendrocyte intrinsic signaling to remyelinate and repair: Estrogen receptor ligand effects", The Journal of Steroid Biochem. and Mol. Biol., vol. 160, 2016, pp. 43-52.
Khalaj et al., "Estrogen receptor (ER) beta expression in oligodendrocytes is required for attenuation of clinical disease by an ERbeta ligand", PNAS, vol. 110, 2013, pp. 19125-19130.
Kim et al., "Estriol ameliorates autoimmune demyelinating disease: implications for multiple sclerosis", Neurology, vol. 52, No. 6, 1999, pp. 1230-1238.
Kumar et al., "Estrogen receptor beta ligand therapy activates PI3K/Akt/mTOR signaling in oligodendrocytes and promotes remyelination in a mouse model of multiple sclerosis", Neurobiol Dis, vol. 56, 2013, pp. 131-144.
Lauderdale et al., "Osmotic Edema Rapidbly Increases Neuronal Excitability Through Activation of NMDA Receptor-Dependent Slow Inward Currents in Juvenile and Adult Hippocampus", 2015, ASN Neuro, pp. 1-21.
Luchtman et al., "IL-17 and related cytokines involved in the pathology and immunotherapy of multiple sclerosis: Current and future developments", Cytokine Growth Factor Rev, vol. 25, 2014, pp. 403-413.
Mangiardi et al., "An animal model of cortical and callosal pathology in multiple sclerosis", Brain Pathol, vol. 21, 2011, pp. 263-278.
Minutolo et al., "Estrogen receptor beta ligands: recent advances and biomedical applications", Med Res Rev, vol. 31, No. 3, 2011, pp. 364-442.
Monnerie et al., "Reduced sterol regulatory element-binding protein (SREBP) processing through site-1 protease (S1P) inhibition alters oligodendrocyte differentiation in vitro", J Neurochem, vol. 140, 2017, pp. 53-67.
Moore et al., "Therapeutic laquinimod treatment decreases inflammation, initiates axon remyelination, and improves motor deficit in a mouse model of multiple sclerosis", Brain Behav, vol. 3, No. 6, 2013, pp. 664-682.
Moore et al., "Multiple functional therapeutic effects of the estrogen receptor beta agonist indazole-CI in a mouse model of multiple sclerosis", Proc Natl Acad Sci, vol. 111, No. 50, 2014, pp. 18061-18066.
Moss et al., "Th1/Th2 cells in inflammatory disease states: therapeutic implications", Expert Opin Biol Ther, vol. 4, 2004, pp. 1887-1896.
Nicot, "Gender and sex hormones in multiple sclerosis pathology and therapy", Front Biosci, vol. 14, 2009, pp. 4477-4515.
Omari et al., "Role for CXCR2 and CXCL1 on glia in multiple sclerosis", Glia, vol. 53, 2006, pp. 24-31.
Omari et al., "Neuroprotection and remyelination after autoimmune demyelination in mice that inducibly overexpress CXCL1", Am J Pathol, vol. 174, 2009, pp. 164-176.
Ouyang et al., "Regulation and functions of the IL-10 family of cytokines in inflammation and disease", Annu Rev Immunol, vol. 29, 2011, pp. 71-109.
Ozturk et al., "MRI of the corpus callosum in multiple sclerosis: association with disability", Mult Scler, vol. 16, No. 2, 2010, pp. 166-177.
Paterni et al., "Estrogen receptors alpha (ERalpha) and beta (ERbeta): subtype-selective ligands and clinical potential", Steroids, vol. 90, 2014, pp. 13-29.
Pettinelli et al., "Adoptive transfer of experimental allergic encephalomyelitis in SJL/J mice after in vitro activation of lymph node cells by myelin basic protein: requirement for Lyt 1+ 2-lymphocytes", Journal of immunology, vol. 127, 1981, pp. 1420-1423.
Popko et al., "Oligodendroglial response to the immune cytokine interferon gamma", Neurochem Res, vol. 24, No. 2, 1999, pp. 331-338.
Preston et al., "Effects of 4-aminopyridine on rapidly and slowly conducting axons of rat corpus callosum", Exp Neurol, vol. 79, 1983, pp. 808-820.
Robinson et al., "The chemokine growth-regulated oncogene-alpha promotes spinal cord oligodendrocyte precursor proliferation", J Neurosci, vol. 18, 1998, pp. 10457-10463.
Rossi et al., "Potential role of IL-13 in neuroprotection and cortical excitability regulation in multiple sclerosis", Mult Scler, vol. 17, 2011, pp. 1301-1312.
Saijo et al., "An ADIOL-ERbeta-CtBP transrepression pathway negatively regulates microglia-mediated inflammation", Cell, vol. 145, 2011, pp. 584-595.
Sinha et al., "IL-13-mediated gender difference in susceptibility to autoimmune encephalomyelitis", J Immunol, vol. 180, 2008, pp. 2679-2685.
Sospedra et al., "Immunology of multiple sclerosis", Annu Rev Immunol, vol. 23, 2005, pp. 683-747.
Tirotta et al., "CXCR2 signaling protects oligodendrocyte progenitor cells from IFN-gamma/CXCL10-mediated apoptosis", Glia, vol. 59, 2011, pp. 1518-1528.
Tiwari-Woodruff et al., "Differential neuroprotective and antiinflammatory effects of estrogen receptor (ER)alpha and ERbeta ligand treatment", Proc Natl Acad Sci, vol. 104, 2007, pp. 14813-14818.
Tiwari-Woodruff et al., "K+ channel KV3.1 associates with OSP/claudin-11 and regulates oligodendrocyte development", Am J Physiol Cell Physiol, vol. 291, 2006, pp. C687-C698.
Tiwari-Woodruff et al., "OSP/claudin-11 forms a complex with a novel member of the tetraspanin super family and beta1 integrin and regulates proliferation and migration of oligodendrocytes", J. Cell Biol, vol. 153, No. 2, 2001, pp. 295-305.
Tiwari-Woodruff et al., "Treatment with an Estrogen Receptor alpha-Ligand is Neuroprotective in Experimental Autoimmune Encephalomyelitis," The Journal of Neuroscience, vol. 26, No. 25, 2006, pp. 6823-6833.
Tiward-Woodruff et al., "Functional recovery of callosal axons following demyelination a critical window", Neuroscience, vol. 146, 2009, pp. 1407-1421.
Tsai et al., "The chemokine receptor CXCR2 controls positioning of oligodendrocyte precursors in developing spinal cord by arresting their migration", Cell, vol. 110, 2002, pp. 373-383.
Vartanian et al., "Interferon-gamma-induced oligodendrocyte cell death: implications for the pathogenesis of multiple sclerosis", Mol Med, vol. 1, No. 7, 1995, pp. 732-743.
Xue et al., "Estrogen regulation of the brain renin-angiotensin system in protection against angiotensin II-induced sensitization of hypertension", Am J Physiol Heart Circ Physiol, vol. 307, 2014, pp. H191-H198.
Zorzella-Pezavento et al., "Persistent inflammation in the CNS during chronic EAE despire local absence of IL-17 production", Mediators Inflamm., 2013, pp. 1-10.
International Search Report and Written Opinion for Application No. PCT/US19/033824 dated Sep. 24, 2019 (18 pages).
International Preliminary Report on Patentability for Application No. PCT/US19/033824 dated Nov. 24, 2019 (7 pages).

(56) References Cited

OTHER PUBLICATIONS

De Angelis et al., "Indazole Estrogens: Highly Selective Ligands for the Estrogen Receptor β", J. Med. Chem., vol. 48, 2005, pp. 1132-1144.
Karim et al., "An increase in chemokine CXCL1 by ERβ ligand treatment is a key mediator in promoting axon remyelination", Proc. Natl. Acad. Sci., 2018, vol. 115, No. 24, pp. 6291-6296.
Zhao et al., "Dual suppression of estrogenic and inflammatory activities for targeting of endometriosis", Science Translational Medicine, vol. 7, No. 271, 2015, 14 pages.
Jundt, J. W., et al. "A comparison of low dose methotrexate bioavailability: oral solution, oral tablet, subcutaneous and intramuscular dosing." The Journal of Rheumatology 20.11 (1993): 1845-1849.
Karim, H., et al. "Analogues of ERβ ligand chloroindazole exert immunomodulatory and remyelinating effects in a mouse model of multiple sclerosis." Scientific reports 9.1 (2019): 1-17.
Milovanovic, J., et al. "Interleukin-17 in chronic inflammatory neurological diseases." Frontiers in immunology 11 (2020): 947.
Nassar, A.-E. F., et al. "Improving the decision-making process in the structural modification of drug candidates: enhancing metabolic stability." Drug discovery today 9.23 (2004): 1020-1028.

\* cited by examiner

| Name | R (2') [X = H except where noted] | RBA[a] ERβ | ERα | β/α Ratio |
|---|---|---|---|---|
| IndCl | H | 32.1 ± 9.0 | 0.30 ± 0.03 | 107 |
| IndCl-o-Br | Br | 8.31 | 0.465 | 17.9 |
| IndCl-o-Cl | Cl | 10.9 | 0.404 | 27.0 |
| IndCl-o-Me | Me | 21.1 | 0.431 | 49.0 |
| IndCl-o-I | I | 5.38 | 0.343 | 15.7 |
| IndCl-o-F | F | 9.79 | 0.187 | 52.4 |
| IndCl-o-Cl-4-Cl | Cl [X = Cl] | 0.73 | 0.334 | 2.2 |
| IndCl-o-CF$_3$ | CF$_3$ | 10.4 | 2.84 | 3.7 |

[a] RBA is relative binding affinity, where estradiol (E2) is 100.

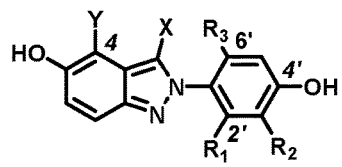

| Name | $R_1$ | $R_2$ | $R_3$ | X | Y | RBA[a] ERα | RBA[a] ERβ | β/α Ratio | %MBP+/DAPI[b] |
|---|---|---|---|---|---|---|---|---|---|
| IndCl-o-Br | Br | H | H | Cl | H | 0.47 | 8.31 | 17.9 | * |
| IndCl-o-Cl | Cl | H | H | Cl | H | 0.40 | 10.9 | 27.1 | ***** |
| IndCl-o-Me | Me | H | H | Cl | H | 0.43 | 21.1 | 48.9 | ***** |
| IndCl-o-I | I | H | H | Cl | H | 0.34 | 5.38 | 15.7 | **** |
| IndCl-o-F | F | H | H | Cl | H | 0.19 | 9.79 | 52.4 | **** |
| IndCl-o-CN | CN | H | H | Cl | H | 0.05 | 0.77 | 15.7 | --- |
| IndCl-o-Cl-4-Cl | Cl | H | H | Cl | Cl | 0.33 | 0.73 | 0.46 | * |
| IndCl-o-F2-4-Cl | F | H | F | Cl | Cl | 0.076 | 0.28 | 3.6 | *** |
| IndCl-o-Cl2-4-Cl | Cl | H | Cl | Cl | Cl | 0.11 | 2.3 | 21.1 | *** |
| IndCl-o-CF3 | CF$_3$ | H | H | Cl | H | 2.84 | 10.39 | 3.7 | - |
| IndCl-o-OH | OH | H | H | Cl | H | 0.062 | 2.99 | 48.2 | **** |
| IndCl-m-F | H | F | H | Cl | H | 0.14 | 10.5 | 75.7 | ** |
| IndCl-m-Me | H | Me | H | Cl | H | 0.13 | 0.74 | 5.8 | - |
| IndF-o-Br | Br | H | H | F | H | 0.37 | 1.22 | 3.3 | |
| IndF-o-Cl | Cl | H | H | F | H | 0.79 | 59.10 | 74.8 | |
| IndF-o-Me | Me | H | H | F | H | 0.11 | 0.37 | 3.4 | |
| IndF-o-I | I | H | H | F | H | 1.05 | 4.39 | 4.2 | |
| IndBr-o-Br | Br | H | H | Br | H | 1.40 | 5.84 | 4.2 | |
| IndBr-o-Cl | Cl | H | H | Br | H | 0.81 | 16.12 | 19.9 | |
| IndBr-o-Me | Me | H | H | Br | H | 1.22 | 11.99 | 9.8 | |
| IndBr-o-I | I | H | H | Br | H | 15.86 | 96.25 | 6.1 | |
| IndI-o-Br | Br | H | H | I | H | 20.41 | 323.2 | 15.8 | |
| IndI-o-Cl | Cl | H | H | I | H | 4.81 | 14.80 | 3.1 | |
| IndI-o-Me | Me | H | H | I | H | 1.38 | 9.64 | 7.0 | |
| IndI-o-I | I | H | H | I | H | 6.62 | 52.90 | 8.0 | |
| IndH-o-F2 | F | H | F | H | H | | | | |
| IndH-o-Cl2 | Cl | H | Cl | H | H | 0.088 | 0.82 | 9.3 | | a. Relative value to 100% for $E_2$. b. *: The level of production of MBP, ---: regression of MBP.

FIG. 9

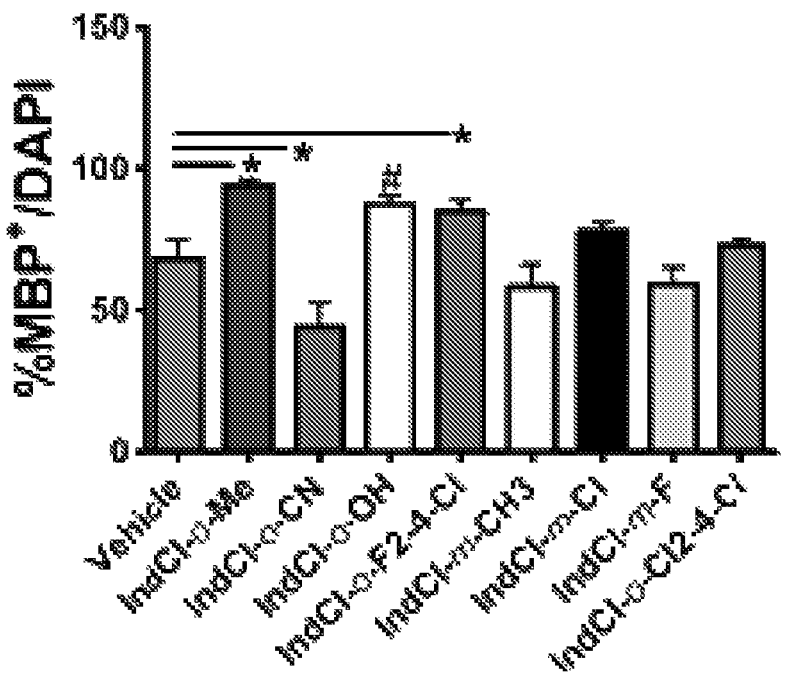
FIG. 10B
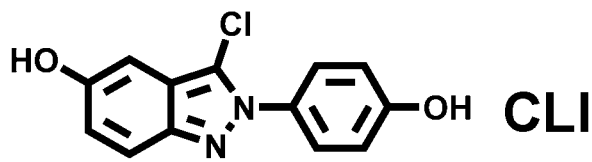
$C_{13}H_9ClN_2O_2$  260.6770
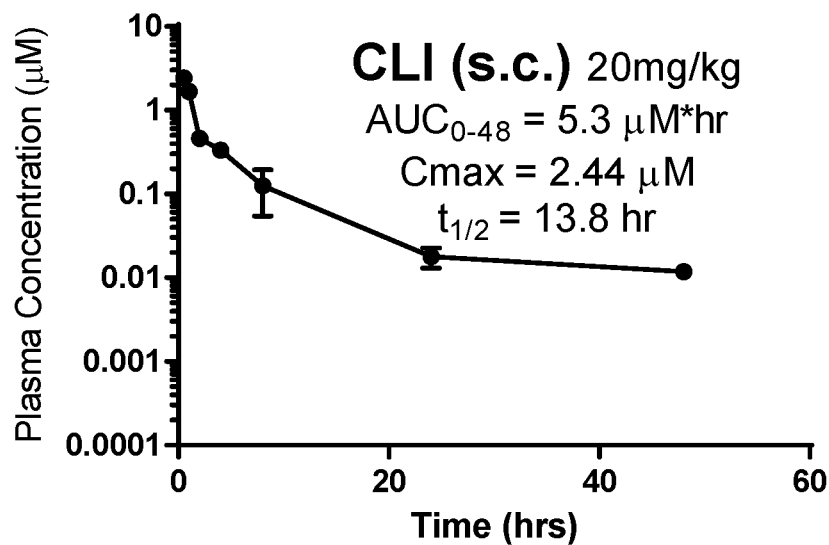
FIG. 11A

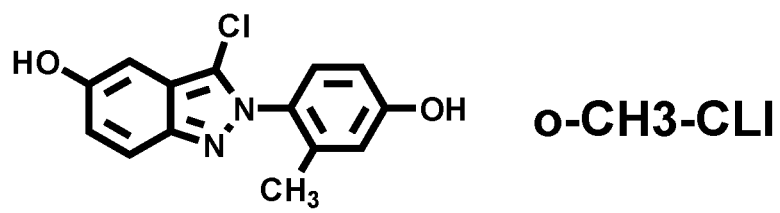
o-CH3-CLI
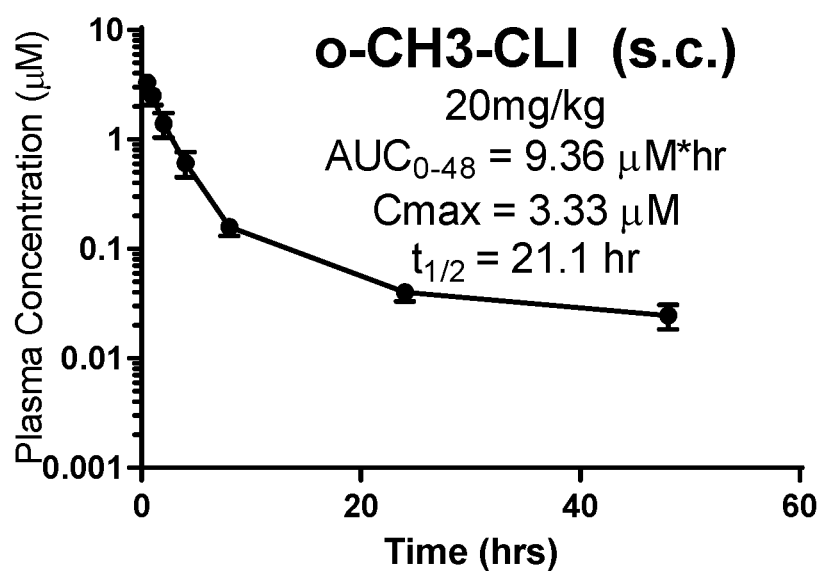
FIG. 11C

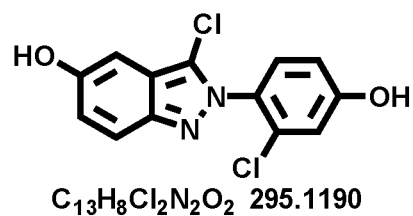
$C_{13}H_8Cl_2N_2O_2$ 295.1190
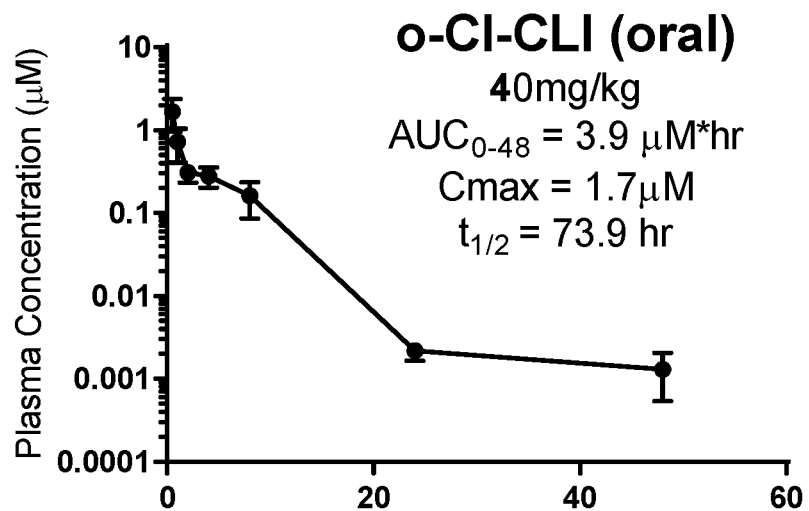
FIG. 11E

ESTROGEN RECEPTOR BETA LIGANDS FOR THE PREVENTION AND TREATMENT OF MULTIPLE SCLEROSIS (MS) AND OTHER DEMYELINATING, INFLAMMATORY AND NEURODEGENERATIVE DISEASES

RELATED APPLICATIONS

This patent application is the U.S. national stage entry, under 35 U.S.C. § 371, of International Application Number PCT/US2019/033824, filed May 23, 2019, which claims priority to U.S. Provisional Application No. 62/675,508, filed May 23, 2018, the entire contents of each of which are hereby incorporated by reference.

STATEMENT REGARDING FEDERALLY SPONSORED RESEARCH OR DEVELOPMENT

This invention was made with government support under grant number R01 DK015556 and grant number R01 NS081141 awarded by the National Institutes of Health (NIH). The government has certain rights in the invention.

TECHNICAL FIELD

The invention relates to estrogen receptor beta ligands and their use in the treatment of demyelinating diseases and endometriosis.

BACKGROUND

Demyelinating diseases are characterized by damage to the myelin sheaths of the central nervous system. Once myelin sheaths are damaged, axons are left exposed and are unable to effectively transmit nerve impulses. Symptoms include vision loss, muscle weakness, muscle stiffness and spasms, loss of coordination, change in sensation, pain, and changes in bladder and bowel function.

Multiple sclerosis (MS) is the most common autoimmune demyelinating and neurodegenerative disease of the central nervous system (CNS). There is no known cause or cure for MS. Experimental autoimmune encephalomyelitis (EAE) recapitulates the inflammation, demyelination, and neurodegeneration observed in MS and is among the most common inducible animal model of MS. The EAE model has been used to develop many currently approved MS treatments, including interferon (IFN), glatiramer acetate, fingolimod, and the anti-CD20 monoclonal antibody, ocrelizumab. Although the approved therapeutics are effective at treating various symptoms and are able to attenuate inflammation, they cannot reverse or prevent neurodegeneration nor initiate remyelination.

Accumulating evidence indicates that estrogens are both neuroprotective and immunomodulatory, making them attractive candidates for the treatment of MS (Khalaj, 2016). Estrogens skew the inflammatory T helper (Th)1 response prevalent in MS towards an anti-inflammatory Th2 profile (Cua et al., 1995; Nicot, 2009). Furthermore, in preclinical studies, treatment with pregnancy levels of the placenta-derived estrogenic hormone estriol attenuated EAE disease severity (Jansson and Holmdahl, 1998; Kim et al., 1999). However, although they display immense potential for treating MS, endogenous estrogen therapy possesses several undesirable or deleterious side effects (Banks and Canfell, 2009). In addition to feminizing male recipients, treatment with endogenous estrogens increase the risk of developing breast and endometrial cancers in females (Banks and Canfell, 2009). Importantly, the carcinogenic effects of estrogens are mediated through estrogen receptor (ER)α and not ERβ, suggesting that therapies targeting specific ER subtypes may impart the benefit of estrogen treatment, while circumventing these side effects (Burns and Korach, 2012).

It is of critical importance to develop and provide new therapeutics that can trigger significant remyelination and offer neuroprotection as well as modulation of the immune system without unwanted side effects.

SUMMARY

The present invention provides compounds or a pharmaceutically acceptable salt thereof and the methods and compositions disclosed herein for treating a demyelinating disease, for differentiating oligodendrocyte progenitor cells, or for promoting remyelination of demyelinated axons.

In one aspect, the invention provides compounds of formula (I), or pharmaceutically acceptable salts thereof

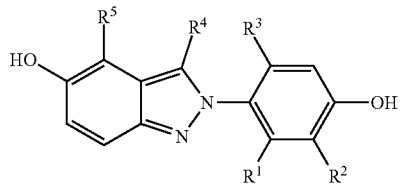

(I)

wherein:
$R^1$ and $R^3$ are independently hydrogen, halogen, $C_{1-4}$alkyl, $C_{2-4}$alkenyl, cyano, $C_{1-4}$haloalkyl, OH, —$OC_{1-4}$alkyl, —$C_{1-4}$alkylene-OH, or 1,3-dithiolan-2-yl;
$R^2$ is hydrogen, halogen, $C_{1-4}$alkyl, cyano, $C_{1-4}$haloalkyl, OH, or —$OC_{1-4}$alkyl;
wherein at least one of $R^1$-$R^3$ is not hydrogen when $R^4$ is hydrogen, halogen, or $C_{1-4}$alkyl;
$R^4$ is hydrogen, halogen, $C_{1-4}$alkyl, $C_{2-4}$alkenyl, —$C_{1-4}$alkylene-OH, 1,3-dithiolan-2-yl, or phenyl optionally substituted with 1-5 substituents independently selected from the group consisting of halogen, $C_{1-4}$alkyl, cyano, $C_{1-4}$haloalkyl, OH, and —$OC_{1-4}$alkyl; and
$R^5$ is hydrogen, halogen, or $C_{1-4}$alkyl;
provided that the compound is not
2-(3-chloro-4-hydroxyphenyl)-2H-indazol-5-ol; or
3-chloro-2-(3-chloro-4-hydroxyphenyl)-2H-indazol-5-ol.

In another aspect, the invention provides compounds of formula (I), or pharmaceutically acceptable salts thereof wherein $R^1$, $R^2$, and $R^3$ are independently hydrogen, halogen, $C_{1-4}$alkyl, cyano, $C_{1-4}$haloalkyl, OH, or —$OC_{1-4}$alkyl, wherein at least one of $R^1$-$R^3$ is not hydrogen; and $R^4$ and $R^5$ are independently hydrogen, halogen, or $C_{1-4}$alkyl; provided that the compound is not 2-(3-chloro-4-hydroxyphenyl)-2H-indazol-5-ol; or 3-chloro-2-(3-chloro-4-hydroxyphenyl)-2H-indazol-5-ol.

In another aspect, the invention provides a pharmaceutical composition comprising a compound of formula (I), or a pharmaceutically acceptable salt thereof, and a pharmaceutically acceptable carrier.

In another aspect, the invention provides a method of treating a demyelinating disease comprising administering, to a subject in need thereof, a therapeutically effective amount of the compound of formula (I), or a pharmaceutically acceptable salt or composition thereof.

In another aspect the invention provides a method of promoting remyelination of demyelinated axons comprising administering to a subject in need thereof a therapeutically effective amount of the compound of formula (I), or a pharmaceutically acceptable salt or composition thereof.

In another aspect the invention provides a method of differentiating oligodendrocyte progenitor cells comprising administering to a subject in need thereof a therapeutically effective amount of the compound of formula (I), or a pharmaceutically acceptable salt or composition thereof.

In another aspect, the invention provides a method of treating endometriosis comprising administering, to a subject in need thereof, a therapeutically effective amount of the compound of formula (I), or a pharmaceutically acceptable salt or composition thereof.

In another aspect, the invention provides a compound of formula (I), or a pharmaceutically acceptable salt or composition thereof, for use in the treatment of a demyelinating disease, or in the promotion of remyelination of demyelinated axons, or in the differentiation of oligodendrocyte progenitor cells, or in the treatment of endometriosis.

In another aspect, the invention provides the use of a compound of formula (I), or a pharmaceutically acceptable salt or composition thereof, in the manufacture of a medicament for the treatment of a demyelinating disease, or for the promotion of remyelination of demyelinated axons, or for the differentiation of oligodendrocyte progenitor cells, or for the treatment of endometriosis.

In another aspect, the invention provides a kit comprising a compound of formula (I), or a pharmaceutically acceptable salt or composition thereof, and instructions for use.

BRIEF DESCRIPTION OF THE DRAWINGS

The features, objects and advantages other than those set forth above will become more readily apparent when consideration is given to the detailed description below. Such detailed description makes reference to the following drawings.

FIG. 9 shows IndCl analogues and a summary of the binding data to Estrogen Receptor alpha and beta.

FIG. 10B shows the effects of treatment on the ratio of stain for MBP$^+$ and DAPI (MBP+/DAPI) as an indication of OPC differentiation. IndCl-o-Me, IndCl-o-OH and IndCl-o-F2-4-Cl showed greatest increase in MBP$^+$/DAPI ratio. There were 3 wells/treatment group. n=3 independent experiments were performed.

FIG. 11A shows the pharmacokinetics and half-lives of CLI in mice after subcutaneous administration at 20 mg/kg with either 100 μL 10% ethanol+90% Miglyol 812N or 100 μL 10% DSMO+90% corn oil per mouse.

FIG. 11C shows the pharmacokinetics and half-lives of o-CH3-CLI in mice after subcutaneous administration at 20 mg/kg with either 100 μL 10% ethanol+90% Miglyol 812N or 100 L 10% DSMO+90% corn oil per mouse.

FIG. 11E shows the pharmacokinetics and half-lives of o-Cl-CLI in mice after oral administration at 40 mg/kg (200 μL 2-hydroxypropyl-β-CD 40% aqueous solution MW ~1540 per mouse).

Figure 1A:
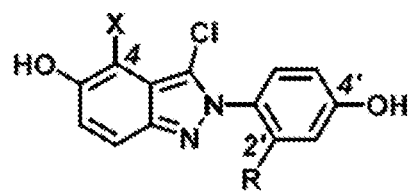
FIG. 1A shows the relative binding to estrogen receptor alpha and beta of chloroindazole (IndCl) and seven analogues, IndCl-o-Cl, IndCl-o-Br, IndCl-o-Me, IndCl-o-I, IndCl-o-F, IndCl-o-Cl-4-Cl, and IndCl-o-$CF_3$.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments above and claims below for interpreting the scope of the invention.

The patent or application file contains at least one drawing executed in color. Copies of this patent or patent application publication with color drawing(s) will be provided by the Office upon request and payment of the necessary fee.

DETAILED DESCRIPTION

1. Definitions

As described herein, compounds of the invention can optionally be substituted with one or more substituents, such as are illustrated generally above, or as exemplified by particular classes, subclasses, and species of the invention. As described herein, the variables in formula I encompass specific groups, such as, for example, alkyl and cycloalkyl. As one of ordinary skill in the art will recognize, combinations of substituents envisioned by this invention are those combinations that result in the formation of stable or chemically feasible compounds. The term "stable," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

Unless otherwise defined, all technical and scientific terms used herein have the same meaning as commonly understood by one of ordinary skill in the art. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkyl" as used herein, means a straight or branched chain saturated hydrocarbon. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond.

The term "alkylene," as used herein, refers to a divalent group derived from a straight or branched chain saturated hydrocarbon, for example, of 2 to 5 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "halogen" means a chlorine, bromine, iodine, or fluorine atom.

The term "haloalkyl," as used herein, means an alkyl, as defined herein, in which one, two, three, four, five, six, or seven hydrogen atoms are replaced by halogen. For example, representative examples of haloalkyl include, but are not limited to, 2-fluoroethyl, difluoromethyl, trifluoromethyl, 2,2,2-trifluoroethyl, 2,2,2-trifluoro-1, 1-dimethylethyl, and the like.

Terms such as "alkyl," "cycloalkyl," "alkylene," "cycloalkylene," etc. may be preceded by a designation indicating the number of atoms present in the group in a particular instance (e.g., "C$_{1-4}$alkyl," "C$_{1-4}$alkylene"). These designations are used as generally understood by those skilled in the art. For example, the representation "C" followed by a subscripted number indicates the number of carbon atoms present in the group that follows. Thus, "C$_3$alkyl" is an alkyl group with three carbon atoms (i.e., n-propyl, isopropyl). Where a range is given, as in "C$_{1-4}$," the members of the group that follows may have any number of carbon atoms falling within the recited range. A "C$_{1-4}$alkyl," for example, is an alkyl group having from 1 to 4 carbon atoms, however arranged (i.e., straight chain or branched).

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Thus, included within the scope of the invention are tautomers of compounds of formula I. The structures also include zwitterionic forms of the compounds or salts of formula I where appropriate.

The terms "effective amount" or "therapeutically effective amount," as used herein, refer to a sufficient amount of an agent or a composition or combination of compositions being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. The dose could be administered in one or more administrations. However, the precise determination of what would be considered an effective dose may be based on factors individual to each patient, including, but not limited to, the patient's age, size, type or extent of disease, stage of the disease, route of administration of the regenerative cells, the type or extent of supplemental therapy used, ongoing disease process and type of treatment desired (e.g., aggressive vs. conventional treatment).

As used herein, "treat," "treating" and the like means a slowing, stopping or reversing of progression of a disease or disorder when provided a composition described herein to an appropriate control subject. The term also means a reversing of the progression of such a disease or disorder to a point of eliminating or greatly reducing the cell proliferation. As such, "treating" means an application or administration of the compositions described herein to a subject, where the subject has a disease or a symptom of a disease, where the purpose is to cure, heal, alleviate, relieve, alter, remedy, ameliorate, improve or affect the disease or symptoms of the disease.

A "subject" or "patient" may be human or non-human and may include, for example, animal strains or species used as "model systems" for research purposes, such a mouse model as described herein. Likewise, patient may include either adults or juveniles (e.g., children). Moreover, patient may mean any living organism, preferably a mammal (e.g., human or non-human) that may benefit from the administration of compositions contemplated herein. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

As used herein, the terms "providing", "administering," "introducing," are used interchangeably herein and refer to the placement of the compositions of the disclosure into a subject by a method or route which results in at least partial localization of the composition to a desired site. The compositions can be administered by any appropriate route which results in delivery to a desired location in the subject.

2. Compounds

A first aspect of the invention provides compounds or compositions of formula (I), or a pharmaceutically acceptable salt thereof, wherein $R^1$-$R^5$ are as defined herein.

In the compounds disclosed herein, $R^1$ may be hydrogen, halogen (e.g., F, Cl, Br, I), C$_{1-4}$alkyl (e.g., CH$_3$), C$_{2-4}$alkenyl (e.g., vinyl, allyl), cyano, C$_{1-4}$haloalkyl (e.g., C$_{1-4}$fluoroalkyl such as CF$_3$), OH, —C$_{1-4}$alkylene-OH (e.g., —CH$_2$OH), or 1,3-dithiolan-2-yl, wherein $R^2$-$R^5$ are as defined herein. $R^1$ may be halogen (e.g., F, Cl, Br, I), C$_{1-4}$alkyl (e.g., CH$_3$), C$_{2-4}$alkenyl (e.g., vinyl, allyl), cyano, C$_{1-4}$haloalkyl (e.g., C$_{1-4}$fluoroalkyl such as CF$_3$), OH, —C$_{1-4}$alkylene-OH (e.g., —CH$_2$OH), or 1,3-dithiolan-2-yl. $R^1$ may be C$_{2-4}$alkenyl, —C$_{1-4}$alkylene-OH, or 1,3-dithiolan-2-yl. In some embodiments, R$^1$ is hydrogen, fluoro, chloro, bromo, iodo, cyano, CH$_3$, CF$_3$, OH, —CH$_2$OH, vinyl, or 1,3-dithiolan-2-yl.

In some embodiments, R$^1$ is halogen (e.g., F, Cl, Br, I), C$_{1-4}$alkyl (e.g., CH$_3$), cyano, C$_{1-4}$haloalkyl (e.g., CF$_3$), OH, or —OC$_{1-4}$alkyl, wherein R$^2$-R$^5$ are as defined herein. In further embodiments, R$^1$ is halogen, C$_{1-4}$alkyl, cyano, C$_{1-4}$haloalkyl, or OH. In still further embodiments, R$^1$ is chloro or methyl.

In some embodiments, R$^2$ is hydrogen, halogen (e.g., F, Cl), or C$_{1-4}$alkyl (e.g., CH$_3$), wherein R$^1$ and R$^3$-R$^5$ are as defined herein. In further embodiments, R$^2$ is hydrogen.

In some embodiments, R$^3$ is hydrogen or halogen (e.g., F, Cl), wherein R$^1$-R$^2$ and R$^4$—R are as defined herein. In further embodiments, R$^3$ is hydrogen.

In the compounds disclosed herein, R$^1$ and R$^3$ may be simultaneously hydrogen. In the compounds disclosed herein, R$^1$ and R$^3$ may be simultaneously a non-hydrogen substituent. In the compounds disclosed herein, one of R$^1$ and R$^3$ may be hydrogen and the other a non-hydrogen substituent. In the compounds disclosed herein at least one of R$^1$, R$^2$, and R$^3$ is a non-hydrogen substituent when R$^4$ is hydrogen, halogen, or C$_{1-4}$alkyl. R$^1$, R$^2$, and R$^3$ may each be hydrogen when R$^4$ is C$_{2-4}$alkenyl, —C$_{1-4}$alkylene-OH, 1,3-dithiolan-2-yl, or phenyl optionally substituted with 1-5 substituents independently selected from the group consisting of halogen, C$_{1-4}$alkyl, cyano, C$_{1-4}$haloalkyl, OH, and —OC$_{1-4}$alkyl.

In the compounds disclosed herein, R$^4$ may be hydrogen, halogen (e.g., F, Cl, Br, I), C$_{1-4}$alkyl (e.g., CH$_3$), C$_{2-4}$alkenyl (e.g., vinyl, allyl), —C$_{1-4}$alkylene-OH (e.g., —CH$_2$OH), 1,3-dithiolan-2-yl, or phenyl optionally substituted with 1-5 substituents independently selected from the group consisting of halogen, C$_{1-4}$alkyl, cyano, C$_{1-4}$haloalkyl, OH, and —OC$_{1-4}$alkyl (e.g., 4-hydroxyphenyl), wherein R$^1$-R$^3$ and R$^5$ areas defined herein. R$^4$ may be C$_{2-4}$alkenyl, —C$_{1-4}$alkylene-OH, 1,3-dithiolan-2-yl, or phenyl optionally substituted with 1-5 substituents independently selected from the group consisting of halogen, C$_{1-4}$alkyl, cyano, C$_{1-4}$haloalkyl, OH, and —OC$_{1-4}$alkyl. In some embodiments, R$^4$ is hydrogen, fluoro, chloro, bromo, iodo, vinyl, allyl, —CH$_2$OH, 1,3-dithiolan-2-yl, or 4-hydroxyphenyl. In some embodiments, R$^4$ is hydrogen or halogen (e.g., F, Cl, Br, and I), wherein R$^1$-R$^3$ and R$^5$ are as defined herein. In further embodiments, R$^4$ is halogen. In still further embodiments, R$^4$ is chloro.

In some embodiments, R$^5$ is hydrogen or halogen, wherein R$^1$-R$^4$ are as defined herein. In further embodiments, R$^5$ is hydrogen.

In some embodiments, R$^1$, R$^2$, and R$^3$ are independently hydrogen, halogen, C$_{1-4}$alkyl, cyano, C$_{1-4}$haloalkyl, OH, or —OC$_{1-4}$alkyl, wherein at least one of R$^1$-R$^3$ is not hydrogen; and R$^4$ and R$^5$ are independently hydrogen, halogen, or C$_{1-4}$alkyl.

In some embodiments, the compound of formula (I) has one of the following formulas:

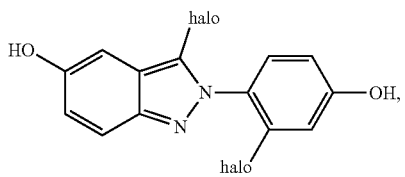

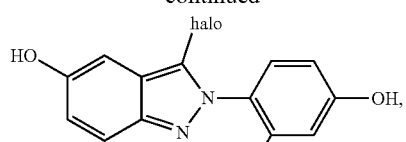

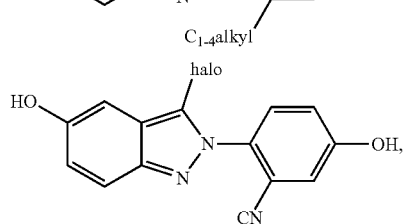

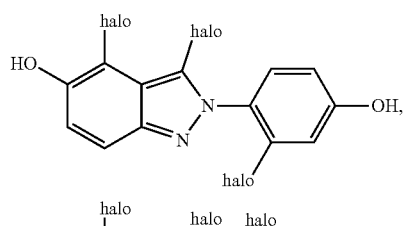

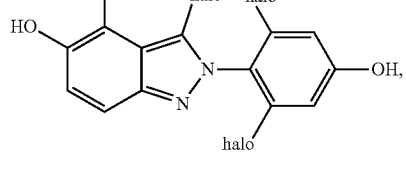

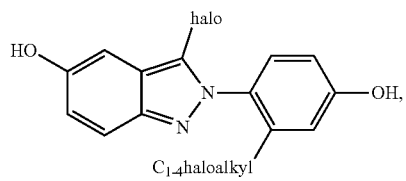

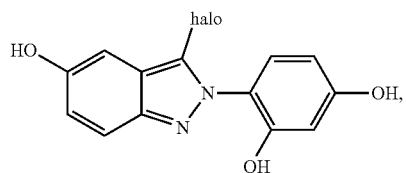

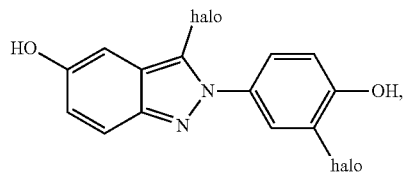

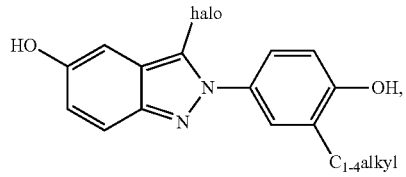

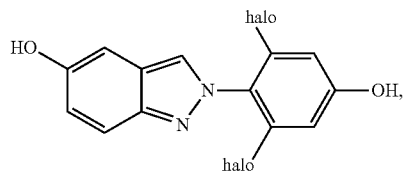

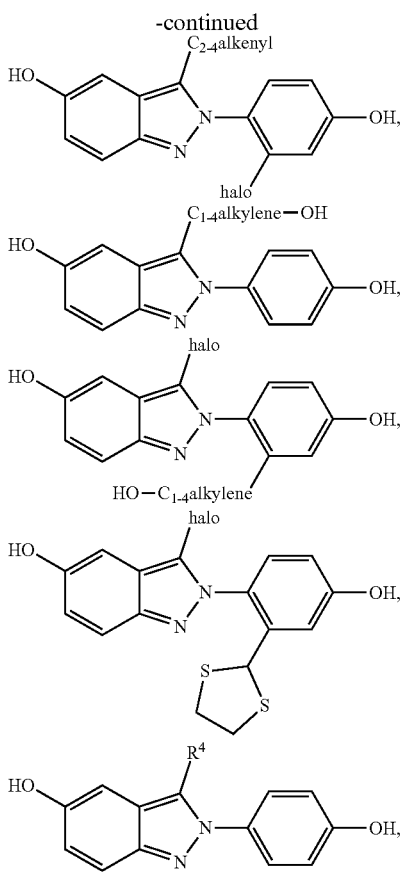

wherein R⁴ is phenyl optionally substituted with 1-5 substituents independently selected from the group consisting of halogen, $C_{1-4}$alkyl, cyano, $C_{1-4}$haloalkyl, OH, and —O$C_{1-4}$alkyl.

In some embodiments, the compound of formula (I) is selected from the group consisting of:
2-(2-bromo-4-hydroxyphenyl)-3-chloro-2H-indazol-5-ol;
3-chloro-2-(2-chloro-4-hydroxyphenyl)-2H-indazol-5-ol;
3-chloro-2-(4-hydroxy-2-methylphenyl)-2H-indazol-5-ol;
3-chloro-2-(4-hydroxy-2-iodophenyl)-2H-indazol-5-ol;
3-chloro-2-(2-fluoro-4-hydroxyphenyl)-2H-indazol-5-ol;
2-(3-chloro-5-hydroxy-2H-indazol-2-yl)-5-hydroxybenzonitrile;
3,4-dichloro-2-(2-chloro-4-hydroxyphenyl)-2H-indazol-5-ol;
3,4-dichloro-2-(2,6-difluoro-4-hydroxyphenyl)-2H-indazol-5-ol;
3,4-dichloro-2-(2,6-dichloro-4-hydroxyphenyl)-2H-indazol-5-ol;
3-chloro-2-(4-hydroxy-2-(trifluoromethyl)phenyl)-2H-indazol-5-ol;
4-(3-chloro-5-hydroxy-2H-indazol-2-yl)benzene-1,3-diol;
3-chloro-2-(3-fluoro-4-hydroxyphenyl)-2H-indazol-5-ol;
3-chloro-2-(4-hydroxy-3-methylphenyl)-2H-indazol-5-ol;
2-(2-bromo-4-hydroxyphenyl)-3-fluoro-2H-indazol-5-ol;
2-(2-chloro-4-hydroxyphenyl)-3-fluoro-2H-indazol-5-ol;
3-fluoro-2-(4-hydroxy-2-methylphenyl)-2H-indazol-5-ol;
3-fluoro-2-(4-hydroxy-2-iodophenyl)-2H-indazol-5-ol;
3-bromo-2-(2-bromo-4-hydroxyphenyl)-2H-indazol-5-ol;
3-bromo-2-(2-chloro-4-hydroxyphenyl)-2H-indazol-5-ol;
3-bromo-2-(4-hydroxy-2-methylphenyl)-2H-indazol-5-ol;
3-bromo-2-(4-hydroxy-2-iodophenyl)-2H-indazol-5-ol;
2-(2-bromo-4-hydroxyphenyl)-3-iodo-2H-indazol-5-ol;
2-(2-chloro-4-hydroxyphenyl)-3-iodo-2H-indazol-5-ol;
2-(4-hydroxy-2-methylphenyl)-3-iodo-2H-indazol-5-ol;
2-(4-hydroxy-2-iodophenyl)-3-iodo-2H-indazol-5-ol;
2-(2,6-difluoro-4-hydroxyphenyl)-2H-indazol-5-ol;
2-(2,6-dichloro-4-hydroxyphenyl)-2H-indazol-5-ol;
2-(2-bromo-4-hydroxyphenyl)-3-vinyl-2H-indazol-5-ol;
3-allyl-2-(2-bromo-4-hydroxyphenyl)-2H-indazol-5-ol;
3-allyl-2-(4-hydroxy-2-vinylphenyl)-2H-indazol-5-ol;
3-(hydroxymethyl)-2-(4-hydroxyphenyl)-2H-indazol-5-ol;
3-chloro-2-(4-hydroxy-2-(hydroxymethyl)phenyl)-2H-indazol-5-ol;
3-(1,3-dithiolan-2-yl)-2-(4-hydroxyphenyl)-2H-indazol-5-ol;
2-(2-(1,3-dithiolan-2-yl)-4-hydroxyphenyl)-3-chloro-2H-indazol-5-ol; and
4,4'-(5-hydroxy-2H-indazole-2,3-diyl)diphenol, or a pharmaceutically acceptable salt thereof.

Certain compounds may exist in one or more particular geometric, optical, enantiomeric, diastereomeric, epimeric, atropic, stereoisomer, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and ( ) forms; keto-, enol-, and enolate-forms; syn- and anti-forms; synclinal- and anticlinal-forms; α- and β-forms; axial and equatorial forms; boat-, chair-, twist-, envelope-, and half chair-forms; and combinations thereof, hereinafter collectively referred to as "isomers" (or "isomeric forms").

Compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

Exemplary tautomeric forms include, for example, the following tautomeric pairs: keto/enol and imine/enamine.

In another embodiment, the compounds include isotope-labelled forms. An isotope-labelled form of a compound is identical to the compound apart from the fact that one or more atoms of the compound have been replaced by an atom or atoms having an atomic mass or mass number which differs from the atomic mass or mass number of the atom which usually occurs in greater natural abundance. Examples of isotopes which are readily commercially available and which can be incorporated into a compound by well-known methods include isotopes of hydrogen, carbon, nitrogen, oxygen, fluorine and chlorine, for example $^2H$, $^3H$, $^{13}C$, $^{14}C$, $^{15}N$, $^{18}O$, $^{17}O$, $^{18}F$ and $^{36}Cl$. Isotopically-labeled compounds of formula (I) can generally be prepared by conventional techniques known to those skilled in the art or by processes analogous to those described in the accompanying Examples include using an appropriate isotopically-labeled reagent in place of non-isotopically-labeled reagent.

3. Methods of Use

Methods

In some embodiments, the compounds of formula (I) may decrease pro-inflammatory cytokines and/or increase anti-inflammatory cytokines. In another embodiment, methods of the present invention may comprise decreasing pro-inflammatory cytokines and/or increasing anti-inflammatory cytokines with a compound of formula (I) or a composition thereof. In another embodiment, methods of the present invention may be useful for treating or lessening the severity of a disease or disorder selected from a disease or disorder associated with an increase in pro-inflammatory cytokines comprising administering a therapeutically effective amount of the compounds of formula (I) or compositions thereof to a subject in need thereof.

In some embodiments, the compounds of formula (I) may promote oligodendrocyte proliferation, differentiation or survival. In one embodiment, the methods described herein also provide a method of promoting oligodendrocyte proliferation, differentiation or survival comprising contacting oligodendrocytes with a compound of formula (I) or a composition thereof.

In another embodiment, a method of the present invention comprises promoting oligodendrocyte proliferation, differentiation or survival. In another embodiment, a method of the present invention is useful for treating or lessening the severity of a disease or disorder selected from a disease or disorder associated with a lack of oligodendrocyte proliferation, differentiation or survival comprising administering a therapeutically effective amount of the compounds of formula (I) or compositions thereof to a subject in need thereof.

In some embodiments, the compounds of formula (I) may increase chemokines involved in oligodendrocyte precursor cell proliferation, differentiation and survival. In another embodiment, methods of the present invention may increase chemokines involved in oligodendrocyte precursor cell proliferation, differentiation and survival with a compound of formula (I) or a composition thereof.

In some embodiments, the compounds of formula (I) may suppress production of chemokines and/or cytokines which promote oligodendrocyte death. In another embodiment, methods of the present invention may decrease production of chemokines and/or cytokines involved in oligodendrocyte death with a compound of formula (I) or a composition thereof.

In another embodiment, a method of the present invention comprises promoting myelination by contacting neuronal cells, oligodendrocyte cells or oligodendrocyte precursor cells with a compound of formula (I) or a composition thereof.

In another embodiment, a method of the present invention is useful for treating or lessening the severity of a disease or disorder selected from a disease or condition associated with demyelination comprising administering a therapeutically effective amount of the compounds of formula (I) or compositions thereof to a subject in need thereof. In one embodiment, the disease or condition associated with demyelination is a CNS disorder or a CNS demyelinating disease as described herein. In one embodiment, the disease is multiple sclerosis.

In another embodiment, the subject has, or is at risk of having, multiple sclerosis. The subject with multiple sclerosis can be at any stage of treatment or disease. The subject with multiple sclerosis may have one or more of: benign multiple sclerosis, relapsing remitting multiple sclerosis, quiescent relapsing remitting multiple sclerosis, active relapsing remitting multiple sclerosis, progressive relapsing multiple sclerosis, primary progressive multiple sclerosis, or secondary progressive multiple sclerosis, clinically isolated syndrome, or clinically defined multiple sclerosis. The subject may be asymptomatic. The subject may have one or more multiple sclerosis-like symptoms, such as those having clinically isolated syndrome or clinically defined multiple sclerosis. The subject may have one or more multiple sclerosis relapses.

In some embodiments, the subject has a relapsing form of multiple sclerosis such as relapsing remitting multiple sclerosis or relapsing secondary progressive multiple sclerosis. In one embodiment, the subject has relapsing remitting multiple sclerosis and has one or more ongoing clinical exacerbations. In another embodiment, the subject has relapsing remitting multiple sclerosis and one or more subclinical activities. In one embodiment, the clinical exacerbation or subclinical activity may be shown by white matter lesions using magnetic resonance imaging.

In one embodiment, the clinical exacerbations or subclinical activities may be monitored by a functional readout such as ambulatory changes (gait changes, sway changes, etc.), T25W changes and or EDSS changes. In another embodiment, the clinical exacerbations or subclinical activities may be monitored by a visual evoked potential assay, a visual acuity assay, a measurement of optic nerve thickness or a myelin labelling assay.

The subject with multiple sclerosis can be at any stage of treatment or disease and treatment with compounds of formula (I) of the present invention result in improvement of the disease or symptoms. In one embodiment, improvement in the disease or symptoms is evidenced by a reduction or disappearance of one or more white matter lesions in the brain. In another embodiment, improvement in the disease or symptoms is evidenced by improved function such as improved ambulation, improved gait, reduced sway, improved T25W scores or improved EDSS scores. In another embodiment, improvement in the disease or symptoms is evidenced by improvements in a visual acuity assay or a visual evoked potential assay. In another embodiment, improvement in the disease or symptoms is evidenced by enhanced optic nerve thickness. In another embodiment, improvement in the disease or symptoms is evidenced by increased myelination in a myelin labelling assay.

In another embodiment, the compounds of formula (I) of the present invention and the methods, compositions and kits disclosed herein are useful for promoting myelin regeneration in progressive demyelinating diseases. In one embodiment, the compounds of formula I of the present invention and the methods, compositions and kits disclosed herein are useful for promoting myelin regeneration in primary progressive multiple sclerosis. In another embodiment, the compounds of formula I of the present invention and the methods, compositions and kits disclosed herein are useful for promoting myelin regeneration in secondary progressive multiple sclerosis. In another embodiment, the compounds of formula I of the present invention and the methods, compositions and kits disclosed herein are useful for promoting myelin regeneration in relapsing-remitting multiple sclerosis. In another embodiment, the compounds of formula I of the present invention and the methods, compositions and kits disclosed herein are useful for promoting myelin regeneration in progressive relapsing multiple sclerosis.

In yet another embodiment, the compounds of formula I of the present invention and the methods, compositions and kits disclosed herein are useful for promoting remyelination at the cellular level wherein oligodendrocyte cells are stimulated to regenerate or differentiate. In another embodiment, the compounds of formula I of the present invention and the methods, compositions and kits disclosed herein are useful for promoting remyelination at the cellular level wherein oligodendrocyte cells are stimulated to remyelinate axons.

In another embodiment, the compounds of formula I of the present invention and the methods, compositions and kits disclosed herein are useful for promoting remyelination at the cellular level whereby oligodendrocyte cells are stimulated to regenerate or differentiate thereby treating demyelinating diseases or disorders. In yet another embodiment, the compounds of formula I of the present invention and the methods, compositions and kits disclosed herein are useful for promoting remyelination at the cellular level whereby axons are remyelinated by oligodendrocyte cells thereby treating demyelinating diseases or disorders.

In another aspect, the present invention provides a method of treating or lessening the severity of, in a subject, a demyelinating disease comprising administering an effective amount of a compound, a pharmaceutically acceptable salt thereof or a pharmaceutical composition of the compounds of formula I. The demyelinating diseases may be a demyelinating myelinoclastic disease or a demyelinating leukodystrophic disease. The demyelinating myelinoclastic disease may be multiple sclerosis, Devic's disease or another inflammatory demyelinating disorder. The demyelinating leukodystrophic disease may be a central nervous system neuropathy, central pontine myelinolysis, a leukodystrophy, or another myelopathy. The demyelinating disease may affect the central nervous system or may affect the peripheral nervous system. Demyelinating disease of the the peripheral nervous system include: Guillain-Barre syndrome and its chronic counterpart, chronic inflammatory demyelinating polyneuropathy; anti-MAG peripheral neuropathy; Charcot-Marie-Tooth disease and its counterpart hereditary neuropathy with liability to pressure palsy; copper deficiency associated conditions (peripheral neuropathy, myelopathy, and rarely optic neuropathy); and progressive inflammatory neuropathy.

In another aspect, the present invention provides a method for treating, preventing or ameliorating one or more symptoms of multiple sclerosis or another neurodegenerative disease selected from auditory impairment, optic neuritis, decreased visual acuity, diplopia, nystagmus, ocular dvsmetria, internuclear ophthalmoplegia, movement and sound phosphenes, afferent pupillary defect, paresis, monoparesis, paraparesis, hemiparesis, quadraparesis, plegia, paraplegia, hemiplegia, tetraplegia, quadraplegia, spasticity, dysarthria, motor dysfunction, walking impairment, muscle atrophy, spasms, cramps, hypotonia, clonus, myoclonus, myokymia, restless leg syndrome, gait disturbances, footdrop, dysfunctional reflexes, pallesthesia, anaesthesia, neuralgia, neuropathic and neurogenic pain, L'hermitte's, proprioceptive dysfunction, trigeminal neuralgia, ataxia, intention tremor, dvsmetria, vestibular ataxia, vertigo, speech ataxia, dystonia, disability progression, dysdiadochokinesia, frequent micturation, bladder spasticity, flaccid bladder, detrusor-sphincter dyssynergia, erectile dysfunction or anorgasmy comprising administering an effective amount of a compound, a pharmaceutically acceptable salt thereof or a pharmaceutical composition of the compounds of formula I with one or more additional therapeutic agents administered concurrently with, prior to, or subsequent to treatment with the compound or pharmaceutical composition.

In another aspect, the present invention provides a method for treating, preventing or ameliorating one or more symptoms of endometriosis comprising administering an effective amount of a compound, a pharmaceutically acceptable salt thereof or a pharmaceutical composition of the compounds of formula I to a subject in need thereof.

Administration

As described herein, compounds of the present invention, or a pharmaceutically acceptable salt thereof, or a pharmaceutical composition as described elsewhere herein, can be administered to such subjects by a variety of methods. In any of the uses or methods described herein, administration can be by various routes known to those skilled in the art, including without limitation oral, inhalation, intravenous, intramuscular, topical, subcutaneous, systemic, and/or intraperitoneal administration to a subject in need thereof.

The amount of the compound of the present invention, or a pharmaceutically acceptable salt thereof, required for use in treatment will vary not only with the particular compound or salt selected but also with the route of administration, the nature and/or symptoms of the estrogen receptor dependent and/or estrogen receptor mediated disease or condition being treated and the age and condition of the patient and will be ultimately at the discretion of the attendant physician or clinician. In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the dosage ranges described herein in order to effectively and aggressively treat particularly aggressive estrogen receptor dependent and/or estrogen receptor mediated diseases or conditions.

In some embodiments, the compounds, or pharmaceutically acceptable salts thereof, or pharmaceutical compositions as disclosed herein may be administered by inhalation, oral administration, or intravenous administration. In general, however, a suitable dose will often be in the range of from about 0.01 mg/kg to about 100 mg/kg, such as from about 0.05 mg/kg to about 10 mg/kg. For example, a suitable dose may be in the range from about 0.10 mg/kg to about 7.5 mg/kg of body weight per day, such as about 0.10 mg/kg to about 0.50 mg/kg of body weight of the recipient per day, about 0.10 mg/kg to about 1.0 mg/kg of body weight of the recipient per day, about 0.15 mg/kg to about 5.0 mg/kg of body weight of the recipient per day, about 0.2 mg/kg to 4.0 mg/kg of body weight of the recipient per day. The compound may be administered in unit dosage form; for example, containing 1 to 100 mg, 10 to 100 mg or 5 to 50 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies. For example, useful dosages of a compound of the present invention, or pharmaceutically acceptable salts thereof, can be determined by comparing their in vitro activity, and in vivo activity in animal models. Such comparison can be done by comparison against an established drug, such as fulvestrant.

Dosage amount and interval may be adjusted individually to provide plasma levels of the active moiety which are sufficient to maintain the modulating effects, or minimal effective concentration (MEC). The MEC will vary for each compound but can be estimated from in vivo and/or in vitro data. Dosages necessary to achieve the MEC will depend on individual characteristics and route of administration. However, FIPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the estrogen receptor dependent and/or estrogen receptor mediated disease or condition to be treated and to the route of administration. The severity of the estrogen receptor dependent and/or estrogen receptor mediated disease or condition may, for example, be evaluated, in part, by standard prognostic evaluation methods. Further, the dose, and perhaps dose frequency, will also vary according to the age, body weight, and response of the individual patient. A program comparable to that discussed above may be used in veterinary medicine.

Compounds, salts and compositions disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

A therapeutically effective amount of a compound disclosed herein, or a pharmaceutically acceptable salt thereof, or a pharmaceutical composition as disclosed herein may be administered alone or in combination with a therapeutically effective amount of at least one additional therapeutic agents. In some embodiments, the compounds or pharmaceutical compositions as disclosed herein are administered in combination with at least one additional therapeutic agents. In some embodiments, the at least one additional therapeutic is administered prior to or following administration of the compounds or pharmaceutical compositions as disclosed herein. In some embodiments, compounds and compositions of the invention may be administered in combination with one or more of interferon beta-1a, interferon beta-1b, glatiramer acetate, peginterferon beta-1a, daclizumab, teriflunomide, fingolimod, dimethyl fumarate, alemtuzumab, mitoxantrone, orelizumab, or natalizumab. In some embodiments, compounds and compositions of the invention may be adminstered in combination with one or more of methylprednisolone, prednisone, ACTH, onabotulinumtoxin A, despmopressin, tolterodine, oxybutynin, darifenacin, tamsulosin, terazosin, prazosin, mirabegron, propantheline, trospium chloride, imipramine, solifenacin succinate, dantrolene, baclofen, clonazepam, diazepam, tizanidine, isoniazid, clonazepam, or dalfampridine.

4. Pharmaceutical Compositions

In another aspect of the invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents. In one embodiment, the pharmaceutical composition comprises a therapeutically effective amount of a compound of the present invention or a pharmaceutically acceptable salt thereof and one or more pharmaceutically acceptable carriers or vehicles.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N(C1-4 alkyl)4 salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate and aryl (e.g., phenyl/substituted phenyl) sulfonate.

As described herein, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease being treated.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It can also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, cement, putty, and granules. In such solid dosage forms, the active compound can be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form can also comprise buffering agents.

Solid compositions of a similar type may also be employed as fillers in soft and hardfilled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Dosage forms for topical or trans dermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compounds described herein can be administered as a pharmaceutical composition comprising the compounds of interest in combination with one or more pharmaceutically acceptable carriers. It is understood, however, that the total daily dosage of the compounds and compositions can be decided by the attending physician within the scope of sound medical judgment. The specific therapeutically effective dose level for any particular patient can depend upon a variety of factors including the disorder being treated and the severity of the disorder; activity of the specific compound employed; the specific composition employed; the age, body weight, general health and prior medical history, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved. Actual dosage levels of active ingredients in the pharmaceutical compositions can be varied so as to obtain an amount of the active compound(s) that is effective to achieve the desired therapeutic response for a particular patient and a particular mode of administration. In the treatment of certain medical conditions, repeated or chronic administration of compounds can be required to achieve the desired therapeutic response. "Repeated or chronic administration" refers to the administration of compounds daily (i.e., every day) or intermittently (i.e., not every day) over a period of days, weeks, months, or longer.

The compositions described herein may be administered with additional compositions to prolong stability, delivery, and/or activity of the compositions, or combined with additional therapeutic agents, or provided before or after the administration of additional therapeutic agents.

Combination therapy includes administration of a single pharmaceutical dosage formulation containing one or more of the compounds described herein and one or more additional pharmaceutical agents, as well as administration of the compounds and each additional pharmaceutical agent, in its own separate pharmaceutical dosage formulation. For example, a compound described herein and one or more additional pharmaceutical agents, can be administered to the patient together, in a single oral dosage composition having a fixed ratio of each active ingredient, such as a tablet or capsule; or each agent can be administered in separate oral dosage formulations. Where separate dosage formulations are used, the present compounds and one or more additional pharmaceutical agents can be administered at essentially the same time (e.g., concurrently) or at separately staggered times (e.g., sequentially).

For adults, the doses are generally from about 0.01 to about 100 mg/kg, desirably about 0.1 to about 1 mg/kg body weight per day by inhalation, from about 0.01 to about 100 mg/kg, desirably 0.1 to 70 mg/kg, more desirably 0.5 to 10 mg/kg body weight per day by oral administration, and from about 0.01 to about 50 mg/kg, desirably 0.1 to 1 mg/kg body weight per day by intravenous administration.

The compositions and methods will be described more fully hereinafter with reference to the accompanying drawings, in which some, but not all embodiments of the invention are shown. Indeed, the invention may be embodied in many different forms and should not be construed as limited to the embodiments set forth herein.

Likewise, many modifications and other embodiments of the compositions and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

5. Chemical Synthesis

Compounds of the invention may be prepared as illustrated in the following schemes and examples.

| Abbreviations: | |
|---|---|
| Ac | acetate |
| Ac₂O | acetic anhydride |
| aq. | aqueous |
| Calcd | calculated |
| cat. | catalytic |
| c-HCl | concentrated HCl |
| DCM | dichloromethane |
| DMF | N,N-dimethylformamide |
| eq. | equivalent(s) |
| Et | ethyl |
| ESI | electrospray ionization |
| EtOAc | ethyl acetate |
| h or hr | hour |
| HRMS | high resolution mass spectrometry |
| Me | methyl |
| MeOH | methanol |
| min. | minute(s) |
| NBS | N-bromosuccinimide |
| NCI | negative chemical ionization |
| NCS | N-chlorosuccinimide |
| NIS | N-iodosuccinimide |
| Ph | phenyl |
| ppt | precipitate |
| pTsOH/TsOH | p-toluenesulfonic acid |
| pyr | pyridine |
| rt or r.t. | room temperature |
| sat. | saturated |
| Selectfluor ® bis(tetrafluoroborate) | 1-Chloromethyl-4-fluoro-1,4-diazoniabicyclo[2.2.2]octane |
| TBAF | tetrabutylammonium fluoride |
| THF | tetrahydrofuran |
| TLC | thin layer chromatography |

The general synthetic schemes for the synthesis of the IndCl analogues are shown in Scheme 1 and Scheme 2.

Scheme 1

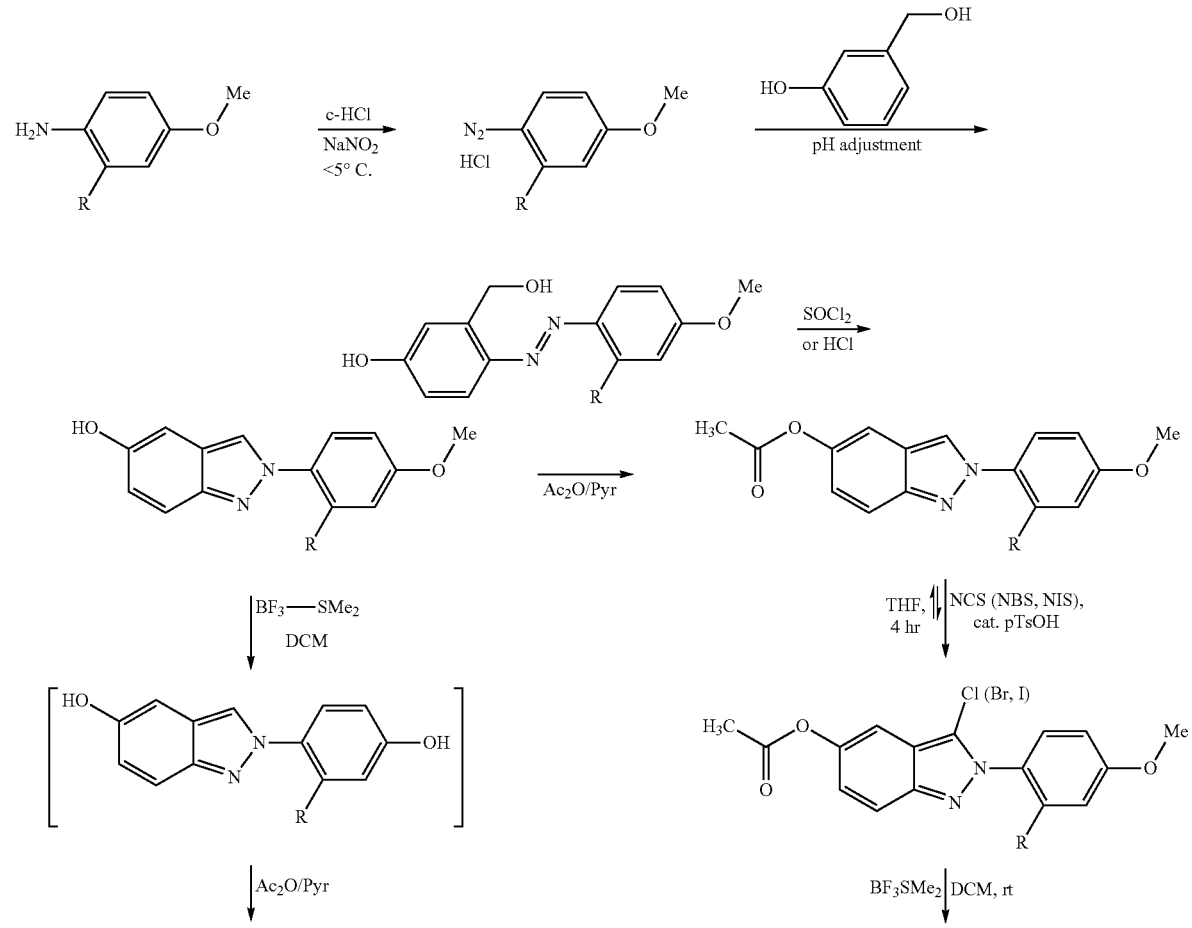

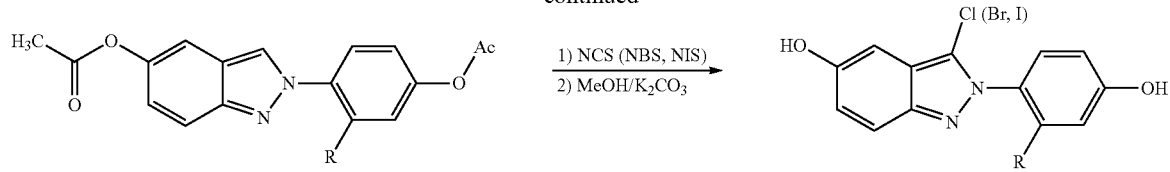
Scheme 2
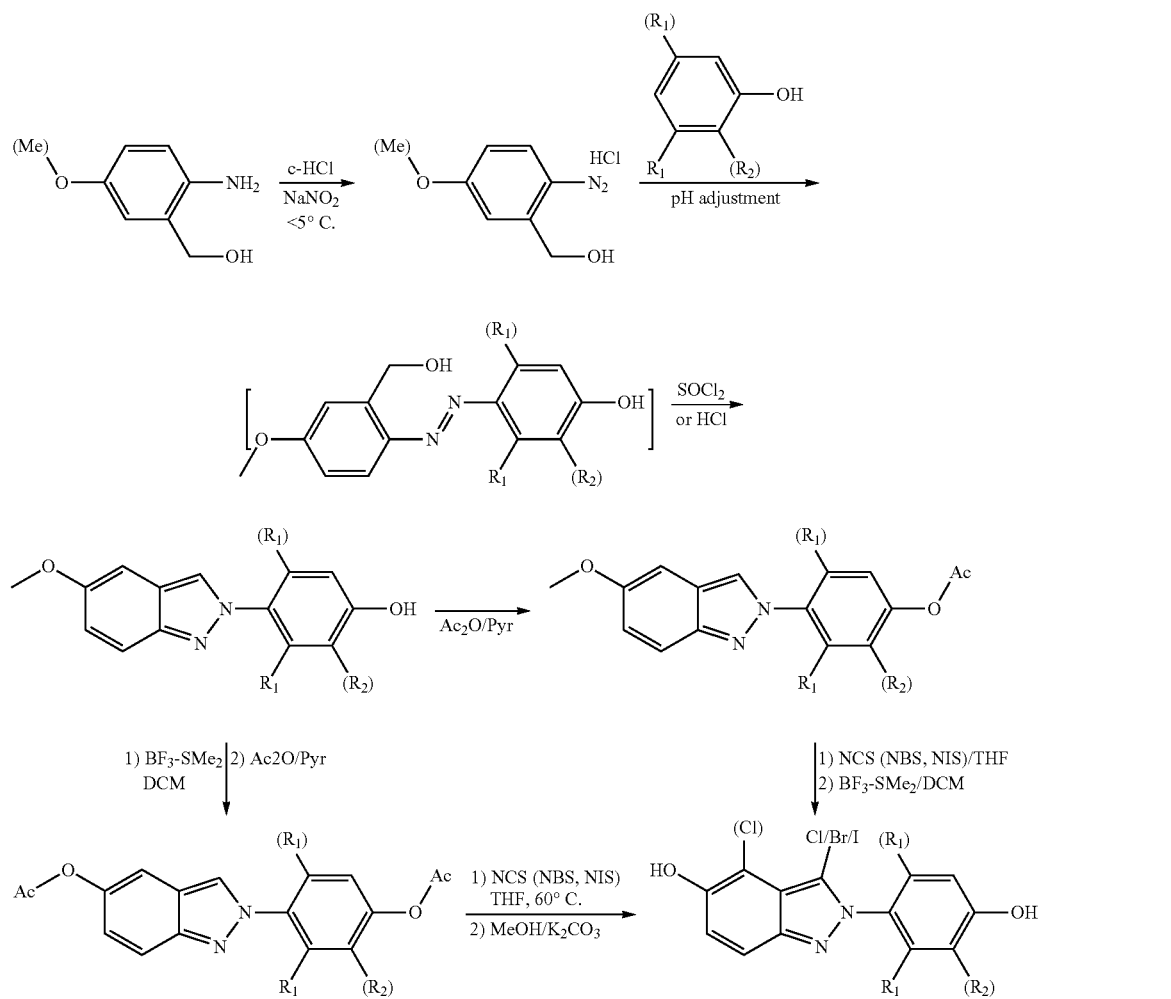
A. Synthesis of 3-chloro-2-(2-chloro-4-hydroxyphenyl)-2H-indazol-5-ol (IndCl-o-Cl)
IndCl-o-Cl was synthesized as shown in Schemes 3-5.
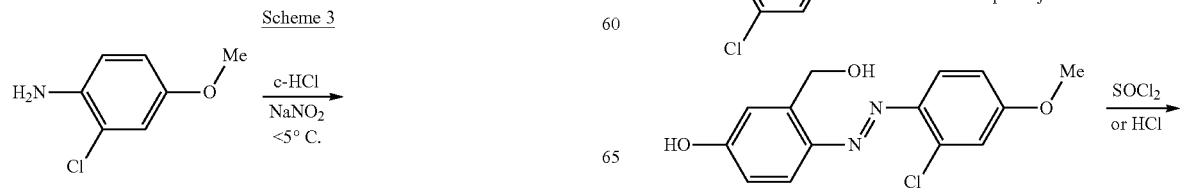

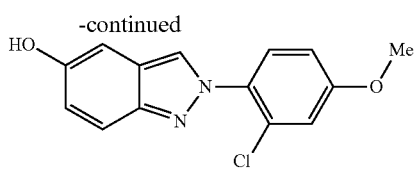

4-((2-chloro-4-methoxyphenyldiazenyl)-3-(hydroxymethyl)phenol (Azo-o-Cl)

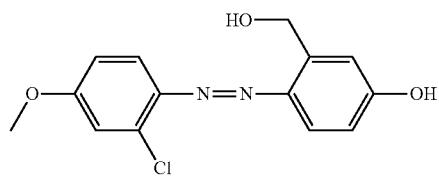 [SMILES: COc1ccc(N=Nc2ccc(O)cc2CO)c(Cl)c1]

To the suspension of 2-chloro-4-methoxyaniline (628 mg, 4.00 mmol) in cold DI water (10 mL), c-HCl (1.2 mL) was added and subsequently, sodium nitrite (284 mg, 4.11 mmol) was added in portions in an ice bath to maintain the temperature below 5° C. After 1.5 hr of stirring the reaction mixture at below 5° C., 3-hydroxymethylphenol (496 mg, 4.00 mmol) in a water-acetone (1:1, v/v, 5 ml) mixture, was added into the reaction mixture in ice bath, then the pH was adjusted up to 7.5 with 1N NaOH to precipitate a yellowish solid. During the addition of the NaOH aq. solution, a massive yellowish solid precipitated from solution as the pH reached ~7.5. The solid was collected by filtration, washed with deionized water, and dried in an oven at ~60-80° C. (1.1 g yellowish solid). It was not necessary to adjust the pH in this case to collect a solid, but in some cases the pH of the solution would need to be acidified to collect more solid. The collected solid was used without further purification. H NMR (500 MHz, $CD_3OD$-$CDCl_3$) δ 3.83 (s, 3H), 4.92 (s, 2H), 6.81 (dd, J=8.5, 3.0 Hz, 1H), 6.83 (dd, J=8.5, 3.0 Hz, 1H), 6.93 (d, J=3.0 Hz, 1H), 7.01 (d, J=3.0 Hz, 1H), 7.63 (d, J=8.5 Hz, 1H), 7.77 (d, J=8.5 Hz, 1H). $^{13}$C NMR (126 MHz, $CD_3OD$-$CDCl_3$) δ 55.93, 62.04, 114.09, 114.95, 115.17, 115.37, 118.75, 123.40, 136.35, 139.98, 143.19, 143.99, 160.52, 161.86. HRMS (ESI, M$^+$+1) $C_{14}H_{14}ClN_2O_3$ Calcd. 293.0693, found 293.0682.

2-(2-chloro-4-methoxyphenyl)-2H-indazol-5-ol (5-Hydroxy-Indazole-o-Cl-4'-OMe)

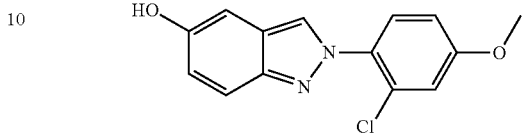

Two methods were used to form the indazole ring from the azo compound. In the first method (Method 1), the dried yellowish solid was suspended into 20 mL dichlomethane and treated with a thionyl chloride (2.00 g, 16.94 mmol) for 30 min in an ice bath. Once thionyl chloride was added, the solution turned scarlet in color and all suspended solid dissolved. To the reaction mixture was added a powder of sodium bicarbonate (3.50 g, 41.67 mmol) and dropwise ice water, until most of sodium bicarbonate was gone. The precipitate that formed was collected by filtration (710 mg).

Alternatively, in the second method (Method 2), the diazo compound in aqueous solution was extracted with ethyl acetate (50 mL×3). To the extract was added 1 mL of c-HCl, and the resulting solution was refluxed until the yellowish diazo compound disappeared on silica gel TLC (20% ethyl acetate in n-hexane, v/v, Rf ~0.8) and new blue fluorescent spot (Rf ~0.65) appeared. The reaction mixture was washed with sat. aq. sodium bicarbonate solution, brine, water, dried over sodium sulfate, followed by filtration and evaporation to afford an enough pure title compound (680 mg) as a pale brownish solid. $^1$H NMR (500 MHz, $CD_3OD$-$CDCl_3$) δ 3.82 (s, 3H), 6.88 (dd, J=2.5, 8.5 Hz, 1H), 6.90 (s, 1H), 7.00 (dd, J=8.5, 2.5 Hz, 1H), 7.02 (d, J=2.5 Hz, 1H), 7.44 (d, J=8.5 Hz, 1H), 7.55 (d, J=8.5 Hz, 1H), 7.96 (s, 1H). $^{13}$C NMR (126 MHz, $CD_3OD$-$CDCl_3$) δ 59.97, 103.96, 117.47, 119.57, 122.53, 125.84, 126.43, 128.40, 133.17, 134.48, 135.66, 149.90, 156.11, 164.44. HRMS (ESI, M$^+$+1) $C_{14}H_{12}ClN_2O_2$ Calcd. 275.0578, found 275.0587.

Scheme 4

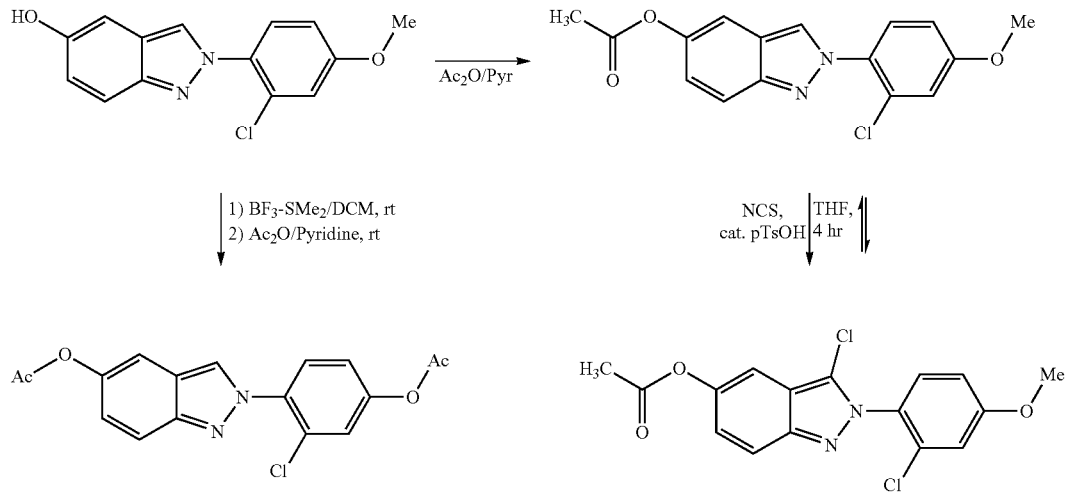

2-(2-chloro-4-methoxyphenyl)-2H-indazol-5-yl acetate (5-AcO-Indazol-o-Cl-4'-OMe)

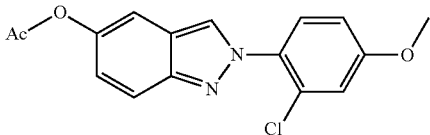 [SMILES: COc1ccc(-n2cc3cc(OC(C)=O)ccc3n2)c(Cl)c1]

To the powder of 2-(2-chloro-4-methoxyphenyl)-2H-indazol-5-ol (400 mg, 1.46 mmol) was added acetic anhydride (2 mL) and dry pyridine (1 mL). The resultant solution was heated up 90° C. for 1 hr, and evaporation to afford 2-(2-chloro-4-methoxyphenyl)-2H-indazol-5-yl acetate (455 mg). $^1$H NMR (500 MHz, CDCl$_3$) δ 2.36 (s, 3H), 3.90 (s, 3H), 6.97 (dd, J=3.0, 8.5 Hz, 1H), 7.08 (dd, J=8.5, 3.0 Hz, 1H), 7.10 (d, J=3.0 Hz, 1H), 7.44 (d, J=3.0 Hz, 1H), 7.56 (d, J=8.5 Hz, 1H), 7.80 (d, J=8.5 Hz, 1H), 8.24 (s, 1H). $^{13}$C NMR (126 MHz, CDCl$_3$) δ 21.45, 56.17, 111.26, 113.73, 115.68, 119.53, 121.56, 123.22, 126.07, 129.36, 130.32, 131.93, 145.97, 147.70, 160.56, 170.27. HRMS (ESI, M$^+$+1) C$_{16}$H$_{14}$ClN$_2$O$_3$ Calcd. 317.0693, found 317.0681.

2-(4-acetoxy-2-chlorophenyl)-2H-indazol-5-yl acetate (5, 4'-DiAcO-Indazol-o-Cl)

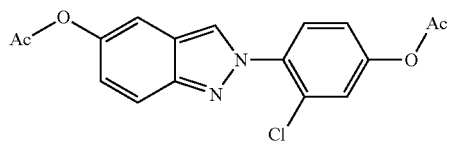 [SMILES: CC(=O)Oc1ccc(-n2cc3cc(OC(C)=O)ccc3n2)c(Cl)c1]

$^1$H NMR (500 MHz, Chloroform-d) δ 8.31 (s, 1H), 7.80 (d, J=9.0 Hz, 1H), 7.69 (d, J=9.0 Hz, 1H), 7.46 (d, J=2.4 Hz, 1H), 7.41 (d, J=2.4 Hz, 1H), 7.22 (dd, J=9.0, 2.4 Hz, 1H), 7.10 (dd, J=9.0, 2.4 Hz, 1H), 2.37 (s, 3H), 2.36 (s, 3H). $^{13}$C NMR (126 MHz, CDCl3) δ 170.19, 168.95, 151.20, 147.88, 146.13, 136.31, 129.86, 129.29, 125.96, 124.22, 123.60, 121.69, 121.43, 119.56, 111.30, 21.43, 21.31. HRMS (ESI, M$^+$+1) C$_{17}$H$_{14}$ClN$_2$O$_4$ Calcd. 345.0642, found 345.0628.

3-chloro-2-(2-chloro-4-methoxyphenyl)-2H-indazol-5-yl acetate (5-AcO-IndCl-o-Cl-4'-OMe)

To the 2-(2-chloro-4-methoxyphenyl)-2H-indazol-5-yl acetate (184 mg, 0.582 mmol) in THF (5 mL) was added NCS (80 mg, 0.60 mmol) and a catalytic amount of p-TsOH. The resulting solution was refluxed for 4 hr, allowed to cool down to room temperature and passed through short silica gel column (2.5×3 cm) with 30% ethyl acetate in n-hexane (v/v) to afford a 3-chloro-2-(2-chloro-4-methoxyphenyl)-2H-indazol-5-yl acetate (193 mg) as a colorless solid. Over the time of the chlorination, the blue fluorescent starting material spot slowly disappeared on silica gel TLC and a slightly higher Rf value of non-blue fluorescent spot appeared on TLC. $^1$H NMR (500 MHz, CDCl$_3$) δ 2.38 (s, 3H), 3.93 (s, 3H), 6.99 (dd, J=2.5, 8.5 Hz, 1H), 7.12 (dd, J=2.5, 8.5 Hz, 1H), 7.14 (d, J=3.0 Hz, 1H), 7.38 (d, J=3.0 Hz, 1H), 7.42 (d, J=8.5 Hz, 1H), 7.74 (d, J=8.5 Hz, 1H). $^{13}$C NMR (126 MHz, CDCl3) δ 21.41, 56.19, 110.04, 113.58, 115.54, 118.52, 120.15, 123.45, 124.28, 128.65, 130.23, 133.28, 146.31, 147.23, 161.54, 170.14.

Scheme 5

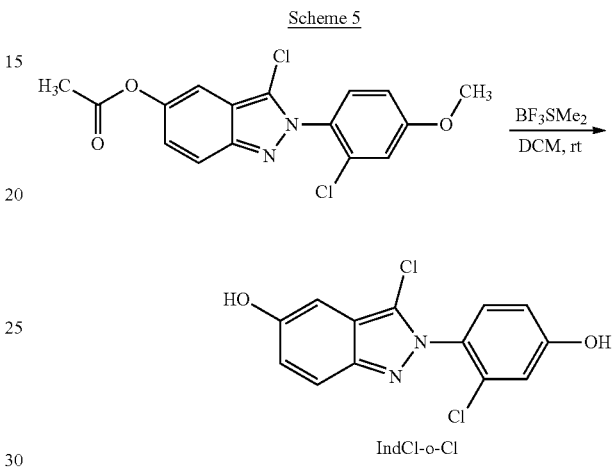

3-chloro-2-(2-chloro-4-hydroxyphenyl)-2H-indazol-5-ol (IndCl-o-Cl)

3-Chloro-2-(2-chloro-4-methoxyphenyl)-2H-indazol-5-yl acetate (193 mg, 0.50 mmol) was dissolved into dichloromethane (5 ml). Boron trifluoride dimethyl sulfide (700 mg, 5.38 mmol) was added to the resulting solution and the reaction vessel was stirred for 4 hr at rt. Once the starting material had disappeared, as determined by silica gel TLC analysis, the solvent and excess boron trifluoride dimethyl sulfide were evaporated. Deionized water (5 mL) was added to the residue, and the mixture was sonicated for 20 min to form a precipitate. The colorless solid was collected by filtration and dried to afford the title compound, IndCl-o-Cl (162 mg). $^1$H NMR (500 MHz, CD$_3$OD-CDCl$_3$) δ 6.76 (d, J=3.0 Hz, 1H), 6.79 (dd, J=2.5, 8.5 Hz, 1H), 6.95 (d, J=2.5 Hz, 1H), 7.00 (dd, J=2.5, 8.5 Hz, 1H), 7.21 (d, J=8.5 Hz, 1H), 7.47 (d, J=8.5 Hz, 1H). $^{13}$C NMR (126 MHz, CD$_3$OD-CDCl$_3$) δ 98.41, 114.77, 116.94, 119.08, 119.23, 120.88, 122.99, 127.51, 130.12, 132.95, 145.23, 152.64, 159.67. HRMS (ESI, M$^+$+1) C$_{13}$H$_9$C$_2$N$_2$O$_2$ Calcd. 295.0041, found 295.0051.

B. Synthesis of 3-chloro-2-(4-hydroxy-2-methylphenyl)-2H-indazol-5-ol (IndCl-o-Me)

3-(hydroxymethyl)-4-((4-methoxy-2-methylphenyl)diazenyl)phenol (Azo-o-Me)

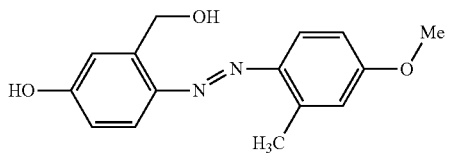

Azo-o-Me was obtained from the reaction with p-methoxy-2-methylaniline (1.37 g, 10.00 mmol), $NaNO_2$ (700.00 mg, 10.14 mmol), and 3-hydroxybenzyl alcohol (1.24 g, 10.00 mmol) in 89% yield as a yellowish solid, following an analogous procedure as described to make Azo-o-Cl compound. $^1$H NMR (500 MHz, $CD_3OD$-$CDCl_3$) δ 2.67 (s, 3H), 3.83 (s, 3H), 4.97 (s, 2H), 6.75 (dd, J=8.5, 3.0 Hz, 1H), 6.78-6.83 (m, 2H), 6.88 (d, J=3.0 Hz, 1H), 7.54 (d, J=8.5 Hz, 1H), 7.72 (dd, J=8.5, 3.0 Hz, 1H). $^{13}$C NMR (126 MHz, $CD_3OD$-$CDCl_3$) δ 18.14, 55.66, 62.98, 112.66, 114.76, 115.50, 115.64, 117.14, 120.41, 140.26, 140.35, 144.33, 145.43, 159.75, 161.67. HRMS (ESI, M$^+$+1) $C_{15}H_{17}N_2O_2$ Calcd. 273.1239, found 273.1241.

2-(4-methoxy-2-methylphenyl)-2H-indazol-5-ol (5-Hydroxy-Indazol-o-Me-4'-OMe)

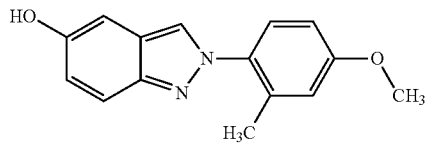 [SMILES: COc1ccc(-n2cc3cc(O)ccc3n2)c(C)c1]

$^1$H NMR (500 MHz, $CD_3OD$-$CDCl_3$) δ 2.10 (s, 3H), 3.82 (s, 3H), 6.80 (dd, J=8.5, 2.5 Hz, 1H), 6.83 (d, J=2.5 Hz, 1H), 6.92 (d, J=2.5 Hz, 1H), 7.00 (dd, J=8.5, 2.5 Hz, 1H), 7.26 (d, J=8.5 Hz, 1H), 7.55 (d, J=8.5 Hz, 1H), 7.83 (s, 1H). $^{13}$C NMR (126 MHz, $CD_3OD$-$CDCl_3$) δ 21.69, 59.54, 104.03, 115.73, 120.12, 122.26, 125.30, 125.42, 127.90, 131.81, 137.40, 139.83, 149.57, 156.02, 164.10. HRMS (ESI, M$^+$+1) $C_{15}H_{15}N_2O_2$ Calcd. 255.1134, found 255.1140.

2-(4-methoxy-2-methylphenyl)-2H-indazol-5-yl acetate (5-Ac-Indazole-o-Me-4'-OMe)

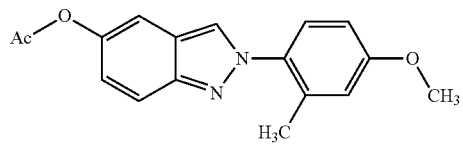

$^1$H NMR (500 MHz, $CDCl_3$) δ 2.21 (s, 3H), 2.37 (s, 3H), 3.89 (s, 3H), 6.86 (dd, J=3.0, 8.5 Hz, 1H), 6.90 (d, J=2.5 Hz, 1H), 6.92 (d, J=3.0 Hz, 1H), 7.09 (dd, J=8.5, 3.0 Hz, 1H), 7.35 (d, J=8.5 Hz, 1H), 7.45 (d, J=3.0 Hz, 1H), 7.81 (d, J=8.5 Hz, 1H), 8.06 (s, 1H). $^{13}$C NMR (126 MHz, $CDCl_3$) δ 18.24, 21.47, 55.81, 111.16, 111.88, 116.40, 119.54, 121.54, 122.65, 125.20, 125.35, 127.93, 133.75, 135.74, 145.82, 147.60, 160.19, 170.33. HRMS (ESI, M$^+$+1) $C_{17}H_{17}N_2O_3$ Calcd. 297.1239, found 297.1243.

2-(4-acetoxy-2-methylphenyl)-2H-indazol-5-yl acetate (5, 4'-DiAc-Indazole-o-Me)

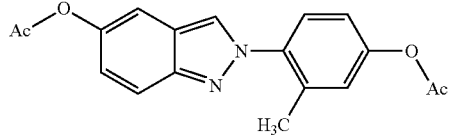 [SMILES: CC(=O)Oc1ccc(-n2cc3cc(OC(C)=O)ccc3n2)c(C)c1]

$^1$H NMR (499 MHz, Chloroform-d) δ 8.06 (s, 1H), 7.81 (d, J=9.2 Hz, 1H), 7.45 (d, J=2.1 Hz, 1H), 7.35 (d, J=8.6 Hz, 1H), 7.09 (dd, J=9.2, 2.1 Hz, 1H), 6.90 (d, J=2.6 Hz, 1H), 6.87 (dd, J=8.7, 2.9 Hz, 1H), 3.89 (s, 3H), 2.37 (s, 3H), 2.21 (s, 3H). $^{13}$C NMR (126 MHz, $CDCl_3$) δ 170.33, 160.19, 147.60, 145.82, 135.74, 133.75, 127.93, 125.35, 125.20, 122.62, 121.54, 119.54, 116.40, 111.88, 111.16, 55.81, 21.47, 18.24. HRMS (ESI, M$^+$+1) $C_{18}H_{17}N_2O_4$ Calcd. 325.1188, found 325.1191.

3-chloro-2-(4-hydroxy-2-methylphenyl)-2H-indazol-5-ol (IndCl-o-Me)

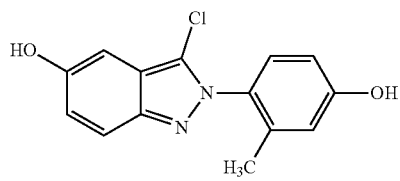

IndCl-o-Me was obtained from the reaction of 2-methyl-4-methoxyaniline (411 mg, 3.00 mmol) with 3-hydroxymethylphenol (397 mg, 3.20 mmol) in 63% yield through 5 steps, following an analogous procedure as described for the preparation of IndCl-o-Cl. $^1$H NMR (500 MHz, $CD_3OD$-$CDCl_3$) δ 1.93 (s, 3H), 6.73 (dd, J=2.5, 8.5 Hz, 1H), 6.76 (d, J=2.5 Hz, 1H), 6.78 (d, J=2.5 Hz, 1H), 7.01 (dd, J=2.5, 8.5 Hz, 1H), 7.10 (d, J=8.5 Hz, 1H), 7.50 (d, J=8.5 Hz, 1H). $^{13}$C NMR (126 MHz, $CD_3OD$-$CDCl_3$) δ 17.09, 98.36, 113.44, 117.27, 118.87, 119.24, 120.15, 122.57, 128.82, 129.28, 137.43, 144.84, 152.69, 158.69. HRMS (ESI, M$^+$+1) $C_{14}H_{12}ClN_2O_2$ Calcd. 275.0587, found 275.0587.

C. Synthesis of 3-chloro-2-(4-hydroxy-2-(trifluoromethyl)phenyl)-2H-indazol-5-ol (IndCl-o-CF$_3$)

3-chloro-2-(4-hydroxy-2-(trifluoromethyl)phenyl)-2H-indazol-5-ol (IndCl-o-CF$_3$)

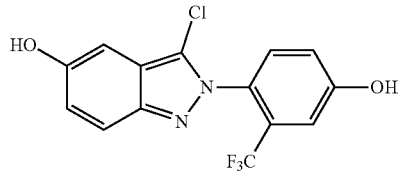 [SMILES: Oc1ccc(-n2nc3ccc(O)cc3c2Cl)c(C(F)(F)F)c1]

IndCl-o-CF₃ was prepared from the reaction of 2-trifluoromethyl-4-methoxyaniline (382 mg, 2.00 mmol) with 3-hydroxymethylphenol (272 mg, 2.20 mmol) in 71% yield through 5 steps, following an analogous procedure as described to prepare IndCl-o-Cl. ¹H NMR (500 MHz, CD₃OD-CDCl₃) δ 6.77 (dd, J=2.5, 8.5 Hz, 1H), 7.02-7.033 (m, 2H), 7.19-7.24 (m, 2H), 7.50 (dd, J=2.5, 8.5 Hz, 1H). ¹⁹FNMR (470 MHz, CD₃OD-CDCl₃) δ −61. ¹³C NMR (126 MHz, CD₃OD-CDCl₃) δ 98.36, 114.46 (J=4.6 Hz), 118.99, 119.16, 122.65 (J=259 Hz), 123.29, 126.38, 129.26 (J=32.38 Hz), 131.71, 140.05, 142.63, 144.85, 152.79, 159.36. HRMS (ESI, M⁺+1) C₁₄H₇ClN₂O₂F₃ Calcd. 327.0148, found 327.0143.

D. Synthesis of 3-chloro-2-(2-fluoro-4-hydroxyphenyl)-2H-indazol-5-ol (IndCl-o-F)

3-chloro-2-(2-fluoro-4-hydroxyphenyl)-2H-indazol-5-ol (IndCl-o-F)

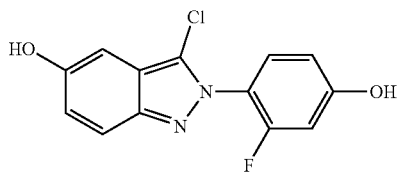

IndCl-o-F was prepared from the reaction of 2-fluoro-4-methoxyaniline (282 mg, 2.00 mmol) with 3-hydroxymethylphenol (272 mg, 2.20 mmol) in 68% yield through 5 steps, following an analogous procedure as described to prepare IndCl-o-Cl. ¹H NMR (500 MHz, CD₃OD-CDCl₃) δ 6.67-6.72 (m, 2H), 6.77 (d, J=2.5 Hz, 1H), 7.01 (dd, J=2.5, 8.5 Hz, 1H), 7.25 (t, J=9.0 Hz, 1H), 7.48 (d, J=8.5 Hz, 1H). ¹⁹F NMR (470 MHz, CD₃OD-CDCl₃) δ −120.09 (t, J=38.1 Hz, 1H). ¹³C NMR (126 MHz, CD₃OD-CDCl₃) δ 98.36, 103.83 (J=22.18 Hz), 111.93, 117.65 (J=7.4 Hz), 118.96, 119.46, 120.89, 123.10, 129.49, 145.22, 125.71, 156.81, 159.11 9J=259.11 Hz). HRMS (ESI, M⁺+1) C₁₃H₇ClN₂O₂F Calcd. 277.0189, found 277.0176.

E. Synthesis of 2-(2-bromo-4-hydroxyphenyl)-3-chloro-2H-indazol-5-ol (IndCl-o-Br)

(E)-4-((2-bromo-4-methoxyphenyl)diazenyl)-3-(hydroxymethyl)phenol (Azo-o-Br)

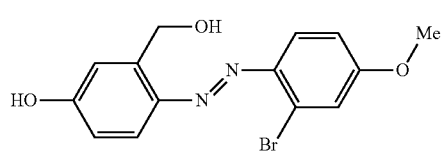

Azo-o-Br was obtained from the reaction with p-methoxy-2-bromoaniline (808.00 mg, 4.00 mmol), NaNO₂ (284.00 mg, 4.12 mmol), and 3-hydroxybenzyl alcohol (496 mg, 4.00 mmol) in 94% yield as yellowish solid following an analogous procedure as described to prepare Azo-o-Cl compound. ¹H NMR (500 MHz, CD₃OD-CDCl₃) δ 3.83 (s, 3H), 4.90 (s, 2H), 6.82 (dd, J=8.5, 2.5 Hz, 1H), 6.86 (dd, J=9.0, 2.5 Hz, 1H), 6.89 (d, J=2.5 Hz, 1H), 7.21 (d, J=2.5 Hz, 1H), 7.59 (d, J=9.0 Hz, 1H), 7.79 (d, J=9.0 Hz, 1H). ¹³C NMR (126 MHz, CD₃OD-CDCl₃) δ 55.04, 62.55, 114.74, 115.31, 115.59, 118.01, 118.84, 123.80, 126.81, 139.70, 143.99, 144.19, 160.49, 161.82. HRMS (ESI, M⁺+1) C₁₄H₁₄BrN₂O₃ Calcd. 337.0188, found 337.0174.

2-(2-bromo-4-methoxyphenyl)-2H-indazol-5-ol (5-OH-Indazol-o-Br-4-OMe)

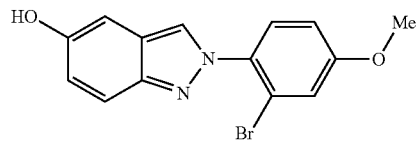 [SMILES: COc1ccc(-n2cc3cc(O)ccc3n2)c(Br)c1]

5-OH-Indazol-o-Br-4-methoxy was prepared quantitatively from the cyclization with Azo-o-Br (336.00 mg, 1.00 mmol) following the procedure of Method 1 to form the indazole ring. ¹H NMR (500 MHz, CDCl₃+CD₃OD) δ 3.85 (s, 3H), 6.94 (d, J=2.5 Hz, 1H), 6.95 (dd, J=8.5, 2.5 Hz, 1H), 7.02 (dd, J=9.0, 2.5 Hz, 1H), 7.23 (d, J=2.5 Hz, 1H), 7.43 (d, J=8.5 Hz, 1H), 7.80 (d, J=9.0 Hz, 1H), 7.95 (s, 1H). ¹³C NMR (126 MHz, CDCl₃+CD₃OD) δ 56.07, 100.04, 114.01, 118.65, 118.75, 120.16, 121.81, 122.39, 124.41, 129.39, 133.41, 145.93, 125.13, 160.58. HRMS (ESI, M⁺+1) C₁₄H₁₂BrN₂O₂ Calcd. 319.0082, found 319.0073.

2-(2-bromo-4-methoxyphenyl)-2H-indazol-5-yl acetate (5-Ac-Indazol-o-Br-4'-OMe)

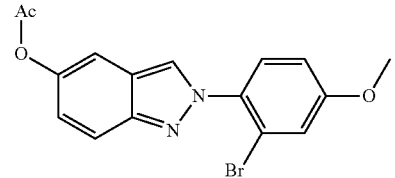 [SMILES: COc1ccc(-n2cc3cc(OC(C)=O)ccc3n2)c(Br)c1]

¹H NMR (500 MHz, CDCl₃) δ 2.36 (s, 3H), 3.89 (s, 3H), 7.00 (dd, J=3.0, 9.0 Hz, 1H), 7.08 (dd, J=9.0, 3.0 Hz, 1H), 7.27 (d, J=2.5 Hz, 1H), 7.45 (d, J=2.5 Hz, 1H), 7.49 (d, J=9.0 Hz, 1H), 7.80 (d, J=9.0 Hz, 1H), 8.20 (s, 1H). 13C NMR (126 MHz, CDCl₃) δ 21.45, 56.19, 111.28, 114.20, 118.71, 119.57, 119.98, 121.49, 123.19, 126.10, 129.49, 133.58, 145.99, 147.70, 160.68, 170.26. HRMS (ESI, M⁺+1) C₁₆H₁₄BrN₂O₃ Calcd. 361.0188, found 361.0192.

2-(4-acetoxy-2-bromophenyl)-2H-indazol-5-yl acetate (5, 4'-Di-Ac-Indazol-o-Br)

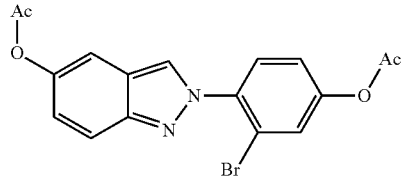

¹H NMR (500 MHz, Chloroform-d) δ 8.27 (s, 1H), 7.80 (d, J=9.3 Hz, 1H), 7.62 (d, J=8.6 Hz, 1H), 7.57 (d, J=2.3 Hz, 1H), 7.46 (d, J=2.0 Hz, 1H), 7.26 (dd, J=8.6, 2.4 Hz, 1H), 7.10 (dd, J=8.6, 2.4 Hz, 1H), 2.36 (s, 6H). $^{13}$C NMR (126 MHz, CDCl$_3$) δ 170.21, 168.96, 151.37, 147.87, 146.14, 137.97, 129.48, 127.19, 125.96, 123.55, 121.92, 121.60, 119.60, 119.41, 111.32, 21.43, 21.30. HRMS (ESI, M$^+$+1) C$_{17}$H$_{14}$BrN$_2$O$_4$ Calcd. 389.0137, found 389.0132.

2-(2-bromo-4-hydroxyphenyl)-3-chloro-2H-indazol-5-ol (IndCl-o-Br)

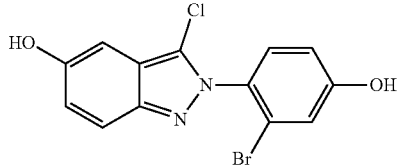

IndCl-o-Br was prepared from the reaction of 2-bromo-4-methoxyaniline (404 mg, 2.00 mmol) with 3-hydroxymethylphenol (272 mg, 2.20 mmol) in 56% yield through 5 steps, following an analogous procedure as described to prepare IndCl-o-Cl. $^1$H NMR (500 MHz, CD$_3$OD-CDCl$_3$) δ 6.79 (d, J=3.0 Hz, 1H), 6.84 (dd, J=3.0, 8.5 Hz, 1H), 7.04 (dd, J=3.0, 8.5 Hz, 1H), 7.14 (d, J=3.0 Hz, 1H), 7.23 (d, J=8.5 Hz, 1H), 7.51 (d, J=8.5 Hz, 1H). $^{13}$C NMR (126 MHz, CD$_3$OD-CDCl$_3$) δ 98.55, 115.38, 119.03, 119.27, 120.09, 121.11, 122.43, 123.24, 128.95, 130.13, 144.84, 152.74, 159.71. HRMS (ESI, M$^+$+1) C$_{13}$H$_9$ClBrN$_2$O$_2$ Calcd. 338.9536, found 338.9549.

F. Synthesis of 2-(2-iodo-4-hydroxyphenyl)-3-chloro-2H-indazol-5-ol (IndCl-o-I)

(E)-3-(hydroxymethyl)-4-((2-iodo-4-methoxyphenyl)diazenyl)phenol (Azo-o-I)

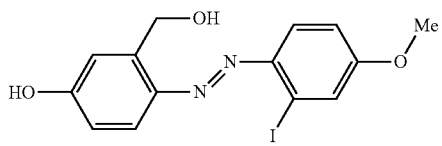 [SMILES: COc1ccc(/N=N/c2ccc(O)cc2CO)c(I)c1]

Azo-o-Me was obtained from the reaction with p-methoxy-2-iodoaniline (500 mg, 2.00 mmol), NaNO$_2$ (142.00 mg, 2.06 mmol), and 3-hydroxybenzyl alcohol (249 mg, 2.01 mmol) in 91% yield as yellowish solid following an analogous procedure as described to prepare Azo-o-Cl compound. $^1$H NMR (500 MHz, CD$_3$OD-CDCl$_3$) δ 3.83 (s, 3H), 5.00 (s, 2H), 6.79 (dd, J=9.0, 2.5 Hz, 1H), 6.90 (dd, J=9.0, 2.5 Hz, 1H), 6.91 (d, J=2.5 Hz, 1H), 7.46 (d, J=2.5 Hz, 1H), 7.49 (d, J=9.0 Hz, 1H), 7.78 (d, J=9.0 Hz, 1H). $^{13}$C NMR (126 MHz, CD$_3$OD-CDCl$_3$) δ 55.97, 62.10, 103.98, 114.55, 115.50, 115.56, 118.06, 121.22, 124.00, 141.20, 143.33, 145.99, 160.59, 161.74.

2-(2-iodo-4-methoxyphenyl)-2H-indazol-5-yl acetate (5-Ac-Indazol-o-I-4'-OMe)

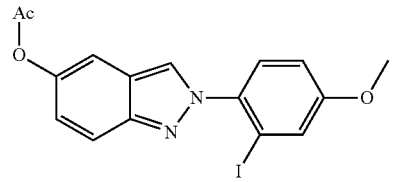 [SMILES: COc1ccc(-n2cc3cc(OC(C)=O)ccc3n2)c(I)c1]

$^1$H NMR (500 MHz, CDCl$_3$) δ 2.35 (s, 3H), 3.87 (s, 3H), 7.01 (dd, J=8.5, 2.5 Hz, 1H), 7.08 (dd, J=8.5, 2.5 Hz, 1H), 7.37 (d, J=8.5 Hz, 1H), 7.45 (d, J=2.5 Hz, 1H), 7.49 (d, J=2.5 Hz, 1H), 7.80 (d, J=8.5 Hz, 1H), 8.13 (s, 1H). $^{13}$C NMR (126 MHz, CDCl$_3$) δ 21.47, 56.15, 94.94, 111.31, 114.79, 119.61, 121.52, 123.14, 124.88, 125.93, 128.72, 137.15, 145.98, 147.65, 160.56, 170.27.

2-(4-acetoxy-2-iodophenyl)-2H-indazol-5-yl acetate (5,4'-diAc-Indazol-o-I)

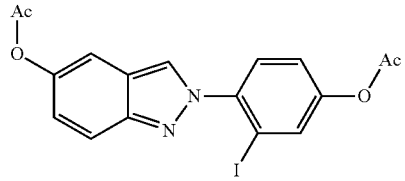

$^1$H NMR (500 MHz, Chloroform-d) δ 8.18 (s, 1H), 7.81 (d, J=9.3 Hz, 1H), 7.77 (s, 1H), 7.50 (d, J=9.0 Hz, 1H), 7.46 (s, 1H), 7.28 (d, J=9.0 Hz, 1H), 7.11 (d, J=9.3 Hz, 1H), 2.36 (s, 3H), 2.35 (s, 3H). $^{13}$C NMR (126 MHz, CDCl$_3$) δ 170.19, 168.95, 151.20, 147.88, 146.13, 136.31, 129.86, 129.29, 125.96, 124.22, 123.60, 121.69, 121.43, 119.56, 111.30, 21.43, 21.31. HRMS (ESI, M$^+$+1) C$_{17}$H$_{14}$IN$_2$O$_4$ Calcd. 436.9987, found 436.9989.

2-(2-iodo-4-hydroxyphenyl)-3-chloro-2H-indazol-5-ol (IndCl-o-I)

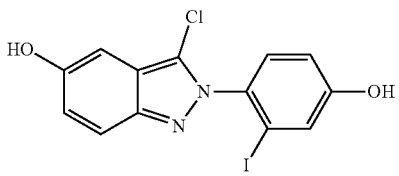

IndCl-o-I was prepared from the reaction of 2-iodo-4-methoxyaniline (500 mg, 2.00 mmol) with 3-hydroxymethylphenol (272 mg, 2.20 mmol) in 51% yield through 5 steps, following an analogous procedure as described to prepare IndCl-o-Cl. $^1$H NMR (500 MHz, CD$_3$OD-CDCl$_3$) δ 6.78 (d, J=3.0 Hz, 1H), 6.87 (dd, J=3.0, 8.5 Hz, 1H), 7.02 (dd, J=3.0, 8.5 Hz, 1H), 7.17 (d, J=8.5 Hz, 1H), 7.37 (d, J=3.0 Hz, 1H), 7.50 (d, J=8.5 Hz, 1H). $^{13}$C NMR (126 MHz, CD$_3$OD-CDCl$_3$) δ 97.07, 98.52, 116.05, 119.22, 119.44, 120.42, 123.02, 126.19, 129.36, 132.82, 145.01, 152.65, 159.26. HRMS (ESI, M$^+$+1) C$_{13}$H$_9$ClN$_2$O$_2$ Calcd. 386.9397, found 386.9379.

G. Synthesis of 4-(3-chloro-5-hydroxy-2H-indazol-2-yl)benzene-1,3-diol (IndCl-o-OH)

Scheme 6

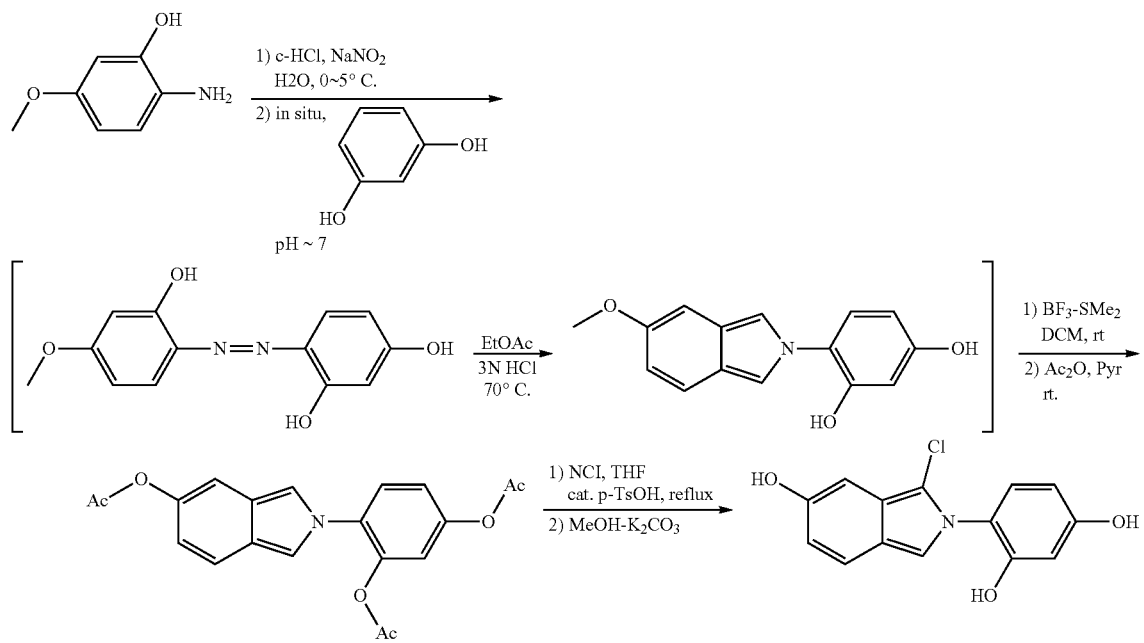

IndCl-o-OH was prepared as shown in Scheme 6.

4-(5-acetoxy-2H-indazol-2-yl)-1,3-phenylene diacetate (Ind-TriOAc)

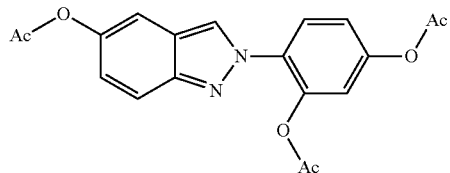

To a suspension of o-hydroxymethyl-p-anisidine (183 mg, 1.0 mmol) in cold deionized water (5 mL) was added c-HCl (0.3 mL). Subsequently sodium nitrite (82 mg, 1.20 mmol) was added in portions while the reaction was in an ice bath to maintain the temperature below 5° C. After 1.5 hr stirring the reaction mixture at below 5° C., resorcinol (110 mg, 1.00 mmol) in a water-acetone (1:1, v/v, 2 ml) mixture was added into the reaction mixture in ice bath, followed by adjusting the pH up to 7.5 with 1N NaOH to precipitate a yellowish solid. During the addition of the NaOH aq. solution, a massive yellowish solid precipitated from solution as the pH reached ~7.5. The solution was extracted with EtOAc (20 ml×3), followed by adding 3 N HCl (1 mL), refluxing the solution for 5 hr, and chromatography on SiO$_2$ column with 30% ethyl acetate in n-Hexane to afford a 4-(5-methoxy-2H-indazol-2-yl)benzene-1,3-diol (155 mg) as a colorless powder. Treatment of 4-(5-methoxy-2H-indazol-2-yl)benzene-1,3-diol (120 mg, 0.47 mmol) with BF$_3$—SMe$_2$ (5 mL) in DCM at rt and subsequently treatment with Ac$_2$O (0.5 mL) and pyridine (0.3 mL) afforded a 4-(5-acetoxy-2H-indazol-2-yl)-1,3-phenylene diacetate (Ind-TriOAc) (170 mg). $^1$H NMR (500 MHz, CDCl$_3$) δ 2.18, (s, 3H), 2.35 (s, 3H), 2.36 (s, 3H), 7.08 (dd, J=9.5, 2.0 Hz, 1H), 7.17 (d, J=2.5 Hz, 1H), 7.21 (dd, J=9.0, 2.5 Hz, 1H), 7.43 (d, J=2.0 Hz, 1H), 7.73 (d, J=9.0 Hz, 1H), 7.78 (d, J=9.5 Hz, 1H). $^{13}$C NMR (126 MHz, CDCl$_3$) δ 21.01, 21.37, 21.43, 111.20, 118.04, 119.56, 120.27, 121.88, 123.49, 124.73, 127.36, 131.10, 144.38, 146.14, 148.02, 151.01, 168.44, 168.96, 170.24.

4-(3-chloro-5-hydroxy-2H-indazol-2-yl)benzene-1,3-diol (IndCl-o-OH)

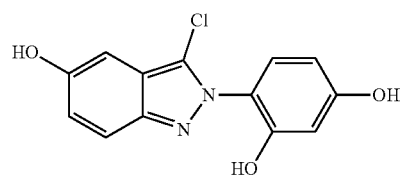

IndCl-o-OH was prepared from the reaction of Ind-TriOAc (100 mg, 2.7 mmol) with NCS (43 mg, 3.26 mmol) and a catalytic amount of p-TsOH in THF at 75° C. After 6 hr refluxing, the starting material disappeared completely. Evaporation of solvent, dissolving the resultant into MeOH (5 mL) over K$_2$CO$_3$ (200 mg), and column chromatography on SiO$_2$ with 30% ethyl acetate in n-Hexane provided IndCl-o-OH (56 mg). $^1$H NMR (500 MHz, CDCl$_3$+CD$_3$OD) δ 6.43 (dd, J=8.5, 1.5 Hz, 1H), 6.51 (d, J=2.0 Hz, 1H), 6.81 (d, J=2.0 Hz, 1H), 7.05 (dd, J=8.5, 1.5 Hz, 1H), 7.51 (d, J=8.5 Hz, 1H), 7.45 (d, J=8.5 Hz, 1H). $^{13}$C NMR (126 MHz, CDCl$_3$+CD$_3$OD) δ 98.78, 104.06, 107.43, 117.18, 118.34, 119.83, 123.30, 125.45, 127.74, 143.99, 152.82, 153.15, 159.52. HRMS (ESI, M$^+$+1, pos. mode) C$_{13}$H$_{10}$ClN$_2$O$_3$ Calcd. 277.0380, found 277.0381.

H. Synthesis of 2-(2-chloro-4-hydroxyphenyl)-3,4-dichloro-2H-indazol-5-ol (IndCl-o-Cl-4-Cl)

2-(2-chloro-4-hydroxyphenyl)-3,4-dichloro-2H-indazol-5-ol (IndCl-o-Cl-4-Cl)

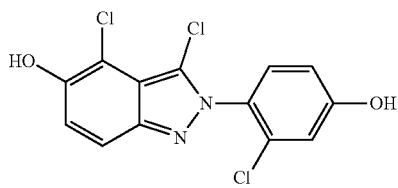

IndCl-o-Cl-4-Cl was prepared from the reaction of IndCl-o-Cl (29.4 mg, 0.10 mmol) with NCS (26.0 mg, 0.20 mmol) in THF (1.0 mL) containing a catalytic amount of p-TsOH at 45° C. in 67% yield (22.0 mg) as a pale grey solid after silica gel chromatographic purification with a mixture of methanol and dichloromethane (5:95, v/v) as an eluent. $^1$H NMR (500 MHz, CD$_3$OD-CDCl$_3$) δ 6.85 (dd, J=2.5, 9.0 Hz, 1H), 7.00 (d, J=2.5 Hz, 1H), 7.09 (d, J=9.0 Hz, 1H), 7.24 (d, J=8.5 Hz, 1H), 7.41 (d, J=8.5 Hz, 1H). 13C NMR (126 MHz, CD$_3$OD-CDCl$_3$) δ 105.34, 114.80, 116.60, 116.91, 117.58, 121.65, 122.59, 127.24, 130.16, 132.99, 145.63, 148.49, 159.96. HRMS (ESI, M$^+$−1, neg. mode) C$_{13}$H$_6$C$_{13}$N$_2$O$_2$ Calcd. 326.9495, found 326.9488.

I. Synthesis of 3,4-Dichloro-2-(2,6-difluoro-4-hydroxyphenyl)-2H-indazol-5-ol (IndCl-4-Cl-o-diF) and 2-(2,6-difluoro-4-hydroxyphenyl)-2H-indazol-5-ol (Ind-o-diF)

Scheme 7

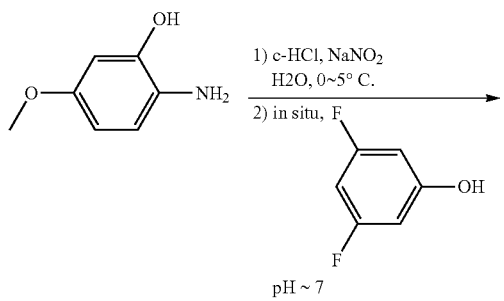

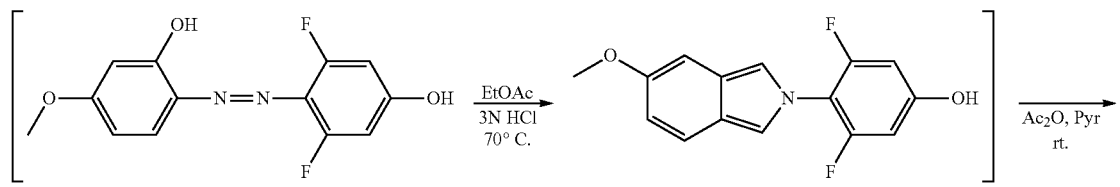

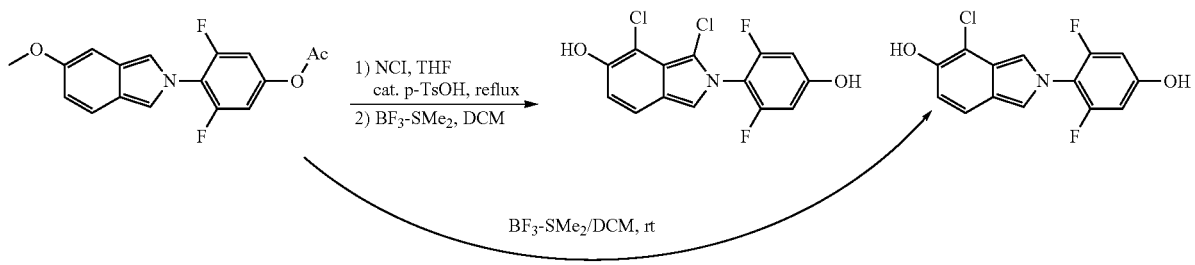

IndCl-7-Cl-o-diF was prepared from the reaction of o-hydroxymethyl-p-anisidine (183 mg, 1.0 mmol) with 3,5-difluorophenol (130 mg, 1.00 mmol) in 45% yield through 5 steps, following the same procedure described for the preparation of IndCl-o-Cl, except to use 2.2 eq. of NCI.

3,5-difluoro-4-(5-methoxy-2H-indazol-2-yl)phenyl acetate

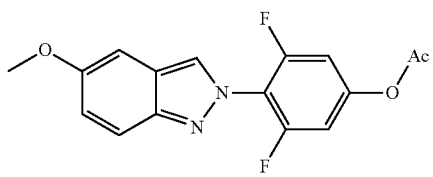 [SMILES: COc1ccc2nn(-c3c(F)cc(O)cc3F)cc2c1 ; "Ac"]

$^1$H NMR (500 MHz, CDCl$_3$) δ 2.35 (s, 3H), 3.86 (s, 3H), 6.92 (d, J=2.0 Hz, 1H), 6.98 (d, J=8.5 Hz, 2H), 7.08 (dd, J=9.5, 2.5 Hz, 1H), 7.70 (d, J=9.5 Hz, 1H), 8.03 (s, 1H). $^{19}$F NMR (470 MHz, CDCl$_3$) δ −118.25 (d, J=8.9 Hz). $^{13}$C NMR (126 MHz, CDCl$_3$) δ 21.29, 55.60, 96.17, 107.08 (dd, J=23.9, 3.6 Hz), 117.09, 119.55, 122.22, 123.00, 125.35, 147.26, 151.44 (t, J=13.1 Hz), 155.86, 155.62 (dd, J=256.3, 5.2 Hz), 168.48.

3,4-dichloro-2-(2,6-difluoro-4-hydroxyphenyl)-2H-indazol-5-ol (IndCl-4-Cl-o-diF)

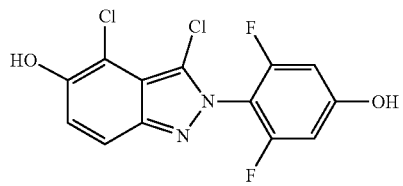 [SMILES: Oc1cc(F)c(-n2nc3ccc(O)c(Cl)c3c2Cl)c(F)c1]

$^1$H NMR (500 MHz, CDCl$_3$+CD$_3$OD) δ 6.53 (d, J=9.5 Hz, 2H), 7.07 (d, J=9.3 Hz, 1H), 7.42 (d, J=9.3 Hz, 1H). $^{19}$F NMR (470 MHz, CDCl$_3$) δ −119.33 (d, J=11.3 Hz). $^{13}$C NMR (126 MHz, CDCl$_3$) δ 100.25 (d, J=24.9 Hz), 105.07, 106.99, 116.45, 118.00, 122.25, 122.61, 146.48, 148.31, 157.41, 159.00 (d, J=253.9 Hz). HRMS (ESI, M$^+$−1, neg. mode) C$_{13}$H$_5$F$_2$C$_2$N$_2$O$_2$ Calcd. 328.9696, found 328.9693.

2-(2,6-difluoro-4-hydroxyphenyl)-2H-indazol-5-ol (Ind-o-diF)

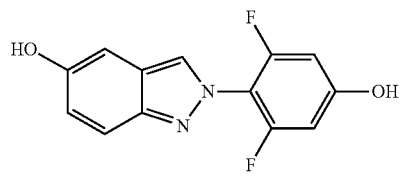 [SMILES: Oc1cc(F)c(-n2cc3cc(O)ccc3n2)c(F)c1]

$^1$H NMR (499 MHz, Methanol-d$_4$) δ 6.55 (d, J=9.6 Hz, 2H), 6.94 (dd, J=2.3, 0.8 Hz, 1H), 7.03 (dd, J=9.3, 2.3 Hz, 1H), 7.55 (dt, J=9.3, 0.9 Hz, 1H), 7.94 (s, 1H). $^{19}$F NMR (470 MHz, CDCl$_3$) δ −121.66 (d, J=10.15 Hz). $^{13}$C NMR (126 MHz, CDCl$_3$) δ 99.78 (d, J=22.68 Hz), 99.85, 118.21, 122.30, 122.48, 125.75, 146.21, 152.30, 158.52 (d, J=252.5 Hz), 160.06, 160.17.

J. Synthesis of 3,4-dichloro-2-(2,6-dichloro-4-hydroxyphenyl)-2H-indazol-5-ol (IndCl-4-Cl-o-Cl2)

IndCl-4-Cl-o-diCl was prepared from the reaction of o-hydroxymethyl-p-anisidine (183 mg, 1.0 mmol) with 3,5-dichlorophenol (161 mg, 1.00 mmol) in 58% yield through 5 steps, following an analogous procedure as described to prepare IndCl-4-Cl-o-diF.

3,5-dichloro-4-(5-methoxy-2H-indazol-2-yl)phenyl acetate

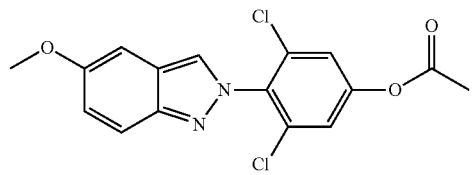 [SMILES: COc1ccc2nn(-c3c(Cl)cc(OC(C)=O)cc3Cl)cc2c1]

$^1$H NMR (500 MHz, CDCl$_3$) δ 2.37 (s, 3H), 3.88 (s, 3H), 6.96 (d, J=2.0 Hz, 1H), 7.09 (dd, J=9.5, 2.0 Hz, 1H), 7.33 (s, 2H), 7.72 (d, J=9.5 Hz, 1H), 7.95 (s, 1H). $^{13}$C NMR (126 MHz, CDCl$_3$) δ 21.26, 55.61, 96.42, 119.12, 119.78, 122.12, 122.50, 122.74, 124.67, 134.92, 146.94, 151.42, 155.88, 168.58.

3,5-dichloro-4-(3,4-dichloro-5-methoxy-2H-indazol-2-yl)phenyl acetate

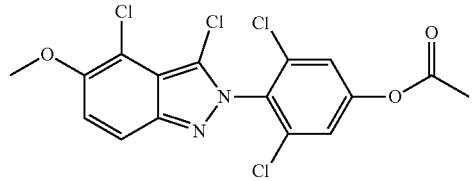 [SMILES: COc1ccc2nn(-c3c(Cl)cc(OC(C)=O)cc3Cl)c(Cl)c2c1Cl]

$^1$H NMR (500 MHz, CDCl$_3$) δ 2.38 (s, 3H), 4.02 (s, 3H), 7.28 (s, 2H), 7.29 (d, J=9.5 Hz, 1H), 7.67 (d, J=9.5 Hz, 1H).

3,4-dichloro-2-(2,6-dichloro-4-hydroxyphenyl)-2H-indazol-5-ol (IndCl-4-Cl-o-diCl)

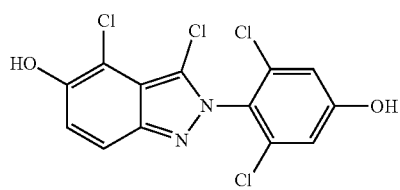 [SMILES: Oc1cc(Cl)c(-n2nc3ccc(O)c(Cl)c3c2Cl)c(Cl)c1]

$^1$H NMR (500 MHz, CDCl$_3$+CD$_3$OD) δ 6.95 (s, 2H), 7.2 (d, J=9.5 Hz, 1H), 7.51 (d, J=9.5 Hz, 1H). $^{13}$C NMR (126 MHz, CDCl$_3$) δ 105.11, 115.64, 115.96, 116.17, 118.55, 121.62, 122.25, 135.05, 146.32, 148.13, 159.84. HRMS (ESI, M⁺−1, neg. mode) $C_{13}H_5Cl_4N_2O_2$ Calcd. 360.9105, found 360.9103.

K. Synthesis of 2-(2,6-dichloro-4-hydroxyphenyl)-2H-indazol-5-ol (Ind-o-diCl)

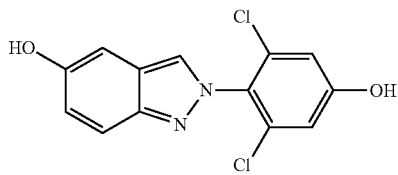 [SMILES: Oc1cc(Cl)c(-n2cc3cc(O)ccc3n2)c(Cl)c1]

2-(2,6-dichloro-4-hydroxyphenyl)-2H-indazol-5-ol (Ind-o-diCl) may be prepared according to procedures described herein. $^1$H NMR (500 MHz, Chloroform-d+CD$_3$OD) δ 7.79 (s, 1H), 7.58 (d, J=9.1 Hz, 1H), 7.01 (dd, J=9.3, 2.2 Hz, 1H), 6.93 (d, J=2.2 Hz, 1H), 6.88 (s, 2H). HRMS (ESI, M+1) $C_{13}H_9C_2N_2O_2$ Calcd. 295.0041, found 295.0034.

L. Synthesis of 2-(3-chloro-5-hydroxy-2H-indazol-2-yl)-5-hydroxybenzonitrile (IndCl-o-CN)

2-(3-chloro-5-hydroxy-2H-indazol-2-yl)-5-hydroxybenzonitrile (IndCl-o-CN)

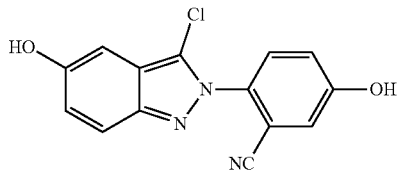

IndCl-o-CN was prepared from the reaction of 2-cyano-4-methoxyaniline (148 mg, 1.00 mmol) with 3-hydroxymethylphenol (124 mg, 1.00 mmol) in 22% yield through 5 steps, following an analogous procedure as described to prepare IndCl-o-Cl. $^1$H NMR (500 MHz, CDCl$_3$+CD$_3$OD) δ 6.79 (s, 1H), 7.05 (dd, J=8.5, 1.5 Hz, 1H), 7.17 (dd, J=8.5, 1.5 Hz, 1H), 7.23 (s, 1H), 7.40 (d, J=8.5 Hz, 1H), 7.55 (d, J=8.5 Hz, 1H).

M. Synthesis of 3-chloro-2-(3-fluoro-4-hydroxyphenyl)-2H-indazol-5-ol (IndCl-m-F)

3-chloro-2-(3-fluoro-4-hydroxyphenyl)-2H-indazol-5-ol (IndCl-m-F)

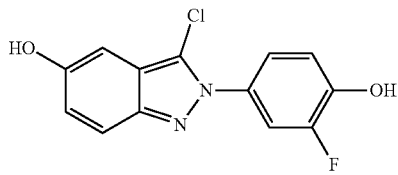

IndCl-m-F was synthesized using o-hydroxymethyl-p-anisidine (183 mg, 1.0 mmol) and o-fluorophenol (112 mg, 1.0 mmol) as starting materials, following an analogous procedure as described to prepare IndCl-o-OH. $^1$H NMR (500 MHz, CDCl$_3$+CD$_3$OD) δ 6.74 (d, J=2.5 Hz, 1H), 6.99 (dd, J=9.5, 2.5 Hz, 1H), 7.02 (d, J=8.5 Hz, 1H), 7.20 (dd, J=8.5, 2.5 Hz, 1H), 7.29 (dd, J=11.0, 2.5 Hz, 1H), 7.46 (d, J=9.5 Hz, 1H). $^{19}$F NMR (470 MHz, CD$_3$OD-CDCl$_3$) δ −135.89 (t, J=11.2 Hz, 1H). HRMS (ESI, M⁺+1) $C_{13}H_7ClN_2O_2F$ Calcd. 277.0189, found 277.0186.

N. Synthesis of 3-chloro-2-(4-hydroxy-3-methylphenyl)-2H-indazol-5-ol (IndCl-m-Me)

3-chloro-2-(4-hydroxy-3-methylphenyl)-2H-indazol-5-ol (IndCl-m-Me)

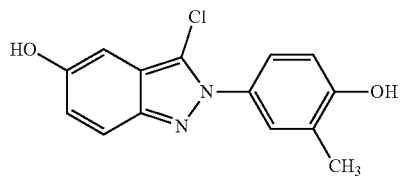 [SMILES: Cc1cc(-n2nc3ccc(O)cc3c2Cl)ccc1O]

IndCl-m-CH$_3$ was synthesized using o-hydroxymethyl-p-anisidine (183 mg, 1.0 mmol) and o-cresol (108 mg, 1.0 mmol) as starting materials, following an analogous procedure as described to prepare IndCl-o-OH. $^1$H NMR (500 MHz, CDCl$_3$+CD$_3$OD) δ 2.24 (s, 3H), 6.77 (s, 1H), 6.83 (d, J=8.5 Hz, 1H), 6.99 (dd, J=8.5, 1.5 Hz, 1H), 7.18 (d, J=8.5 Hz, 1H), 7.27 (s, 1H), 7.48 (d, J=8.5 Hz, 1H). $^{13}$C NMR (126 MHz, CDCl$_3$+CD3OD) δ 16.19, 98.49, 114.84, 118.48, 118.97, 120.07, 122.49, 124.35, 125.78, 128.26, 130.11, 144.57, 152.53, 156.16. HRMS (ESI, M⁺+1) $C_{14}H_{12}ClN_2O_2$ Calcd. 275.0587, found 275.0582.

O. Synthesis of 3-bromo-2-(2-bromo-4-hydroxyphenyl)-2H-indazol-5-ol (IndBr-o-Br)

Scheme 8

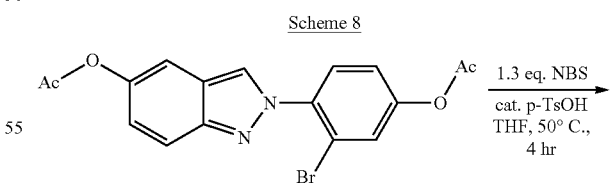

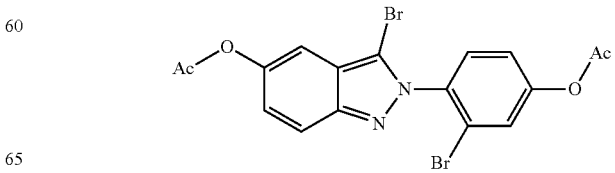

2-(4-acetoxy-2-bromophenyl)-3-bromo-2H-indazol-5-yl acetate (5,4'-diAc-IndBr-o-Br)

3-bromo-2-(2-bromo-4-hydroxyphenyl)-2H-indazol-5-ol (IndBr-o-Br)

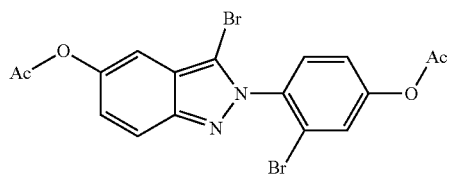 [SMILES: "Ac" ; Oc1ccc(-n2nc3ccc(O)cc3c2Br)c(Br)c1 ; "Ac"]

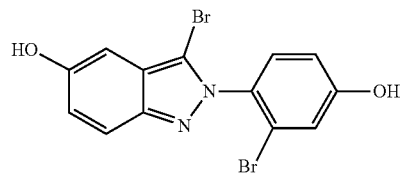 [SMILES: Oc1ccc(-n2nc3ccc(O)cc3c2Br)c(Br)c1]

5, 4'-diAc-IndBr-o-Br was prepared from the reaction of 5, 4'-diAc-Ind-o-Br (38.8 mg, 0.10 mmol) with NBS (29.00 mg, 0.13 mmol) and catalytic amount of p-TsOH in THF at 50° C. for 4 hr in 68% yield. $^1$H NMR (500 MHz, CDCl$_3$) δ 2.38 (s, 6H), 7.14 (dd, J=9.0, 2.5 Hz, 1H), 7.31 (dd, J=8.5, 2.5 Hz, 1H), 7.34 (d, J=2.5 Hz, 1H), 7.49 (d, J=9.0 Hz, 1H), 7.61 (d, J=2.5 Hz, 1H), 7.77 (d, J=9.0 Hz, 1H). $^{13}$C NMR (126 MHz, CDCl$_3$) δ 21.36, 21.40, 109.25, 110.69, 120.17, 121.73, 121.79, 122.51, 124.53, 126.89, 130.30, 136.23, 146.66, 147.91, 152.30, 168.68, 170.09. HRMS (ESI, M$^+$+1) C$_{17}$H$_{13}$Br$_2$N$_2$O$_2$ Calcd. 466.9242, found 466.9247.

IndBr-o-Br was quantitatively obtained from a procedure analogous to that used to make IndCl-o-Cl. $^1$H NMR (500 MHz, Chloroform-d+CD$_3$OD) δ 7.56 (d, J=9.2 Hz, 1H), 7.21 (d, J=8.6 Hz, 1H), 7.11 (d, J=2.6 Hz, 1H), 7.05 (dd, J=9.3, 2.3 Hz, 1H), 6.81 (dd, J=8.6, 2.6 Hz, 1H), 6.77 (d, J=1.8 Hz, 1H). $^{13}$C NMR (126 MHz, CDCl$_3$+CD$_3$OD) δ 159.49, 152.69, 145.55, 130.15, 129.98, 123.13, 122.56, 122.36, 120.15, 119.11, 115.42, 108.17, 99.46. HRMS (ESI, M$^+$+1) C$_{13}$H$_9$Br$_2$N$_2$O$_2$ Calcd. 382.9031, found 382.9028.

P. Synthesis of 3-bromo-2-(2-chloro-4-hydroxyphenyl)-2H-indazol-5-ol (IndBr-o-Cl)

3-bromo-2-(2-chloro-4-methoxyphenyl)-2H-indazol-5-yl acetate (5-Ac-IndBr-o-Cl-4'-OMe)

Scheme 9

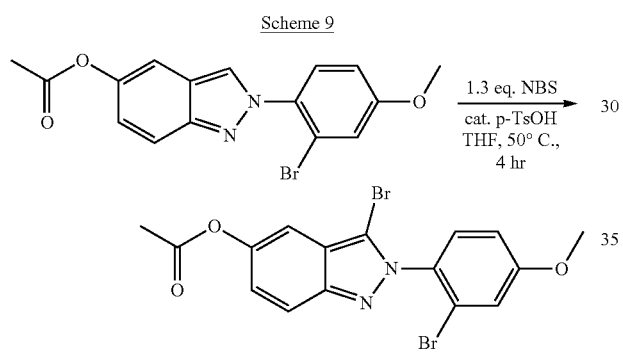

3-bromo-2-(2-bromo-4-methoxyphenyl)-2H-indazol-5-yl acetate (5-Ac-IndBr-o-Br-4'-OMe)

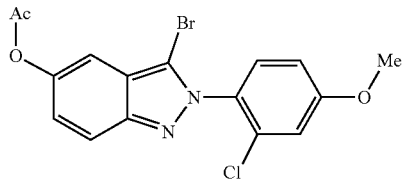 [SMILES: COc1ccc(-n2nc3ccc(OC(C)=O)cc3c2Br)c(Cl)c1]

5-Ac-IndBr-o-Cl-4'-OMe was obtained from the reaction of 5-Ac-Ind-o-Cl-4'-OMe (31.7 mg, 0.10 mmol) and with NBS (29.00 mg, 0.13 mmol) and catalytic amount of p-TsOH following an analogous procedure as described to prepare 5-Ac-IndBr-o-Br-4'-OMe. $^1$H NMR (500 MHz, Chloroform-d) δ 7.76 (d, J=9.3 Hz, 1H), 7.39 (d, J=8.7 Hz, 1H), 7.32 (d, J=1.8 Hz, 1H), 7.13 (d, J=2.3 Hz, 1H), 7.12 (dd, J=8.5, 2.5 Hz, 1H), 6.97 (dd, J=8.8, 2.6 Hz, 1H), 3.91 (s, 3H), 2.37 (s, 3H). $^{13}$C NMR (126 MHz, CDCl$_3$) δ 170.09, 161.49, 147.75, 146.49, 133.33, 130.28, 129.90, 124.30, 121.64, 120.07, 115.51, 113.50, 110.67, 109.72, 56.17, 21.40. HRMS (ESI, M$^+$+1) C$_{16}$H$_{13}$BrClN$_2$O$_3$ Calcd. 394.9798, found 394.9800.

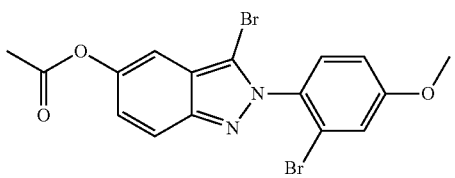

5-Ac-IndBr-o-Br-4'-OMe was prepared from the reaction of 5-Ac-Ind-o-Br-4'-OMe (36.1 mg, 0.10 mmol) with NBS (29.00 mg, 0.13 mmol) and catalytic amount of p-TsOH in TH at 50° C. for 4 hr in 72% yield following an analogous procedure as described to prepare 5,4'-diAc-IndBr-o-Br as shown in Scheme 9. $^1$H NMR (500 MHz, CDCl$_3$) δ 2.37 (s, 3H), 3.91 (s, 3H), 6.97 (dd, J=2.5, 8.5 Hz, 1H), 7.12 (dd, J=2.0, 8.5 Hz, 1H), 7.12 (d, J=2.0 Hz, 1H), 7.32 (d, J=2.0 Hz, 1H), 7.39 (d, J=9.0 Hz, 1H), 7.76 (d, J=9.0 Hz, 1H). $^{13}$C NMR (126 MHz, CDCl$_3$) δ 21.41, 56.19, 109.73, 110.69, 113.51, 115.52, 120.09, 124.31, 129.91, 130.30, 133.34, 146.51, 147.77, 161.51, 170.11. HRMS (ESI, M$^+$+1) C$_{16}$H$_{13}$Br$_2$N$_2$O3 Calcd. 438.9293, found 438.9294.

3-bromo-2-(2-chloro-4-hydroxyphenyl)-2H-indazol-5-ol (IndBr-o-Cl)

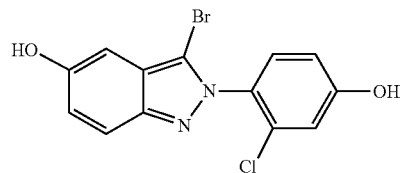

The treatment of 5-Ac-IndBr-o-Cl-4'-OMe with borontrifluoride disulfide (15 eq.) afforded IndBr-o-Cl quantitatively as a pale brownish solid. $^1$H NMR (500 MHz, Chloroform-d+CD$_3$OD) δ 7.52 (d, J=9.2 Hz, 1H), 7.21 (d, J=8.6 Hz, 1H), 7.04 (dd, J=8.5, 2.5 Hz, 1H, 1H), 6.95 (d, J=2.5 Hz, 1H), 6.80 (dd, J=8.5, 2.5 Hz, 1H), 6.74 (d, J=2.5 Hz, 1H). $^{13}$C NMR (126 MHz, CDCl$_3$+CD$_3$OD) δ 159.60, 152.79, 145.62, 133.03, 130.19, 128.35, 123.08, 122.36, 119.01, 116.98, 114.77, 108.11, 99.25. HRMS (ESI, M$^+$+1) C$_{13}$H$_9$BrClN$_2$O$_2$ Calcd. 338.9536, found 338.9532.

Q. Synthesis of 3-bromo-2-(4-hydroxy-2-methylphenyl)-2H-indazol-5-ol (IndBr-o-Me)

3-bromo-2-(4-methoxy-2-methylphenyl)-2H-indazol-5-yl acetate (5-Ac-IndBr-o-Me-4'-methoxy)

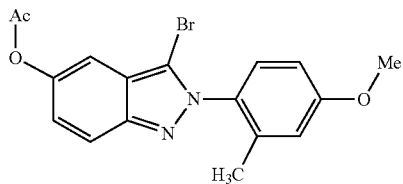

$^1$H NMR (500 MHz, Chloroform-d) δ 7.75 (d, J=9.2 Hz, 1H), 7.32 (d, J=2.1 Hz, 1H), 7.25 (d, J=8.5 Hz, 1H), 7.10 (dd, J=9.2, 2.1 Hz, 1H), 6.90 (d, J=2.5 Hz, 1H), 6.88 (dd, J=8.6, 2.7 Hz, 1H), 3.89 (s, 3H), 2.37 (s, 3H), 2.04 (s, 3H). 13C NMR (126 MHz, CDCl$_3$) δ 170.18, 160.81, 147.53, 146.32, 137.43, 131.53, 128.96, 123.84, 121.57, 120.03, 116.10, 111.93, 110.66, 108.85, 55.77, 21.40, 17.85. HRMS (ESI, M+1) Calcd. for C$_{17}$H$_{16}$BrN$_2$O$_3$ 375.0344, found 375.0336.

3-bromo-2-(4-hydroxy-2-methylphenyl)-2H-indazol-5-ol (IndBr-o-Me)

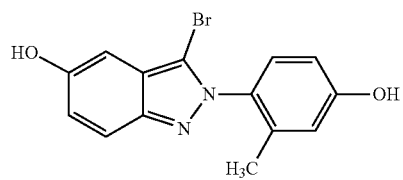

$^1$H NMR (500 MHz, Chloroform-d+CD$_3$OD) δ 7.41 (d, J=9.2 Hz, 1H), 6.99 (d, J=8.4 Hz, 1H), 6.93 (dd, J=8.5, 2.5 Hz, 1H), 6.70-6.62 (m, 3H), 1.81 (s, 3H). $^{13}$C NMR (126 MHz, CDCl$_3$+CD$_3$OD) δ 158.44, 152.68, 145.26, 137.35, 130.19, 128.81, 122.40, 122.23, 118.82, 117.14, 113.29, 107.06, 99.03, 17.15. HRMS (ESI, M+1) Calcd. for C$_{14}$H$_{12}$BrN$_2$O$_2$ 319.0082, found 319.0073.

R. Synthesis of 3-bromo-2-(4-hydroxy-2-iodophenyl)-2H-indazol-5-ol (IndBr-o-I)

2-(4-acetoxy-2-iodophenyl)-3-bromo-2H-indazol-5-yl acetate (5,4'-diAc-IndBr-o-I)

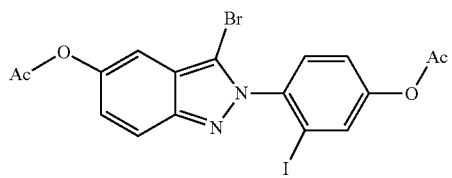

5,4'-diAc-IndBr-o-I was obtained from the reaction of 5,4'-diAc-Ind-o-I (43.6 mg, 0.10 mmol) and with NBS (29.00 mg, 0.13 mmol) and catalytic amount of p-TsOH following an analogous procedure as described to prepare 5-Ac-IndBr-o-Br-4'-OMe. $^1$H NMR (500 MHz, CDCl$_3$) δ 2.37 (s, 3H), 2.38 (s, 3H), 7.14 (dd, J=9.0, 2.0 Hz, 1H), 7.33 (dd, J=8.5, 2.5 Hz, 1H), 7.34 (d, J=2.5 Hz, 1H), 7.44 (d, J=8.5 Hz, 1H), 7.78 (d, J=9.5 Hz, 1H), 7.81 (d, J=2.5 Hz, 1H). $^{13}$C NMR (126 MHz, CDCl$_3$) δ 21.34, 21.41, 96.72, 108.89, 110.67, 120.20, 121.94, 122.52, 124.52, 129.52, 132.85, 139.79, 146.66, 147.81, 151.94, 168.73, 170.09. HRMS (ESI, M$^+$+1) Calcd. for C$_{17}$H$_{13}$BrIN$_2$O$_2$ 514.9103, found 514.9094.

3-bromo-2-(4-hydroxy-2-iodophenyl)-2H-indazol-5-ol (IndBr-o-I)

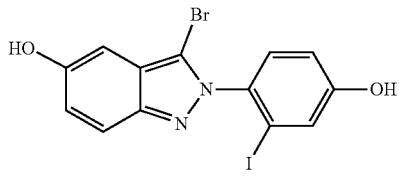 [SMILES: Oc1ccc(-n2nc3ccc(O)cc3c2Br)c(Cl)c1]

Treatment of 5,4'-diAc-IndBr-o-I (25.7 mg, 0.05 mmol) with K$_2$CO$_3$ (80 mg) in MeOH at rt for 1 hr and subsequently with 1N HCl solution to adjust pH ~2 formed a colorless solid in aqueous solution. The suspended solid was collected by filtration and dried under vacuum to provide IndBr-o-I in 96% yield. $^1$H NMR (500 MHz, Chloroform-d+CD$_3$OD) δ 7.53 (d, J=9.3 Hz, 1H), 7.36 (d, J=2.4 Hz, 1H), 7.15 (d, J=8.5 Hz, 1H), 7.04-7.00 (dd, J=8.5, 2.5 Hz, 1H), 6.86 (dd, J=8.6, 2.5 Hz, 1H), 6.74 (d, J=2.0 Hz, 1H). $^{13}$C NMR (126 MHz, CDCl$_3$+CD$_3$OD) δ 159.51, 152.81, 145.57, 133.62, 129.37, 126.20, 122.84, 122.51, 119.27, 116.03, 107.26, 99.13, 97.24. HRMS (ESI, M+1) Calcd. for C$_{13}$H$_9$BrIN$_2$O$_2$ 430.8892, found 430.8884.

S. Synthesis of 3-fluoro-2-(4-hydroxy-2-methylphenyl)-2H-indazol-5-ol (IndF-o-Me)

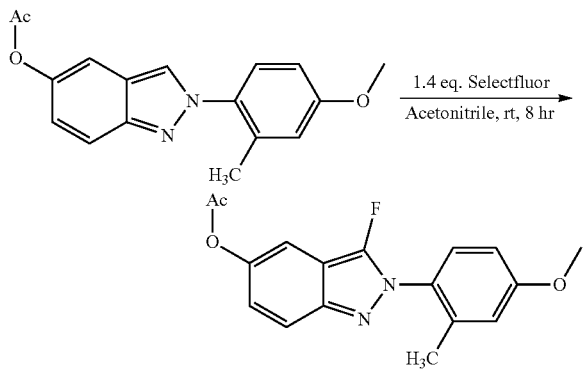

Scheme 10

3-fluoro-2-(4-methoxy-2-methylphenyl)-2H-indazol-5-yl acetate (5-Ac-IndF-o-Me-4'-OMe)

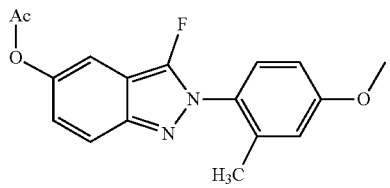 [SMILES: COc1ccc(-n2nc3ccc(OC(C)=O)cc3c2F)c(C)c1]

5-Ac-IndF-o-Me-4'-OMe was prepared from the reaction of 5-Ac-Ind-o-Me-4'-OMe (29.6 mg, 0.10 mmol) with Selectfluor® (49.28 mg, 0.14 mmol) in acetonitrile at rt for 8 hr in 66% yield as shown in Scheme 10 and following an analogous procedure as described to prepare 5,4'-diAc-IndCl-o-Cl. $^1$H NMR (500 MHz, CDCl$_3$) δ 2.17 (s, 3H), 2.36 (s, 3H), 3.88 (s, 3H), 6.88 (dd, J=9.0, 2.5 Hz, 1H), 6.90 (d, J=3.0 Hz, 1H), 7.05 (dd, J=9.0, 2.5 Hz, 1H), 7.31 (s, 1H), 7.32 (d, J=8.5 Hz, 1H), 7.60 (dd, J=9.0, 1.5 Hz, 1H). $^{13}$C NMR (126 MHz, CDCl$_3$) δ 17.89, 21.38, 55.78, 102.96 (d, J=13.3 Hz), 108.75 (d, J=4.8 Hz), 112.18, 116.31, 119.71, 124.02, 128.63, 136.89, 145.42 (d, J=2.5 Hz), 145.62 (d, J=21.04 Hz), 146.77 (d, J=256.4 Hz), 160.85, 170.19. $^{19}$F NMR (470 MHz, CDCl$_3$) δ -134.06. HRMS (ESI, M+1) Calcd. for C$_{17}$H$_{16}$FN$_2$O$_3$ 315.1145, found 315.1135.

3-fluoro-2-(4-hydroxy-2-methylphenyl)-2H-indazol-5-ol (IndF-o-Me)

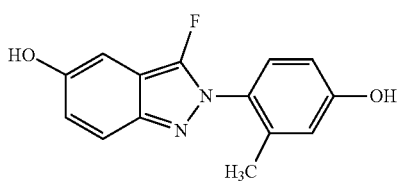

Treatment of 5-Ac-IndF-o-Me-4'-OMe with BF$_3$—SMe$_2$ (20 eq.) in DCM at rt for 4 hr afforded IndF-o-Me quantitatively. $^1$H NMR (500 MHz, Chloroform-d+CD$_3$OD) δ 7.35 (d, J=8.5 Hz, 1H), 7.12 (d, J=8.4 Hz, 1H), 6.96 (dd, J=9.0, 2.5 Hz, 1H), 6.78-6.65 (m, 3H), 1.99 (s, 3H). $^{13}$C NMR (126 MHz, CDCl$_3$+CD$_3$OD) δ 158.61, 151.77, 145.70 (d, J=281.0 Hz), 143.85 (d, J=8.3 Hz), 136.92, 128.55, 127.13, 123.09, 118.48, 117.48, 113.65, 103.64 (d, J=13.0 Hz), 97.03 97.05 (d, J=4.4 Hz), 17.29. $^{19}$F NMR (470 MHz, CDCl$_3$+CD$_3$OD) δ -136.53. HRMS (ESI, M+1) Calcd. for C$_{14}$H$_{12}$FN$_2$O$_2$ 259.0883, found 215.0888.

T. Synthesis of 2-(2-chloro-4-hydroxyphenyl)-3-fluoro-2H-indazol-5-ol (IndF-o-Cl)

2-(2-chloro-4-methoxyphenyl)-3-fluoro-2H-indazol-5-yl acetate (5-Ac-IndF-o-Cl-4'-OMe)

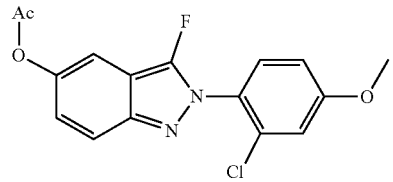 [SMILES: COc1ccc(-n2nc3ccc(OC(C)=O)cc3c2F)c(Cl)c1]

5-Ac-IndF-o-Cl-4'-OMe was prepared from the reaction of 5-Ac-Ind-o-Cl-4'-OMe (31.70 mg, 0.10 mmol) with Selectfluor® (49.28 mg, 0.14 mmol) in acetonitrile at rt for 8 hr in 71% yield following an analogous procedure as described to prepare 5-Ac-IndF-o-Me-4'-OMe.

$^1$H NMR (500 MHz, CDCl$_3$) δ 2.36 (s, 3H), 3.90 (s, 3H), 6.98 (dd, J=9.0, 3.0 Hz, 1H), 7.06 (dd, J=9.5, 3.0 Hz, 1H), 7.12 (d, J=3.0 Hz, 1H), 7.32 (d, J=2.0 Hz, 1H), 7.47 (d, J=8.5 Hz, 1H), 7.60 (d, J=9.5 Hz, 1H). $^{13}$C NMR (126 MHz, CDCl$_3$) δ 21.37, 56.19, 102.96 (d, J=12.9 Hz), 108.79 (d, J=4.7 Hz), 113.77, 115.58, 119.76, 124.49, 127.27, 130.00, 132.52, 145.54 (d, J=2.8 Hz), 146.05 (d, J=21.05 Hz), 147.03 (d, J=256.9 Hz), 161.51, 170.10. $^{19}$F NMR (470 MHz, CDCl$_3$) δ -131.85. HRMS (ESI, M+1) Calcd. for C$_{16}$H$_{13}$FClN$_2$O$_3$ 335.0599, found 335.0609.

2-(2-chloro-4-hydroxyphenyl)-3-fluoro-2H-indazol-5-ol (IndF-o-Cl)

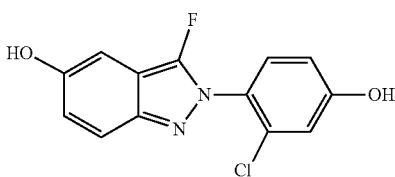 [SMILES: Oc1ccc(-n2nc3ccc(O)cc3c2F)c(Cl)c1]

Treatment of 5-Ac-IndF-o-Cl-4'-OMe with BF$_3$—SMe$_2$ (20 eq.) in DCM at rt for 4 hr afforded IndF-o-Cl quantitatively. $^1$H NMR (500 MHz, Chloroform-d+CD$_3$OD) δ 7.36 (d, J=8.5 Hz, 1H), 7.27 (d, J=8.4 Hz, 1H), 6.92-7.05 (m, 2H), 6.85-6.71 (m, 2H). $^{13}$C NMR (126 MHz, CDCl$_3$) δ 159.62, 151.75, 146.03 (d, J=281.0 Hz), 144.65 (d, J=8.0 Hz), 132.28, 129.87, 125.77, 123.36, 118.79, 117.01, 114.93, 103.55 (d, J=12.5 Hz), 96.98 (d, J=4.4 Hz). $^{19}$F NMR (470 MHz, CDCl$_3$+CD$_3$OD) δ -135.05. HRMS (ESI, M+1) Calcd. for C$_{13}$H$_9$FClN$_2$O$_2$ 279.0337, found 279.0331.

U. Synthesis of 2-(2-bromo-4-hydroxyphenyl)-3-fluoro-2H-indazol-5-ol (IndF-o-Br)

2-(2-bromo-4-methoxyphenyl)-3-fluoro-2H-indazol-5-yl acetate (5-Ac-IndF-o-Br-4'-OMe)

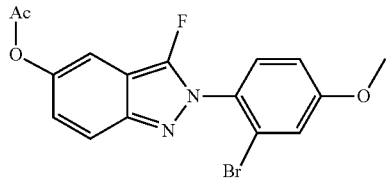 [SMILES: COc1ccc(-n2nc3ccc(OC(C)=O)cc3c2F)c(Br)c1]

5-Ac-IndF-o-Br-4'-OMe was prepared from the reaction of 5-Ac-Ind-o-Me-4'-OMe (29.6 mg, 0.10 mmol) with Selectfluor® (49.28 mg, 0.14 mmol) in acetonitrile at rt for 8 hr in 66% yield following an analogous procedure as described to prepare 5-Ac-IndF-o-Me-4'-OMe. $^1$H NMR (500 MHz, CDCl$_3$) δ 2.36 (s, 3H), 3.90 (s, 3H), 7.01 (dd, J=9.0, 3.0 Hz, 1H), 7.06 (dd, J=9.5, 3.0 Hz, 1H), 7.29 (d, J=3.0 Hz, 1H), 7.32 (d, J=2.0 Hz, 1H), 7.44 (d, J=8.5 Hz, 1H), 7.60 (d, J=9.0 Hz, 1H). $^{13}$C NMR (126 MHz, CDCl$_3$) δ 21.38, 56.20, 102.97 (d, J=11.9 Hz), 108.81 (d, J=5.5 Hz), 114.28, 118.64, 119.80, 121.92, 124.50, 128.94, 130.07, 145.55 (d, J=2.6 Hz), 145.90 (d, J=23.3 Hz), 146.95 (d, J=254.2 Hz), 161.51, 170.11. $^{19}$F NMR (470 MHz, CDCl$_3$) δ −131.70. HRMS (ESI, M$^+$+1) Calcd. for C$_{16}$H$_{13}$FBrN$_2$O$_3$ 379.0094, found 379.0093.

2-(2-bromo-4-hydroxyphenyl)-3-fluoro-2H-indazol-5-ol (IndF-o-Br)

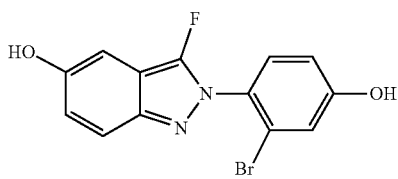

Treatment of 5-Ac-IndF-o-Br-4'-OMe with BF$_3$—SMe$_2$ (20 eq.) in DCM at rt for 4 hr afforded IndF-o-Br quantitatively. $^1$H NMR (500 MHz, Chloroform-d+CD$_3$OD) δ 7.37 (d, J=8.4 Hz, 1H), 7.27 (d, J=8.0 Hz, 1H), 7.13 (d, J=2.0 Hz, 1H), 6.98 (dd, J=9.5, 3.0 Hz, 1H), 6.84 (dd, J=8.5, 2.5 Hz, 1H), 6.73 (s, 1H). $^{13}$C NMR (126 MHz, CDCl$_3$+CD$_3$OD) δ 159.70, 151.80, 145.83 (d, J=282.8 Hz), 144.42 (d, J=8.8 Hz), 129.93, 127.33, 123.43, 121.74, 120.07, 118.75, 115.41, 103.59 (d, J=13.0 Hz), 97.00 (d, J=4.4 Hz). $^{19}$F NMR (470 MHz, CDCl$_3$) δ −134.88. HRMS (ESI, M$^+$+1) Calcd. for C$_{13}$H$_9$FBrN$_2$O$_2$ 322.9831, found 322.9830.

V. Synthesis of 3-fluoro-2-(4-hydroxy-2-iodophenyl)-2H-indazol-5-ol (IndF-o-I)

2-(4-acetoxy-2-iodophenyl)-3-fluoro-2H-indazol-5-yl acetate (4',5-diAc-IndF-o-I)

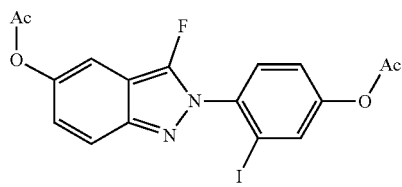 [SMILES: CC(=O)Oc1ccc(-n2nc3ccc(OC(C)=O)cc3c2F)c(I)c1]

5,4'-DiAc-IndF-o-I was prepared from the reaction of 5,4'-DiAc-Ind-o-I (43.6 mg, 0.10 mmol) with Selectfluor® (49.28 mg, 0.14 mmol) in acetonitrile at rt for 8 hr in 51% yield following an analogous procedure as described to prepare 5-Ac-IndF-o-Me-4'-OMe. $^1$H NMR (500 MHz, CDCl$_3$) δ 2.36 (s, 6H), 7.07 (dd, J=9.0, 2.5 Hz, 1H), 7.32 (dd, J=8.5, 2.50 Hz, 1H), 7.34 (d, J=2.5 Hz, 1H), 7.48 (d, J=8.5 Hz, 1H), 7.62 (d, J=9.0 Hz, 1H), 7.79 (d, J=2.5 Hz, 1H), $^{13}$C NMR (126 MHz, CDCl$_3$) δ 21.31, 21.39, 95.62, 103.27 (d, J=12.3 Hz), 108.84 (d, J=4.8 Hz), 119.86, 122.70, 124.78, 129.41, 133.05, 137.29 (d, J=2.2 Hz), 138.32, 146.58 (d, J=237.7 Hz), 152.01, 168.76, 170.07. $^{19}$F NMR (470 MHz, CDCl$_3$) δ −131.03. HRMS (ESI, M$^+$+1) Calcd. for C$_{17}$H$_{13}$FIN$_2$O$_4$ 454.9904, found 454.9893.

3-fluoro-2-(4-hydroxy-2-iodophenyl)-2H-indazol-5-ol (IndF-o-I)

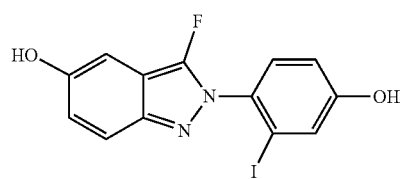

Treatment of 5,4'-DiAc-IndF-o-I (22.7 mg, 0.05 mmol) with K$_2$CO$_3$ (80 mg) in MeOH at rt for 1 hr and subsequently with 1N HCl solution to adjust pH ~2 formed a colorless solid in aqueous solution. The suspended solid was collected by filtration and dried under vacuum to provide IndF-o-I in 93% yield. $^1$H NMR (500 MHz, Chloroform-d+CD$_3$OD) δ 7.41 (d, J=9.2 Hz, 1H), 7.38 (d, J=2.6 Hz, 1H), 7.22 (d, J=8.6 Hz, 1H), 6.99 (dd, J=9.4, 2.3 Hz, 1H), 6.88 (dd, J=8.6, 2.6 Hz, 1H), 6.76 (d, J=2.1 Hz, 1H). $^{19}$F NMR (470 MHz, CDCl$_3$) δ −134.88. HRMS (ESI, M$^+$+1) Calcd. for C$_{13}$H$_9$FIN$_2$O$_2$ 370.9693, found 370.9702.

W. Synthesis of 2-(4-hydroxy-2-methylphenyl)-3-iodo-2H-indazol-5-ol (IndI-o-Me)

Scheme 11

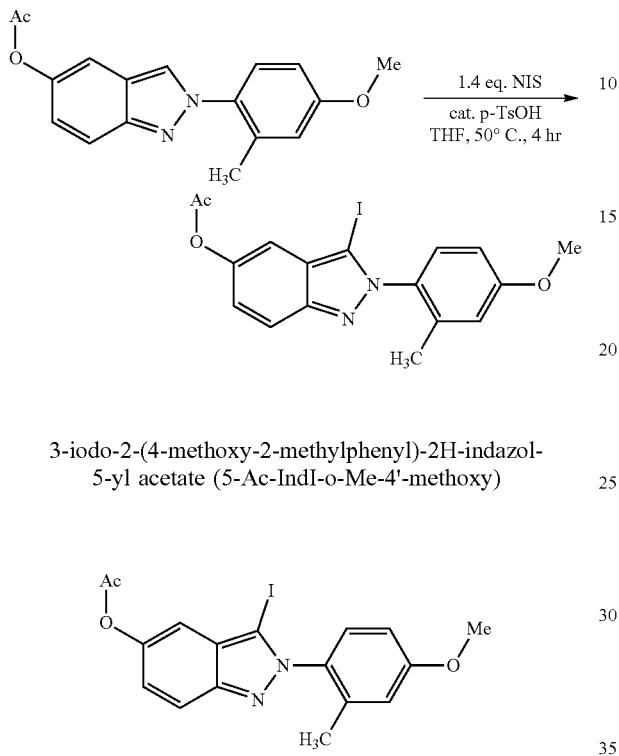

3-iodo-2-(4-methoxy-2-methylphenyl)-2H-indazol-5-yl acetate (5-Ac-IndI-o-Me-4'-methoxy)

5-Ac-IndI-o-Me-4'-methoxy was obtained in 68% yield from the reaction of 5-Ac-Ind-o-Me-4'-methoxy (40.8 mg, 0.10 mmol) and with NIS (31.4 mg, 0.14 mmol) and catalytic amount of p-TsOH following an analogous procedure as described to prepare 5-Ac-IndBr-o-Br-4'-OMe as shown in Scheme 11. $^1$H NMR (500 MHz, Chloroform-d) δ 7.76 (d, J=9.2 Hz, 1H), 7.23 (d, J=2.5 Hz, 1H), 7.22 (d, J=8.4 Hz, 1H), 7.11 (dd, J=9.2, 2.1 Hz, 1H), 6.90 (d, J=2.5 Hz, 1H), 6.88 (dd, J=8.6, 2.6 Hz, 1H), 3.89 (s, 3H), 2.37 (s, 3H), 2.00 (s, 3H). $^{13}$C NMR (126 MHz, CDCl$_3$) δ 170.24, 160.78, 148.36, 146.55, 137.45, 133.07, 129.17, 127.12, 123.77, 120.10, 116.05, 112.00, 111.87, 79.22, 55.77, 21.41, 17.97. HRMS (ESI, M$^+$+1) Calcd. for C$_{17}$H$_{16}$IN$_2$O$_3$ 423.0206, found 423.0200.

2-(4-hydroxy-2-methylphenyl)-3-iodo-2H-indazol-5-ol (IndI-o-Me)

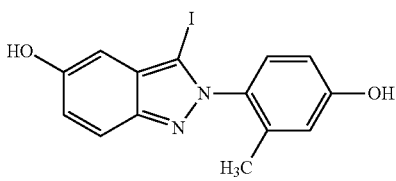

Treatment of 5-Ac-IndI-o-Me-4'-methoxy with BF$_3$—SMe$_2$ (20 eq.) in DCM at rt for 4 hr afforded IndI-o-Me quantitatively. $^1$H NMR (500 MHz, CDCl$_3$+CD$_3$OD) δ 7.50 (d, J=9.1 Hz, 1H), 7.06 (d, J=8.5 Hz, 1H), 7.03 (dd, J=9.3, 2.2 Hz, 1H), 6.76 (s, 1H), 6.73 (dd, J=8.3, 2.3 Hz, 1H), 6.67 (d, J=1.6 Hz, 1H), 1.86 (s, 3H). $^{13}$C NMR (126 MHz, CDCl$_3$+CD$_3$OD) δ 158.57, 153.00, 145.77, 137.45, 131.70, 129.11, 127.94, 122.48, 118.78, 117.19, 113.33, 100.73, 78.20, 17.32. HRMS (ESI, M$^+$+1) Calcd. for C$_{14}$H$_{12}$IN$_2$O$_2$ 366.9944, found 366.9953.

X. Synthesis of 2-(2-chloro-4-hydroxyphenyl)-3-iodo-2H-indazol-5-ol (IndI-o-Cl)

Scheme 12

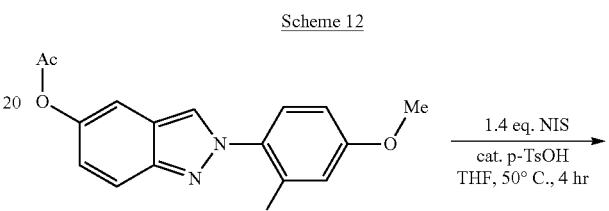

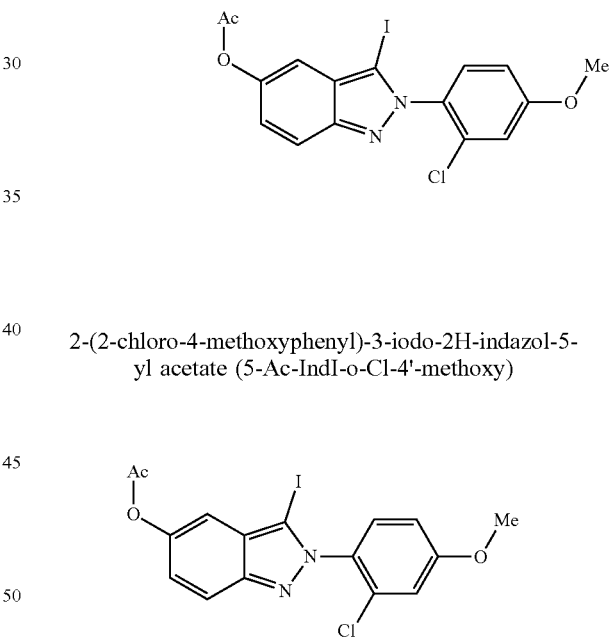

2-(2-chloro-4-methoxyphenyl)-3-iodo-2H-indazol-5-yl acetate (5-Ac-IndI-o-Cl-4'-methoxy)

5-Ac-IndI-o-Cl-4'-methoxy was obtained in 68% yield from the reaction of 5-Ac-Ind-o-Cl-4'-methoxy (31.7 mg, 0.10 mmol) and with NIS (31.4 mg, 0.14 mmol) and catalytic amount of p-TsOH following an analogous procedure as described to prepare 5-Ac-IndI-o-Me-4'-methoxy as shown in Scheme 12. $^1$H NMR (500 MHz, CDCl$_3$) δ 2.38 (s, 3H), 3.93 (s, 3H), 6.99 (dd, J=8.5, 2.5 Hz, 1H), 7.12 (dd, J=8.5, 2.5 Hz, 1H), 7.12 (d, J=3.0 Hz, 1H), 7.23 (d, J=2.5 Hz, 1H), 7.36 (d, J=9.0 Hz, 1H), 7.74 (d, J=9.5 Hz, 1H). $^{13}$C NMR (126 MHz, CDCl$_3$) δ 21.42, 56.20, 80.00, 112.02, 113.46, 115.49, 120.16, 124.23, 127.25, 130.49, 131.39, 133.44, 146.73, 148.49, 161.48, 170.17. HRMS (ESI, M$^+$+1) Calcd. for C$_{16}$H$_{13}$C$_1$IN$_2$O$_3$ 442.9659, found 446.9654.

2-(2-chloro-4-hydroxyphenyl)-3-iodo-2H-indazol-5-ol (IndI-o-Cl)

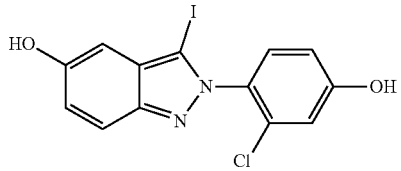 [SMILES: Oc1ccc(-n2nc3ccc(O)cc3c2I)c(Cl)c1]

Treatment of 5-Ac-IndI-o-Cl-4'-methoxy with BF$_3$—SMe$_2$ (20 eq.) in DCM at rt for 4 hr afforded IndI-o-Cl quantitatively. $^1$H NMR (500 MHz, CDCl$_3$+CD$_3$OD) δ 7.52 (d, J=9.2 Hz, 1H), 7.18 (d, J=8.6 Hz, 1H), 7.02 (dd, J=9.0, 2.5 Hz, 1H), 6.96 (d, J=2.5 Hz, 1H), 6.79 (dd, J=9.0, 2.5 Hz, 1H), 6.65 (d, J=2.5 Hz, 1H). $^{13}$C NMR (126 MHz, CDCl$_3$+CD$_3$OD) δ 159.53, 152.99, 146.25, 133.13, 130.38, 129.93, 127.98, 122.76, 119.18, 116.90, 116.88, 114.66, 100.62. HRMS (ESI, M$^+$+1) Calcd. for C$_{13}$H$_9$C$_1$IN$_2$O$_2$ 386.9397, found 386.9391.

Y. Synthesis of 2-(2-bromo-4-hydroxyphenyl)-3-iodo-2H-indazol-5-ol (IndI-o-Br)

2-(4-acetoxy-2-bromophenyl)-3-iodo-2H-indazol-5-yl acetate (IndI-o-Br-5,4'-diAc)

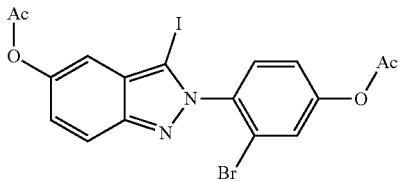 [SMILES: "Ac" ; CC(=O)Oc1ccc(-n2nc3ccc(O)cc3c2I)c(Br)c1]

IndI-o-Br-5,4'-diAc was obtained in 77% yield from the reaction of Ind-o-Br-5,4'-diAc (38.9 mg, 0.10 mmol) and with NIS (31.4 mg, 0.14 mmol) and catalytic amount of p-TsOH following an analogous procedure as described to prepare 5-Ac-IndI-o-Me-4'-methoxy. $^1$H NMR (500 MHz, CDCl$_3$) δ 7.78 (d, J=9.2 Hz, 1H), 7.61 (d, J=2.4 Hz, 1H), 7.46 (d, J=8.6 Hz, 1H), 7.30 (dd, J=8.6, 2.5 Hz, 1H), 7.24 (d, J=2.0 Hz, 1H), 7.14 (dd, J=9.2, 2.1 Hz, 1H), 2.38 (s, 3H), 2.37 (s, 3H). $^{13}$C NMR (126 MHz, CDCl$_3$) δ 170.13, 168.63, 152.25, 148.55, 146.86, 137.55, 130.45, 127.36, 126.82, 124.42, 122.68, 121.67, 120.22, 112.00, 79.22, 21.41, 21.37. HRMS (ESI, M$^+$+1) Calcd. for C$_{17}$H$_{13}$BrIN$_2$O$_4$ 514.9103, found 514.9124.

2-(2-bromo-4-hydroxyphenyl)-3-iodo-2H-indazol-5-ol (IndI-o-Br)

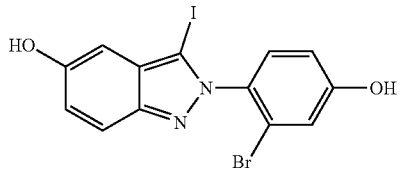 [SMILES: Oc1ccc(-n2nc3ccc(O)cc3c2I)c(Br)c1]

Treatment of IndI-o-Br-5,4'-diAc (25.7 mg, 0.05 mmol) with K$_2$CO$_3$ (80 mg) in MeOH at rt for 1 hr and subsequently with 1N HCl solution to adjust pH ~2 formed a colorless solid in aqueous solution. The suspended solid was collected by filtration and drying under vacuum provided IndI-o-Br in 91% yield. $^1$H NMR (500 MHz, CDCl$_3$+CD$_3$OD) δ 7.51 (d, J=9.2 Hz, 1H), 7.17 (d, J=8.6 Hz, 1H), 7.13 (d, J=2.5 Hz, 1H), 7.01 (dd, J=9.2, 2.2 Hz, 2H), 6.84 (dd, J=8.6, 2.5 Hz, 2H), 6.64 (d, J=1.9 Hz, 1H). $^{13}$C NMR (126 MHz, CDCl$_3$+CD$_3$OD) δ 159.50, 153.01, 146.15, 131.56, 130.34, 127.95, 122.70, 121.70, 119.90, 119.20, 115.16, 100.59, 78.04. HRMS (ESI, M$^+$+1) Calcd. for C$_{13}$H$_9$BrIN$_2$O$_2$ 430.8892, found 430.8893.

Z. Synthesis of 2-(4-hydroxy-2-iodophenyl)-3-iodo-2H-indazol-5-ol (IndI-o-I)

2-(4-acetoxy-2-iodophenyl)-3-iodo-2H-indazol-5-yl acetate (IndI-o-I-5,4'-diAc)

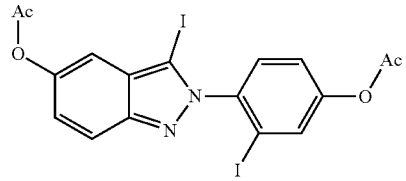

IndI-o-I-5,4'-diAc was obtained in 71% yield from the reaction of Ind-o-I-5,4'-diAc (43.6 mg, 0.10 mmol) and with NIS (31.4 mg, 0.14 mmol) and catalytic amount of p-TsOH following an analogous procedure as described to prepare 5-Ac-IndI-o-Me-4'-methoxy. $^1$H NMR (500 MHz, CDCl$_3$) δ 7.80 (d, J=2.5 Hz, 2H), 7.79 (d, J=9.3 Hz, 2H), 7.41 (d, J=8.5 Hz, 2H), 7.33 (dd, J=8.5, 2.4 Hz, 2H), 7.24 (d, J=2.1 Hz, 2H), 7.15 (dd, J=9.2, 2.1 Hz, 2H). $^{13}$C NMR (126 MHz, CDCl$_3$) δ 170.13, 168.67, 151.87, 148.50, 146.87, 141.05, 132.76, 129.69, 127.47, 124.42, 122.46, 120.24, 112.02, 97.10, 79.06, 21.42, 21.36. HRMS (ESI, M$^+$+1) Calcd. for C$_{17}$H$_{13}$I$_2$N$_2$O$_4$ 562.8965, found 562.8960.

2-(4-hydroxy-2-iodophenyl)-3-iodo-2H-indazol-5-ol (IndI-o-I)

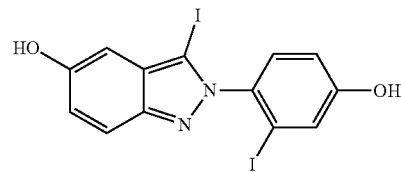

Treatment of IndI-o-I-5,4'-diAc (28.1 mg, 0.05 mmol) with K$_2$CO$_3$ (80 mg) in MeOH at rt for 1 hr and subsequently with 1N HCl solution to adjust pH ~2 formed a colorless solid in aqueous solution. The suspended solid was collected by filtration and dried under vacuum providing IndI-o-I in 95% yield. $^1$H NMR (500 MHz, CDCl$_3$+CD$_3$OD) δ 7.50 (d, J=9.2 Hz, 1H), 7.35 (d, J=2.3 Hz, 1H), 7.11 (d, J=8.6 Hz, 1H), 7.01 (dd, J=8.5, 2.3 Hz, 1H), 6.86 (dd, J=8.5, 2.3 Hz, 1H), 6.63 (s, 1H). $^{13}$C NMR (126 MHz, CDCl$_3$+CD$_3$OD) δ 159.14, 153.01, 146.15, 135.16, 129.56, 128.07, 126.00, 122.67, 119.25, 115.85, 100.58, 97.58, 77.96. HRMS (ESI, M+ +1) Calcd. for $C_{13}H_9I2N_2O_2$ 478.8754, found 478.8768.

AA. Synthesis of 2-(2-bromo-4-hydroxyphenyl)-3-vinyl-2H-indazol-5-ol (Ind-Vinyl-o-Br) (29)

3-(1-hydroxyallyl)phenol

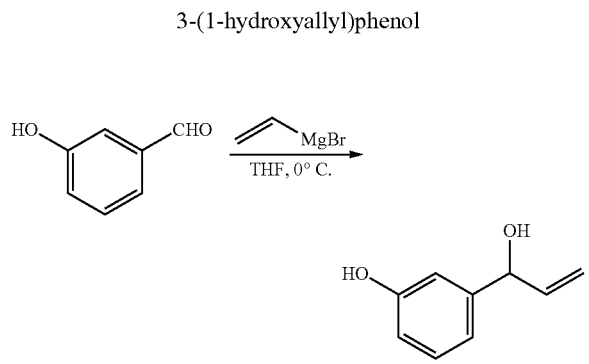

To the solution of 3-hydroxybenzaldehyde (6.1 g, 50 mmol) in dried THF (100 mL) was added dropwise vinyl magnesium bromide solution (150 mL, 1M THF) at 0° C. The resultant was stirred for 4 hr at the same temperature before quenching with sat. ammonium chloride solution. The ppt was loaded onto the $SiO_2$ for column chromatography with a mixture of ethyl acetate and n-hexane (2:1) to afford a colorless solid (6.2 g, 83%). $^1$H NMR (500 MHz, Chloroform-d+ Methanol-$d_4$) 5.06 (dd, J=6.1, 1.5 Hz, 1H), 5.13 (dt, J=10.3, 1.4 Hz, 1H), 5.27 (dt, J=17.1, 1.5 Hz, 1H), 5.97 (ddd, J=17.1, 10.3, 6.1 Hz, 1H), 6.68-6.75 (m, 1H), 6.77-6.84 (m, 2H), 7.10-7.19 (m, 1H). $^{13}$C NMR (126 MHz, $CDCl_3$+MeOH-$d_4$) δ 75.21, 113.27, 114.88, 115.16, 118.13, 129.79, 140.28, 144.48, 156.95.

4-((2-bromo-4-methoxyphenyl)diazenyl)-3-(1-hydroxyallyl)phenol (Allyl-OH-Azo-o-Br)

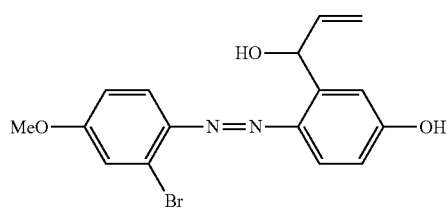 [SMILES: C=CC(O)c1cc(O)ccc1N=Nc1ccc(OC)cc1Br]

Allyl-OH-Azo-o-Br was obtained from the reaction with p-methoxy-2-bromoaniline (404 g, 2.00 mmol), $NaNO_2$ (142 mg, 2.06 mmol), 3-(1-hydroxyallyl)phenol (0.30 g, 2.00 mmol) in 95% yield as yellowish solid as described to make Azo-o-Cl compound. $^1$H NMR (500 MHz, Chloroform-d+Methanol-$d_4$) δ 5.05 (dt, J=10.4, 1.6 Hz, 1H), 5.19 (dt, J=17.1, 1.6 Hz, 1H), 5.93 (dt, J=5.4, 1.6 Hz, 1H), 6.04 (ddd, J=17.1, 10.4, 5.3 Hz, 1H), 6.74 (dd, J=8.8, 2.8 Hz, 1H), 6.84 (dd, J=9.0, 2.7 Hz, 1H), 6.89 (d, J=2.7 Hz, 1H), 7.18 (d, J=2.7 Hz, 1H), 7.52 (dd, J=9.0, 2.7 Hz, 1H), 7.73 (dd, J=8.9, 3.6 Hz, 1H). $^{13}$C NMR (126 MHz, $CDCl_3$) δ 55.98, 71.62, 113.39, 114.62, 114.71, 115.69, 118.07, 118.64, 119.15, 127.23, 140.71, 143.14, 143.80, 144.01, 160.74, 161.82.

2-(2-bromo-4-hydroxyphenyl)-3-vinyl-2H-indazol-5-ol (Ind-Vinyl-o-Br) (29)

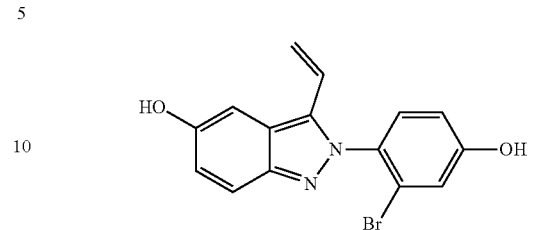

Ind-Vinyl-o-Br was prepared from the cyclization with Allyl-OH-Azo-o-Br as described to make the 5-OH-Indazol-o-Br-4-methoxy by using method 1 and subsequent demethylation with $BF_3$—$SMe_2$. $^1$H NMR (499 MHz, Chloroform-d+Methanol-$d_4$) 5.34 (dd, J=11.6, 0.9 Hz, 1H), 5.77 (dd, J=17.8, 1.0 Hz, 1H), 6.43 (dd, J=17.8, 11.7 Hz, 1H), 6.84 (dd, J=8.6, 2.6 Hz, 1H), 7.02 (dd, J=9.2, 2.3 Hz, 1H), 7.13 (s, 1H), 7.14 (s, 1H), 7.20 (d, J=8.6 Hz, 1H), 7.54 (d, J=9.2 Hz, 1H). ESI (m/z) 331.0: 333.0 (1:1, M+ +1). HRMS (ESI, M+ +1) Calcd. For $C_{16}H_{14}BrN_2O_2$ 345.0239, found 345.0225.

BB. Synthesis of 3-allyl-2-(2-bromo-4-hydroxyphenyl)-2H-indazol-5-ol (Ind-allyl-o-Br) (30)

3-(1-hydroxybut-3-en-1-yl)phenol

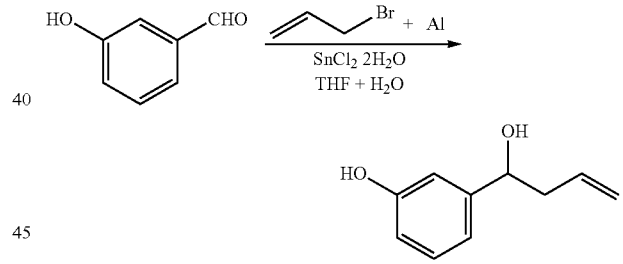

To the mixture of 3-hydroxybenzaldehyde (2.44 g, 20 mmol), allyl bromide (4.8 g, 40 mmol), $SnCl_2$-$2H_2O$ (7.8 g, 34.6 mmol), and aluminum foil (1.08 g) in THE (70 mL) was added 7 droplets of water according to the literature (Conxin Vilanova et al. Tetrahedron Letters 54 (2013) 6562-6567). The exothermic reaction was initiated when water was added dropwise. When the temperature of the reaction mixture was dropped down to rt, the solution was neutralized with 2.3 g NaOH and 1 g $NaHCO_3$ along with 200 mL water addition to the mixture. The extraction with EtOAc (50 mL×3), dried over $Na_2SO_4$, and evaporation provided 3.0 g of colorless solid. $^1$H NMR (500 MHz, Chloroform-d+Methanol-$d_4$) δ 2.45 (t, J=6.8 Hz, 2H), 4.61 (t, J=6.5 Hz, 1H), 5.06 (dd, J=18.7), 5.09 (d, J=11.0 Hz, 1H), Hz 5.76 (ddt, J=17.2, 10.2, 7.0 Hz, 1H), 6.71 (dd, J=8.0, 2.5 Hz, 1H), 6.75-6.85 (m, 2H), 7.14 (t, J=7.8 Hz, 1H). $^{13}$C NMR (126 MHz, $CDCl_3$) δ 43.64, 73.57, 112.77, 114.73, 117.66, 117.99, 129.64, 134.79, 145.80, 156.95.

4-((2-bromo-4-methoxyphenyl)diazenyl)-3-(1-hydroxybut-3-en-1-yl)phenol (1-Butenyl-OH-Azo-o-Br)

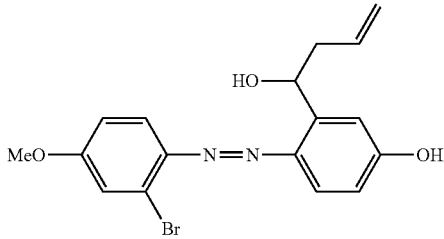 [SMILES: C=CCC(O)c1cc(O)ccc1N=Nc1ccc(OC)cc1Br]

1-Butenyl-OH-Azo-o-Br was obtained from the reaction with p-methoxy-2-bromoaniline (808 g, 4.00 mmol), NaNO$_2$ (284 mg, 4.16 mmol), 3-(1-hydroxybut-3-en-1-yl)phenol (0.656 g, 4.00 mmol) in 98% yield as yellowish solid as described to make Azo-o-Cl compound. $^1$H NMR (500 MHz, Methanol-d$_4$) δ 2.53 (q, J=7.6, 7.1 Hz, 2H), 3.84 (s, 3H), 4.98 (d, J=22.9 Hz, 1H), 5.03 (d, J=13.6 Hz, 1H), 5.68 (t, J=6.4 Hz, 1H), 5.81 (dt, J=17.3, 8.3 Hz, 1H), 6.75 (dd, J=8.8, 2.8 Hz, 1H), 6.90 (dd, J=9.0, 2.7 Hz, 1H), 7.03 (d, J=2.7 Hz, 1H), 7.23 (d, J=2.7 Hz, 1H), 7.57 (d, J=9.0 Hz, 1H), 7.72 (d, J=8.9 Hz, 1H). $^{13}$C NMR (126 MHz, CD$_3$OD) δ 44.28, 55.93, 69.92, 112.78, 114.66, 115.29, 117.31, 118.10, 118.35, 118.60, 127.22, 135.03, 142.81, 144.06, 145.69, 160.69, 161.81.

3-allyl-2-(2-bromo-4-hydroxyphenyl)-2H-indazol-5-ol (Ind-allyl-o-Br) (30)

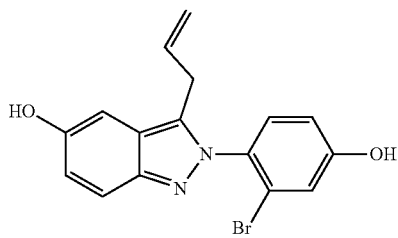 [SMILES: C=CCc1c2cc(O)ccc2nn1-c1ccc(O)cc1Br]

Ind-allyl-o-Br was prepared from the cyclization with 1-Butenyl-OH-Azo-o-Br as described to make the 5-OH-Indazol-o-Br-4-methoxy by using method 1 and subsequent demethylation with BF$_3$—SMe$_2$. $^1$H NMR (499 MHz, Chloroform-d+Methanol-d$_4$) 3.36 (dd, J=16.4, 6.7 Hz, 1H), 3.54 (dd, J=16.5, 6.1 Hz, 1H), 4.84-5.01 (m, 2H), 5.71-5.83 (m, 1H), 6.81 (dd, J=8.6, 1.8 Hz, 1H), 6.86 (d, J=1.8 Hz, 1H), 6.96 (dd, J=9.3, 2.3 Hz, 1H), 7.12 (d, J=2.3, 1H), 7.15 (d, J=8.6 Hz, 1H), 7.46 (d, J=9.3 Hz, 1H). ESI (m/z) 345.0: 347.0 (1:1, M$^+$+1). HRMS (ESI, M$^+$+1) Calcd. for C$_{15}$H$_{12}$BrN$_2$O$_2$ 333.0082, found 333.0086.

CC. Synthesis of 3-(hydroxymethyl)-2-(4-hydroxyphenyl)-2H-indazol-5-ol (Ind-CH2OH) (31)

3-bromo-5-((tert-butyldimethylsilyl)oxy)-2-(4-((tert-butyldimethylsilyl)oxy)phenyl)-2H-indazole (diTBDS-IndBr)

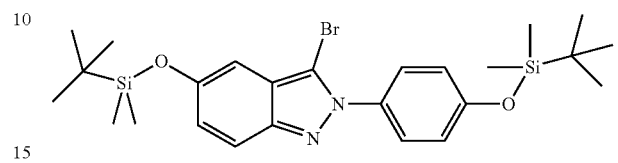

diTBDS-IndBr (115 mg) was obtained from the reaction of IndBr (66 mg, 0.21 mmol) with tert-butyldimethylsilyl chloride as described to make diTBDS-IndCl-o-Br. $^1$H NMR (500 MHz, Chloroform-d) δ 0.27 (s, 12H), 1.03 (s, 9H), 1.04 (s, 9H), 6.85 (d, J=2.2 Hz, 1H), 6.96-7.02 (m, 3H), 7.51 (d, J=8.8 Hz, 2H), 7.62 (d, J=9.2 Hz, 1H). $^{13}$C NMR (126 MHz, CDCl$_3$) δ -4.13, 18.50, 25.90, 25.99, 104.83, 105.27, 119.52, 120.62, 123.28, 125.70, 127.53, 133.17, 146.18, 151.47, 156.62.

5-((tert-butyldimethylsilyl)oxy)-2-(4-((tert-butyldimethylsilyl)oxy)phenyl)-2H-indazole-3-carbaldehyde (diTBDS-Ind-CHO)

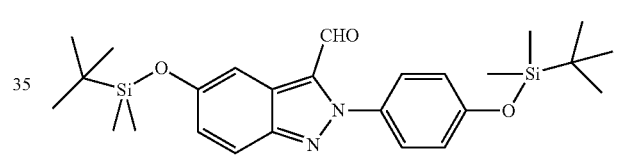

diTBDS-Ind-CHO was obtained from the reaction of diTBDS-IndBr with 1.6 M n-BuLi in Hexane using the procedure to prepare for diTBDS-IndCl-o-CHO. $^1$H NMR (499 MHz, Chloroform-d) δ 7.00-7.07 (m, 2H), 7.10 (dd, J=9.2, 2.3 Hz, 1H), 7.53 (d, J=8.8 Hz, 2H), 7.65 (dd, J=2.3, 0.8 Hz, 1H), 7.80 (dd, J=9.1, 0.7 Hz, 1H), 10.05 (s, 1H). $^1$H NMR (499 MHz, Chloroform-d) δ 0.29 (s, 6H), 0.31 (s, 6H), 1.05 (s, 9H), 1.06 (s, 9H), 7.05 (d, J=8.8 Hz, 2H), 7.10 (dd, J=9.2, 2.3 Hz, 1H), 7.53 (d, J=8.8 Hz, 2H), 7.65 (dd, J=2.3, 0.8 Hz, 1H), 7.80 (dd, J=9.1, 0.7 Hz, 1H), 10.05 (s, 1H). $^{13}$C NMR (126 MHz, CDCl$_3$) δ -4.12, 18.52, 25.89, 25.97, 107.45, 120.08, 121.12, 124.77, 125.29, 127.73, 131.96, 132.61, 145.29, 155.44, 157.39, 180.29.

4-(5-acetoxy-3-formyl-2H-indazol-2-yl)phenyl acetate (diAc-Ind-CHO)

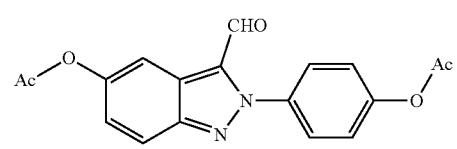 [SMILES: "Ac" ; O=Cc1c2cc(O)ccc2nn1-c1ccc(O)cc1 ; "Ac"]

diAc-Ind-CHO was prepared from the treatment of diTBDS-Ind-CHO with 1M TBAF in THF solution and subsequent treatment with Ac$_2$O and pyridine using the same method to make diTBDS-Ind-CHO. ¹H NMR (499 MHz, Chloroform-d) δ 2.38 (s, 3H), 2.39 (s, 3H), 7.24 (dd, J=9.2, 2.2 Hz, 1H), 7.39 (d, d, J=8.8 Hz, 2H), 7.70 (d, J=8.8 Hz, 2H), 7.92 (dd, J=9.2, 0.8 Hz, 1H), 8.03 (dd, J=2.2, 0.8 Hz, 1H), 10.11 (s, 1H). ¹³C NMR (126 MHz, CDCl₃) δ 21.35, 21.38, 112.55, 120.30, 123.17, 123.77, 124.47, 127.58, 132.89, 136.25, 146.90, 149.97, 152.05, 169.11, 169.82, 179.81.

3-(hydroxymethyl)-2-(4-hydroxyphenyl)-2H-indazol-5-ol (Ind-CH2OH) (31)

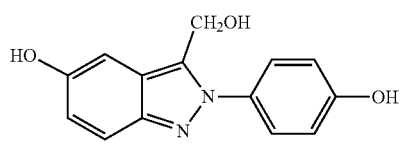 [SMILES: OCc1c2cc(O)ccc2nn1-c1ccc(O)cc1]

Ind-CH2OH was obtained from the reaction of diAc-Ind-CHO with 10 eq. NaBH₄ in THF-water mixture. ¹H NMR (499 MHz, Chloroform-d+Methanol-d₄) δ 4.76 (s, 2H), 6.89 (d, J=8.7 Hz, 2H), 6.94 (d, J=1.4 Hz, 1H), 6.97 (dd, J=9.3, 2.1 Hz, 1H), 7.42 (d, J=8.7 Hz, 2H), 7.50 (d, J=9.1 Hz, 1H). ESI (m/z) 257.0921 (M⁺+1). HRMS (ESI, M⁺+1) Calcd. for C₁₄H₁₂ClN₂O₃ 257.0926, found 257.0921.

DD. Synthesis of 3-chloro-2-(4-hydroxy-2-(hydroxymethyl)phenyl)-2H-indazol-5-ol (IndCl-o-CH2OH) (32)

2-(2-bromo-4-((tert-butyldimethylsilyl)oxy)phenyl)-5-((tert-butyldimethylsilyl)oxy)-3-chloro-2H-indazole (diTBDS-IndCl-o-Br)

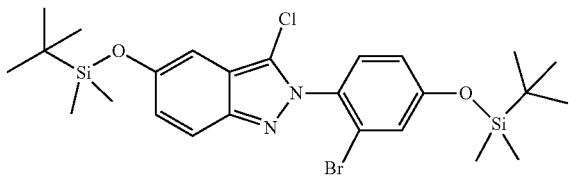 [SMILES: CC(C)(C)[Si](C)(C)Oc1ccc(-n2nc3ccc(O[Si](C)(C)C(C)(C)C)cc3c2Cl)c(Br)c1]

Protection of both phenolic OH in IndCl-o-Br (70 mg, 0.21 mmol) with t-butyldimethylsilyl chloride (80 mg, 0.52 mmol) and imidazole (54.4 mg, 0.80 mmol) in DMF (2 mL) afforded diTBDS-IndCl-o-Br (110 mg). ¹H NMR (499 MHz, Chloroform-d) δ 0.29 (s, 6H), 0.30 (s, 6H), 1.04 (s, 9H), 1.06 (s, 9H), 6.90 (d, J=2.2 Hz, 1H), 6.95 (dd, J=8.6, 2.6 Hz, 1H), 7.02 (dd, J=9.2, 2.2 Hz, 1H), 7.25 (d, J=2.6 Hz, 1H), 7.36 (d, J=8.6 Hz, 1H), 7.62 (d, J=9.2 Hz, 1H). ¹³C NMR (126 MHz, CDCl₃) δ −4.12, 18.47, 25.82, 25.97, 104.39, 119.26, 119.76, 119.81, 120.91, 122.49, 124.90, 125.98, 130.22, 131.59, 145.98, 151.37, 157.90.

5-((tert-butyldimethylsilyl)oxy)-2-(5-((tert-butyldimethylsilyl)oxy)-3-chloro-2H-indazol-2-yl)benzaldehyde (diTBDS-IndCl-o-CHO)

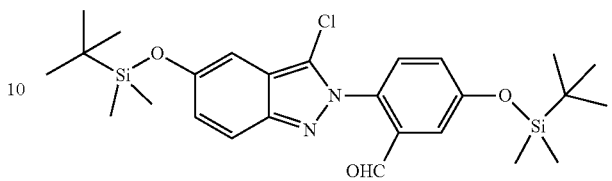

diTBDS-IndCl-o-Br (110 mg, 0.19 mmol) in the mixture of diethyl ether and THF (3 mL, 3:1) was treated with n-BuLi (130 μL of 1.6 M in n-hexane) for 30 min at −78° C. Once the bromo compound disappeared on SiO₂ TLC with n-Hexane eluent, dried DMF (196 μL, 0.29 mmol) in dried diethyl ether (500 μL) was added and stirred for 1 hr at the same temperature. The reaction mixture was quenched with H₂O (100 μL), concentrated with nitrogen stream, and loaded onto SiO₂ Preparative TLC plate (20×20 cm, 5% EtAOc-n-Hexane eluent) to afford 90 mg diTBDS-IndCl-o-CHO. ¹H NMR (499 MHz, Chloroform-d) δ 0.29 (s, 6H), 0.31 (s, 6H), 1.05 (s, 9H), 1.06 (s, 9H), 6.90 (d, J=2.3, 1H), 7.04 (dd, J=9.2, 2.3 Hz, 1H), 7.23 (dd, J=8.6, 2.8 Hz, 1H), 7.47 (d, J=8.6 Hz, 1H), 7.53 (d, J=2.8 Hz, 1H), 7.61 (dd, J=9.2 Hz, 1H), 9.53 (s, 1H). ¹³C NMR (126 MHz, CDCl₃) δ −4.16, 18.48, 25.83, 25.95, 104.22, 118.98, 119.67, 119.85, 120.80, 126.09, 126.54, 129.71, 133.43, 133.75, 146.18, 151.81, 157.54, 188.70.

(5-((tert-butyldimethylsilyl)oxy)-2-(5-((tert-butyldimethylsilyl)oxy)-3-chloro-2H-indazol-2-yl)phenyl)methanol (diTBDS-IndCl-o-CH2OH)

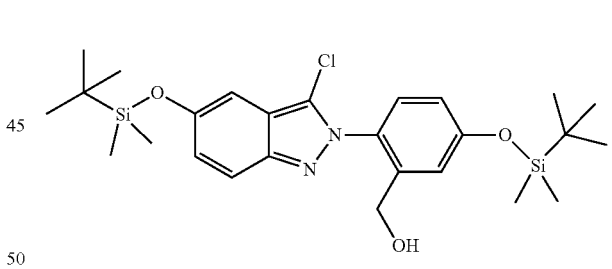

diTBDS-IndCl-o-CHO (15 mg, 0.029 mmol) was dissolved into THF (1 mL). To this mixture was added NaBH₄ (5 mg, 0.14 mmol) and subsequently was added water dropwise (100 μL). After 30 min, 1N HCl solution (100 μL) and EtOAc (1 mL) was added to the reaction mixture. The organic layer was washed with water (1 ml×5), dried over sodium sulfate, and evaporated to provide the title compound. ¹H NMR (499 MHz, Chloroform-d) δ 0.29 (s, 6H), 0.30 (s, 6H), 1.05 (s, 9H), 1.06 (s, 9H), 4.26 (s, 2H), 6.91 (d, J=2.2 Hz, 1H), 6.94 (dd, J=8.6, 2.8 Hz, 1H), 7.04 (dd, J=9.2, 2.3 Hz, 1H), 7.10 (d, J=2.7 Hz, 1H), 7.34 (d, J=8.6 Hz, 1H), 7.58 (d, J=9.2 Hz, 1H). ¹³C NMR (126 MHz, CDCl₃) δ −4.13, 18.47, 18.49, 25.87, 25.97, 62.24, 104.48, 119.34, 119.69, 119.77, 120.10, 122.20, 126.33, 128.81, 130.62, 139.77, 145.39, 151.58, 157.28.

3-chloro-2-(4-hydroxy-2-(hydroxymethyl)phenyl)-2H-indazol-5-ol (IndCl-o-CH2OH) (32)

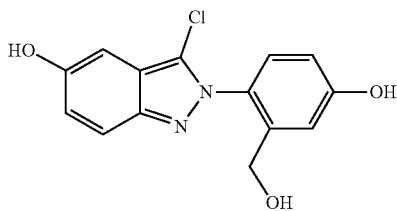 [SMILES: OCc1cc(O)ccc1-n1nc2ccc(O)cc2c1Cl]

Treatment of diTBDS-IndCl-o-CH2OH (10 mg, 0.019 mmol) with TBAF solution in THF (50 μL) at rt provided the title IndCl-o-CH2OH (4 mg). $^1$H NMR (499 MHz, Chloroform-d+Methanol-d$_4$) δ 4.13 (s, 2H), 6.76 (dd, J=2.3, 0.8 Hz, 1H), 6.81 (dd, J=8.5, 2.8 Hz, 1H), 7.00 (dd, J=9.3, 2.3 Hz, 1H), 7.03 (d, J=2.8 Hz, 1H), 7.13 (d, J=8.5 Hz, 1H), 7.44 (dd, J=9.3, 0.8 Hz, 1H). ESI (m/z) 291.0529 (M$^+$+1), 273.0426 (M$^+$+1-H$_2$O). HRMS (ESI, M$^+$+1) Calcd. for C$_{14}$H$_{12}$ClN$_2$O$_3$ 291.0536, found 291.0529.

EE. Synthesis of 3-(1,3-dithiolan-2-yl)-2-(4-hydroxyphenyl)-2H-indazol-5-ol (Ind-thiolane) (33)

4-(5-acetoxy-3-(1,3-dithiolan-2-yl)-2H-indazol-2-yl)phenyl acetate (diAc-Ind-thiolane)

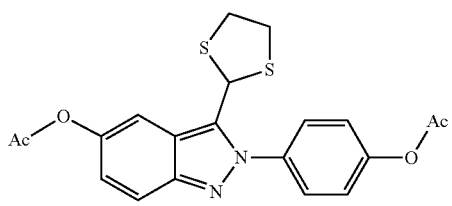 [SMILES: "Ac" ; Oc1ccc(-n2nc3ccc(O)cc3c2C2SCCS2)cc1 ; "Ac"]

diAc-Ind-thiolane was obtained from the reaction of diAc-Ind-CHO with 1,2-ethanedithiol in DCM in the presence of catalytic BF$_3$ etherate at rt as described to make diAc-Ind-Cl-o-thiolane. $^1$H NMR (499 MHz, Chloroform-d) δ 2.37 (s, 3H), 2.39 (s, 3H), 3.36-3.48 (m, 2H), 3.59-3.73 (m, 2H), 5.97 (s, 1H), 7.11 (dd, J=9.2, 2.2 Hz, 1H), 7.33 (d, J=8.9 Hz, 2H), 7.63 (d, J=8.9 Hz, 2H), 7.74 (d, J=9.0 Hz, 1H), 7.83 (dd, J=2.2, 0.8 Hz, 1H). $^{13}$C NMR (126 MHz, CDCl$_3$) δ 21.40, 21.49, 40.95, 47.52, 47.54, 112.38, 119.54, 120.28, 122.90, 123.49, 127.64, 132.80, 136.77, 145.25, 147.53, 151.53, 169.31, 170.11.

3-(1,3-dithiolan-2-yl)-2-(4-hydroxyphenyl)-2H-indazol-5-ol (Ind-thiolane) (33)

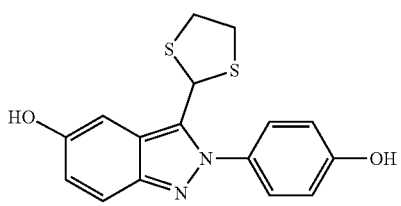 [SMILES: Oc1ccc(-n2nc3ccc(O)cc3c2C2SCCS2)cc1]

Ind-thiolane was obtained from the treatment of diAc-Ind-thiolane with K$_2$CO$_3$ in MeOH as described to make IndCl-o-thiolane. $^1$H NMR (499 MHz, Chloroform-d+Methanol-d$_4$) δ 3.27-3.33 (m, 2H), 3.50-3.58 (m, 2H), 6.89 (d, J=8.8 Hz, 2H), 6.96 (dd, J=9.2, 2.3 Hz, 1H), 7.24-7.28 (m, 3H), 7.45 (dd, J=9.3, 0.8 Hz, 1H). ESI (m/z) 331.0570 (M$^+$+1). HRMS (ESI, M$^+$+1) Calcd. for C$_{16}$H$_{15}$N$_2$O$_2$S$_2$ 331.0575, found 331.0570.

FF. Synthesis of 2-(2-(1,3-dithiolan-2-yl)-4-hydroxyphenyl)-3-chloro-2H-indazol-5-ol (IndCl-o-thiolane) (34)

2-(4-acetoxy-2-formylphenyl)-3-chloro-2H-indazol-5-yl acetate (diAc-IndCl-o-CHO)

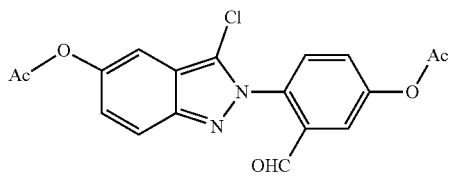 [SMILES: "Ac" ; CC(=O)Oc1ccc(-n2nc3ccc(O)cc3c2Cl)c(C=O)c1]

The sequential treatment of diTBDS-IndCl-o-CHO (20 mg, 0.038 mmol) with 1M TBAF in THF (70 μL) and Ac$_2$O and pyridine (2:1, 200 μL) afforded diAc-IndCl-o-CHO (14 mg). $^1$H NMR (499 MHz, Chloroform-d) δ 2.38 (s, 3H), 2.40 (s, 3H), 7.16 (dd, J=9.3, 2.1 Hz, 1H), 7.39 (dd, J=2.2, 0.8 Hz, 1H), 7.57 (dd, J=8.6, 2.6 Hz, 1H), 7.63 (d, J=8.6 Hz, 1H), 7.74 (d, J=8.6 Hz, 2H), 7.87 (d, J=2.7 Hz, 1H), 9.60 (s, 1H). $^{13}$C NMR (126 MHz, CDCl$_3$) δ 21.31, 21.38, 109.94, 119.29, 120.09, 121.98, 125.11, 127.72, 129.56, 133.35, 137.01, 146.88, 147.55, 152.14, 168.86, 169.96, 187.55. ESI (m/z) 373.05 (M$^+$+1). HRMS (ESI, M$^+$+1) Calcd. for C$_{18}$H$_{13}$ClN$_2$O$_5$ 373.0593, found 373.0596.

2-(4-acetoxy-2-(1,3-dithiolan-2-yl)phenyl)-3-chloro-2H-indazol-5-yl acetate (diAc-Ind-Cl-o-thiolane)

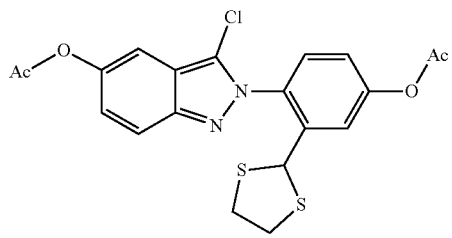 [SMILES: CC(=O)Oc1ccc(-n2nc3ccc(OC(C)=O)cc3c2Cl)c(C2SCCS2)c1]

To the mixture of diAc-IndCl-o-CHO (20 mg, 0.054 mmol) and 1,2-ethanedithiol (10 mg, 0.11 mmol) in dichloromethane (1 mL) was added one drop of BF$_3$-etherate at rt. After 30 min, the solution was dried out with nitrogen stream to get diAc-Ind-Cl-o-thiolane (24 mg). $^1$H NMR (499 MHz, Chloroform-d) δ 2.38 (s, 3H), 2.39 (s, 3H), 3.21-3.29 (m, 2H), 3.38-3.48 (m, 2H), 5.34 (s, 1H), 7.13 (dd, J=9.3, 2.6 Hz, 1H), 7.23 (dd, J=8.5, 2.6 Hz, 1H), 7.33 (d, J=8.5 Hz, 1H), 7.39 (dd, J=2.4, 0.8 Hz, 1H), 7.76 (dd, J=9.3, 0.8 Hz, 1H), 7.82 (d, J=2.6 Hz, 1H). $^{13}$C NMR (126 MHz, CDCl$_3$) δ 21.40, 21.46, 40.33, 49.78, 110.10, 118.76, 120.26, 121.86, 122.58, 122.94, 124.45, 129.03, 133.55, 141.39, 146.49, 147.38, 152.29, 168.99, 170.15.

2-(2-(1,3-dithiolan-2-yl)-4-hydroxyphenyl)-3-chloro-2H-indazol-5-ol (IndCl-o-thiolane) (34)

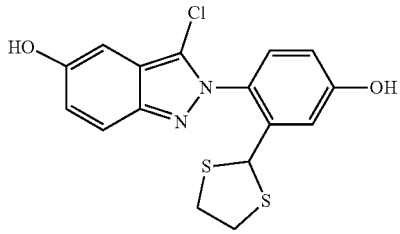 [SMILES: Oc1ccc(-n2nc3ccc(O)cc3c2Cl)c(C2SCCS2)c1]

diAc-Ind-Cl-o-thiolane (10 mg, 0.022 mmol) was dissolved into MeOH (500 μL) and treated with $K_2CO_3$ (20 mg, 0.15 mmol) at rt. After 20 min, the reaction mixture was treated with 1 N HCl (80 μL), extracted with EtOAc (1 mL×3), washed with water (1 mL×5), dried over $Na_2SO_4$, and evaporated to provide the title compound (6.7 mg). $^1$H NMR (499 MHz, Chloroform-d+Methanol-$d_4$) δ 3.09-3.15 (m, 2H), 3.30-3.36 (m, 2H), 5.08 (s, 1H), 6.74-6.78 (m, 2H), 6.98 (dd, J=9.3, 2.3 Hz, 1H), 7.02 (d, J=8.5 Hz, 1H), 7.36 (d, J=2.7 Hz, 1H), 7.47 (dd, J=9.3, 0.8 Hz, 1H). ESI (m/z) 365.02 (M$^+$+1). HRMS (ESI, M$^+$+1) Calcd. for $C_{16}H_{14}ClN_2O_2S_2$ 365.0185, found 365.0196.

GG. Synthesis of 4,4'-(5-hydroxy-2H-indazole-2,3-diyl)diphenol (Ind-PhOH) (35)

4-(5-acetoxy-3-(difluoromethyl)-2H-indazol-2-yl)phenyl acetate (diAc-Ind-CF2H)

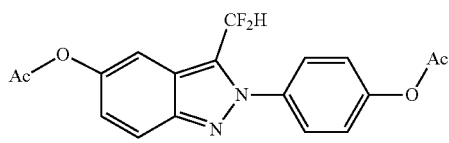 [SMILES: CC(=O)Oc1ccc(-n2nc3ccc(OC(C)=O)cc3c2C(F)F)cc1]

diAc-Ind-CF2H (8 mg) was obtained from the reaction of diAc-Ind-thiolane (82 mg, 0.20 mmol) with the mixture of 1,3-dibromo-5,5-dimethylhydantoin (170 mg, 0.59 mmol) and 70% HF in pyridine (pyridinium poly(hydrogen fluoride, 95 μL, 0.416 mmol, 3.84 eq. F$^-$) in DCM at −78° C. according to the literature (Susan C. Sondej et al., J. Org. Chem. 1986, 51, 3508-3513). $^1$H NMR (499 MHz, Chloroform-d) δ 2.38 (s, 3H), 2.39 (s, 3H) 6.93 (t, J=53.2 Hz, 1H), 7.18 (dd, J=9.3, 2.2 Hz, 1H), 7.36 (d, J=8.9 Hz, 2H), 7.63-7.64 (m, 1H), 7.66 (d, J=8.9 Hz, 2H), 7.84 (dd, J=9.3, 0.8 Hz, 1H). $^{19}$F NMR (470 MHz, Chloroform-d) δ −109.67 (d, J=53.1 Hz). ESI (m/z) 361.10 (M$^+$+1). HRMS (ESI) Calcd. for $C_{18}H_{15}F_2N_2O_4$ 361.1000, found 361.1000.

4-(5-methoxy-2-(4-methoxyphenyl)-2H-indazol-3-yl)phenol (diMe-Ind-PhOH)

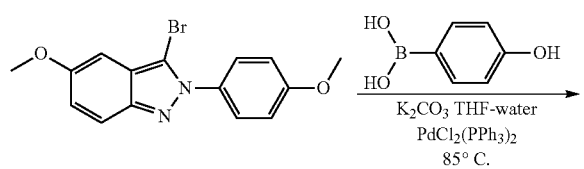

A mixture of diMe-IndBr (100 mg, 0.3 mmol), $K_2CO_3$ (41.44 mg, 0.30 mmol), and 4-hydroxyphenylboronic acid (55 mg, 0.40 mmol) in THF (20 mL) containing 200 μL water was purged with argon gas for 10 min. and to this mixture was added a catalytic amount of $PdCl_2(PPh_3)_2$ and stirred for 5 hr at 85° C. The reaction mixture was concentrated under vacuum and loaded onto $SiO_2$ preparative TLC (20×20 cm), developing with 2:1 ethyl acetate and n-hexane mixture to afford 43 mg of diMe-Ind-PhOH. $^1$H NMR (499 MHz, Methanol-$d_4$) δ 3.78 (s, 6H), 6.77-6.88 (m, 5H), 7.01 (dd, J=9.3, 2.3 Hz, 1H), 7.11 (d, J=8.6 Hz, 2H), 7.25 ((d, J=8.6 Hz, 2H), 7.57 (d, J=9.3 Hz, 1H). $^{13}$C NMR (126 MHz, CD$_3$OD) δ 55.60, 55.62, 97.00, 114.26, 115.98, 118.57, 121.25, 122.20, 127.25, 131.09, 133.40, 135.36, 145.52, 155.64, 157.29, 159.39.

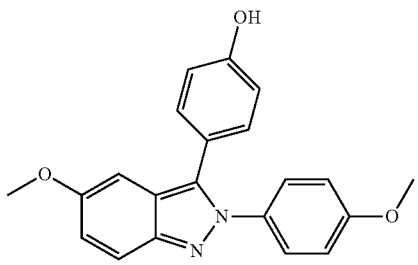

4,4'-(5-hydroxy-2H-indazole-2,3-diyl)diphenol (Ind-PhOH) (35)

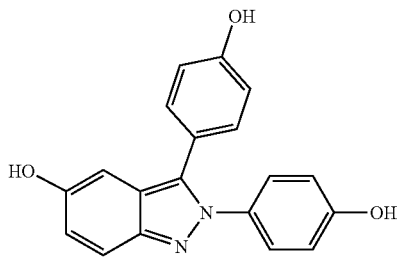 [SMILES: Oc1ccc(-c2c3cc(O)ccc3nn2-c2ccc(O)cc2)cc1]

Treatment of diMe-Ind-PhOH (10 mg, 0.03 mmol) with 20 eq. BF$_3$ SMe$_2$ in DCM afforded Ind-PhOH (6 mg). $^1$H NMR (499 MHz, Chloroform-d) δ 6.73-6.79 (m, 4H), 6.91 (dd, J=2.3, 0.8 Hz, 1H), 7.02 (dd, J=9.2, 2.3 Hz, 1H), 7.09 (d, J=8.7, Hz, 2H), 7.14 (d, J=8.7 Hz, 2H), 7.53 (dd, J=9.3, 0.8 Hz, 1H). $^{13}$C NMR (126 MHz, CD$_3$OD) δ 100.54, 115.69, 115.74, 118.16, 121.41, 121.47, 121.61, 127.37, 130.99, 132.42, 134.73, 145.13, 152.07, 157.07, 157.19. ESI (m/z) 319.1086 (M$^+$+1). HRMS (ESI, M$^+$+1) Calcd. for $C_{19}H_{15}N_2O_3$ 319.1083, found 319.1085.

HH. 3-allyl-2-(4-hydroxy-2-vinylphenyl)-2H-inda-zol-5-ol (Ind-Allyl-o-vinyl)

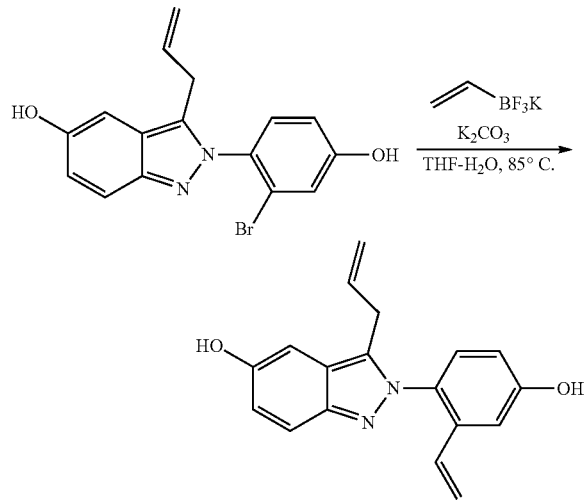

A mixture of Ind-allyl-o-Br (35.0 mg, 0.10 mmol), $K_2CO_3$ (14 mg), vinyltrifluoroborate potassium salt (20 mg, 0.15 mmol), and a catalytic amount of $PdCl_2(PPh_3)_2$ in THF (5 mL) and water (100 μL) under argon atmosphere was heated up for 4 hr at 85° C. in a sealed vial. The reaction mixture was diluted with deionized water (10 mL) and extracted with EtOAc (5 mL×3). The mixture was purified with silica gel preparative TLC (20×20 cm, EtOAc-n-Hexane (2:1)). $^1$H NMR (499 MHz, Chloroform-d) δ 3.34-3.51 (m, 2H), 4.84-4.99 (m, 2H), 5.09 (d, J=11.1 Hz, 1H), 5.57 (d, J=17.5 Hz, 1H), 5.65-5.77 (m, 1H), 5.86 (dd, J=17.5, 11.0 Hz, 1H), 6.77 (dd, J=8.5, 2.7 Hz, 1H), 6.87 (d, J=2.3 Hz, 1H), 6.99 (dd, J=9.2, 2.3 Hz, 1H), 7.06-7.11 (m, 2H), 7.47 (d, J=9.2 Hz, 1H). ESI (m/z) 293.1284 (M$^+$+1). HRMS (ESI, M$^+$+1) Calcd. for $C_{18}H_{17}N_2O_2$ 293.1290, found 293.1290.6.

6. Examples

Example 1. Biological Methods

Primary OPC Cultures: Primary OPCs, isolated from postnatal day P1 C57BL/6 male and female mouse cortices as described previously, were treated with 10 nM ligands in differentiating medium for 3 days (Tiwari-Woodruff et al., 2001; Tiwari-Woodruff et al., 2006). Primary OPC were cultured into 8-well chamber slides (three wells per condition, $2.5 \times 10^5$ cells/well) for three days to attach and five days in differentiating media (consisting of DMEM-F12 with triiodothyronine- and thyroxine-containing Sato as well as penicillin, streptomycin, insulin, N-acetyl-L-cysteine, forskolin, ciliary neurotrophic factor, neurotrophin-3, and platelet-derived growth factor receptor α (Tiwari-Woodruff et al., 2001)). A positive control (IndCl), a negative control (Vehicle consisting of the media+EtOH mixture used to dissolve IndCl), and a normal control (differentiating media alone) were used for comparison. At the end of the treatment period, cells were fixed, stained by immunocytochemistry (primary antibody polyclonal chicken myelin basic protein (MBP, Millipore AB9348), shown in green and co-stained with nuclear stain—DAPI shown in blue), and imaged with an Olympus BX61 confocal microscope (Olympus America Inc., Center Valley, Pa.) at 10× magnification (3 images per well). Cells were counted using the ImageJ multipoint tool, and counts were then divided by the image area (mm$^2$). Average cell density for each condition was then divided by the normal condition cell density. Analysis of OL differentiation consisted of counting the number of MBP+ cells and process extensions that were longer than the respective cell-body diameter and tracking the number of highly branched MBP+ cells (with three or more processes) (Monnerie et al., 2017). Statistics were performed using GraphPad Prism 6 Software (La Jolla, Calif.). One-way ANOVA with Tukey's posthoc test for multiple comparisons was used to generate p-values, and data are presented as mean SEM (with α≤0.05).

EAE induction: Active EAE was induced in eight-week-old female C57BL/6 mice as previously described (Kumar et al., 2013; Hasselmann et al., 2017) (one of three representative EAE experiments). Briefly, mice received two subcutaneous (s.c) injections, each consisting of MOG35-55 peptide (Mimotopes, Clayton, Victoria, Australia) emulsified with *M. butyricum*-containing complete Freund's adjuvant (BD Difco, Franklin Lakes, N.J.) supplemented with *M. tuberculosis* (BD Difco), followed by two intraperitoneal injections of *Bordetella pertussis* toxin (List Biological Laboratories, Campbell, Calif.). Mice were monitored daily in accordance with standard EAE clinical disease scoring scale modified from Pettinelli and McFarlin (Pettinelli and McFarlin, 1981; Hasselmann et al., 2017). Animals were maintained in accordance with guidelines set by the National Institute of Health and as mandated by the University of California Riverside Office of Research Integrity and the Institutional Animal Care and Use Committee (IACUC) in compliance with the American Association for Laboratory Animal Science (AALAS).

Treatment: Prophylactic 17β estradiol (E2) (Sigma-Aldrich; St. Louis, Mo.), therapeutic chloroindazole (IndCl) (De Angelis et al., 2005), and chloroindazole derivatives, synthesized as described herein, were dissolved in 10% ethanol and 90% Miglyol 812N (vehicle) (Cremer; Sasol, Germany). Positive control groups received a 0.1 ml subcutaneous (s.c.) injection at 0.05 mg/kg/day E2 at EAE day 0 (preEAE). Therapeutic treatment (s.c) with vehicle and various ERβ ligands at 5 mg/kg/day was initiated at EAE postinduction day 8 (postEAE; onset of clinical symptoms) and continued until day 30. Animals were euthanized according to the 2013 AVMA Guidelines on Euthanasia and were sacrificed on either on day 20-21 for flow cytometry, luminex analysis and immunohistochemistry or day 30 for electrophysiology after induction of disease. n=10 sex and age matched animals for normal, preE2, postE2, IndCl, IndCl-o-Cl, and IndCl-o-Me groups (60 mice in total).

Rotarod behavioral assay: Motor behavior was tested up to two times per week for each mouse using a rotarod apparatus (Med Associates, Inc., St. Albans, Vt.). Briefly, animals were placed on a rotating horizontal cylinder for a maximum of 200 seconds. The amount of time the mouse remained walking on the cylinder without falling was recorded. Each mouse was tested on a speed of 3-30 rpm and given three trials for any given day. The three trials were averaged to report a single value for an individual mouse, and averages were then calculated for all animals within a given treatment group (Moore et al., 2014). The first two trial days prior to immunization served as practice trials.

Histological Preparation of Tissues: Mice were deeply anesthetized by isoflurane (Piramal Healthcare) inhalation and perfused transcardially with phosphate buffered saline (PBS), followed by 10% formalin (Thermo Fisher Scientific) to fix tissues. Brains and spinal cords were dissected and post-fixed in 10% formalin (Thermo Fisher Scientific) for 24 hours, then cryoprotected in 30% sucrose (EMD Millipore, Darmstadt, Germany) for 48 hours and embedded in gelatin for sectioning. Embedded brains and spinal cords were then cut into 40-μm coronal sections using an HM525 NX cryostat (Thermo Fisher Scientific). Sections were collected serially and stored in PBS with 1% sodium azide at 4° C. until staining by immunohistochemistry, following a previously described protocol (Crawford et al., 2010; Moore et al., 2014).

Immunohistochemistry: Before histological staining, 40-μm free floating sections were thoroughly washed with PBS to remove residual sodium azide (Crawford et al., 2010). Sections were permeabilized with 0.3% Triton X-100 in ix PBS and 15% normal goat serum (NGS). Myelination, gliosis and immune markers were visualized by the following primary antibodies at a concentration of 1:500 unless otherwise noted: chicken anti-myelin basic protein (MBP; polyclonal, EMD Millipore, Darmstadt, Germany), chicken anti-glial fibrillary acidic protein (GFAP; EMD Millipore, Darmstadt), rat anti-cluster of differentiation 45 (CD45; clone 30-F11, BD Biosciences, San Diego, Calif.), mouse anti-ionized calcium-binding adapter molecule 1/allograft inflammatory factor-1 (Iba1/AIF1; clone 20A12.1, EMD Millipore, Darmstadt, Germany), goat anti-CXCL1 (R&D systems; Minneapolis, Minn.) at 1:250 and mouse anti-adenomatous polyposis coli (CC-1; clone CC-1, Genetex, Irvine, Calif.). Secondary staining was performed using polyclonal fluorophore-conjugated antibodies from ThermoFisher Scientific at a concentration of 1:500 unless otherwise specified: goat anti-chicken Alexa Fluor® 555 (AF555), goat anti-rabbit Alexa Fluor® 647 (AF647), donkey anti-chicken IgY Cy3 (EMD Millipore), goat anti-rat IgG AF647, goat anti-rabbit IgG Cy3 (EMD Millipore), goat anti-mouse IgG2b AF647 and rabbit anti-goat AF647. Nuclei were counter stained with 4',6-Diamidino-2-phenylindole (DAPI, 2 ng/ml; Molecular Probes) for 10 minutes after incubation with secondary antibodies, and sections were mounted on glass slides, allowed to dry, and cover-slipped with Fluoromount G mounting medium (Thermo Fisher Scientific) for imaging.

Splenocyte Isolation & Cytokine Analysis: On day 20-21 after induction of EAE, spleens were harvested prior to transcardial perfusion. Spleens were dissected from anesthetized mice and mechanically dissociated into a single cell suspension in cold RPMI 1640 supplemented with pyruvate, L-glutamine, and 10% fetal bovine serum (henceforth referred to as RPMI). Red blood cells were lysed by incubation with ACK buffer (VWR), washed, counted, and resuspended in RPMI for cytokine analysis. Splenocytes were then stimulated with 25 μg/ml MOG35-55 and supernatants were collected 48 hours later (Khalaj et al., 2013; Moore et al., 2013). Levels of the anti-inflammatory cytokines: IL-10, IL-13, IL-4 and IL-5; pro-inflammatory cytokines IFNγ, IL-17, IL-1β TNFα, IL-6 and IL-2; and chemokines: CXCL1, CXCL10 were determined by Cytokine Mouse Magnetic Panel for Luminex (Thermo Fisher Scientific; Waltham, Mass.) and run on the xMAP MAGPIX 100™ instrument (Luminex Corporation, Austin, Tx) according to manufacturer's instructions.

Transmission Electron Microscopy: Mice were perfused with PBS as above followed by paraformaldehyde/glutaraldehyde to preserve ultrastructure and Epon embedded as previously described (Crawford et al., 2010). Serial ultrathin sections of Epon-embedded CC were stained with uranyl acetate-lead citrate were used for electron microscopy analysis (19). G-ratio was measured using Fiji v1.0 Software (NIH).

Confocal Microscopy: Thoracic spinal cord dorsal and ventral column sections, as well as CC were imaged using an Olympus BX61 confocal microscope (Olympus America Inc., Center Valley, Pa.) using a 10× and 40× objective. Z-stack projections were compiled using SlideBook 6 software (Intelligent Imaging Innovations, Inc., Denver, Colo.). Immunostaining was quantified using unbiased stereology (Crawford et al., 2010). All images (RGB) were Confocal converted to grayscale, split, and separated by color channel using imageJ version 2.2.0-rc-46/1.50 g (NIH). To avoid experimenter bias, auto-adjustment of brightness and contrast, as well as threshold of staining signal, was carried out by ImageJ. $MBP^+$, $GFAP^+$, $CD45^+$, $Iba1^+$, $CC1^+$, and $CXCL1^+$, staining intensity was measured as percent area of positive immunoreactivity within the region of interest and intensity of signal determined by ImageJ.

Electrophysiology: To assess functional conductivity across the CC, electrophysiological recordings of compound action potentials (CAPs) were measured as previously described (Crawford et al., 2009; Crawford et al., 2010). Coronal brain slices were prepared from adult (3 to 4 month old) C57BL/6 female mice. Briefly, mice were deeply anesthetized under isoflurane and decapitated. The brain was removed and submerged in partially frozen "slushy" solution of slicing buffer containing (in mM): 87 NaCl, 75 sucrose 2.5 KCl, 0.5 $CaCl_2$), 7 $MgCl_2$, 1.25 $NaH_2PO_4$, 25 $NaHCO_3$, 10 glucose, 1.3 ascorbic acid, 0.1 kynurenic acid, 2.0 pyruvate, and 3.5 MOPS, bubbled with 5% $CO_2$+95% $O_2$ (Lauderdale et al., 2015). Coronal slices (350 μm) were prepared using a Leica VT 1000S Vibratome (Bannockburn, Ill.) and subsequently incubated for 45 minutes at 35° C. in slicing buffer. Following incubation, slices were allowed to cool to room temperature for 15 minutes then transferred to ACSF (anterior cervical spine fixation) containing (in mM): 125 NaCl, 2.5 KCl, 2.5 $CaCl_2$), 1.3 $MgCl_2$, 1.25 $NaH_2PO_4$, 26.0 $NaHCO_3$, and 15 glucose, oxygenated with 5% $CO_2$+ 95% $O_2$. Slices were equilibrated in the standard ACSF for a minimum of 15-20 minutes prior to electrophysiological recordings. During electrophysiological recordings, slices were continuously perfused with oxygenated ACSF maintained at a flow rate of 1 mL/min. For recording CAPs, an Axon Digidata 1550 was used with a Multiclamp 700B Amplifier and PClamp 10.4 Software (Molecular Devices, Sunnyvale, Calif.). Continuous recordings for CC conduction experiments were low-pass filtered at 10 kHz and digitized at 200 kHz. All experiments were conducted at room temperature (24-26° C.). To stimulate the CC fiber tract, a concentric bipolar stimulating electrode (FHC Neural microTargeting Worldwide, Bowdoin, Me., USA) was placed approximately 1 mm away across from a recoding electrode (glass micropipette filled with ACSF) with a resistance of 1-3 MO. To elicit CAPs, an episodic stimulation protocol was created consisting of 8 consecutive sweeps, each 12 ms long, with a 5-sec delay between sweeps and an immediate stimulus (0.01 ms duration) after the start of each sweep (Crawford et al., 2009a). Stimulus intensity was adjusted manually using an ISO-Flex stimulator (A.M.P.I). Standardized input-output plots were generated in current clamp mode for each slice by averaging at least 4 consecutive sweeps together to reduce the signal-to-noise ratio. Brain slices that exhibited near zero voltage even when stimulated with the maximal current were not included in the analysis. Electrophysiology data were analyzed using Clampfit 10.4 software (Molecular Devices, Sunnyvale, Calif.) and OriginPro 2016 64 Bit (OriginLab Corporation)

Statistical Analysis: All statistics were performed using Prism 6 software (GraphPad Software, La Jolla, Calif.). Differences in EAE clinical scores were determined by two-way unbalanced ANOVA with Dunnett's multiple comparisons test (Hasselmann et al., 2017). Luminex data and immunohistochemistry data were analyzed either by ordinary one-way ANOVA with Dunnett's multiple comparisons test if data satisfied assumptions of normal distribution (D'Agostino & Pearson omnibus normality test) and equal variances among all groups or Kruskal Wallis with Dunn's multiple comparisons test. CAP recording analysis was carried out per previously published work (Crawford et al., 2009b; Moore et al., 2014) using Clampfit 10.4 software (Molecular Devices, Sunnyvale, Calif.), OriginPro 2016 64 Bit (OriginLab Corporation) and GraphPad Prism 6 (GraphPad Software). The averaged mean amplitude was compared using one-way ANOVA with post hoc tests using Tukey's multiple comparison test. All data is presented as mean±SEM for two independent experiments. Differences were considered significant at *p≤0.05, p≤0.01, and *p≤0.001, ****p≤0.0001.

Pharmacokinetics: Following a single dose administration via s.c. injection or oral gavage at the doses (20 or 40 mg/kg) and with the vehicles (PEG400/Tween80/Povidone/0.5% Carboxymethyl Cellulose or 2-hydroxypropyl-beta-cyclodextrin 40% aqueous solution MW ~1540) indicated, multiple plasma samples were collected from each mouse (n=4 mice for each experiment) over the course of 48 h after the compound was administered at time zero. Compounds were quantified using LC-MS/MS. The data were fitted to a non-compartment PK model.

Figure 1B:
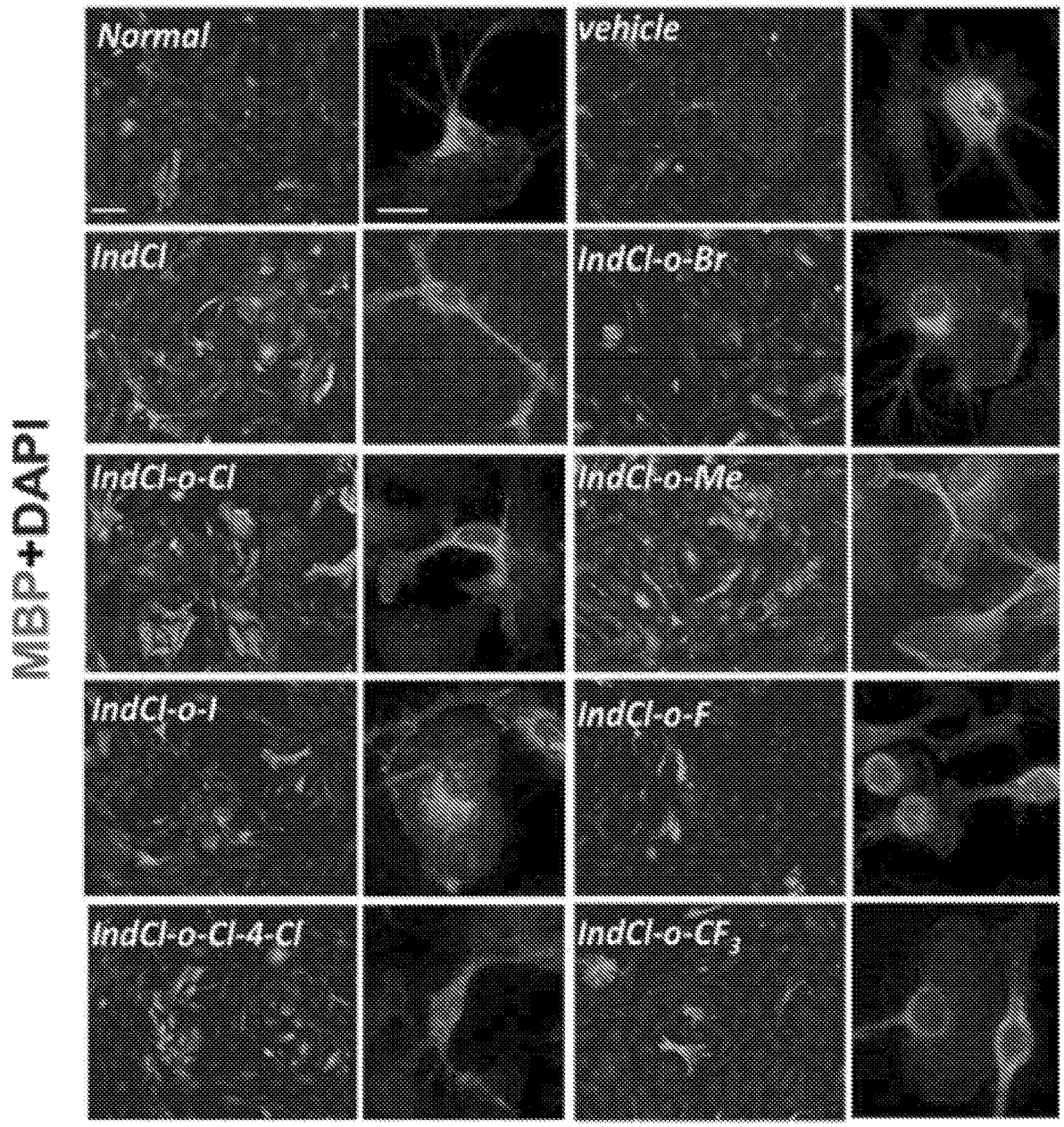
FIG. 1B shows representative images of primary oligodendrocyte and oligodendrocyte precursor cells (OL/OPCs) treated with differentiating media alone (normal media), vehicle, positive control IndCl, or the 7 different IndCl analogues. OLs were immunostained with myelin basic protein (MBP) and co-stained with nuclear stain DAPI.
Figure 1C:
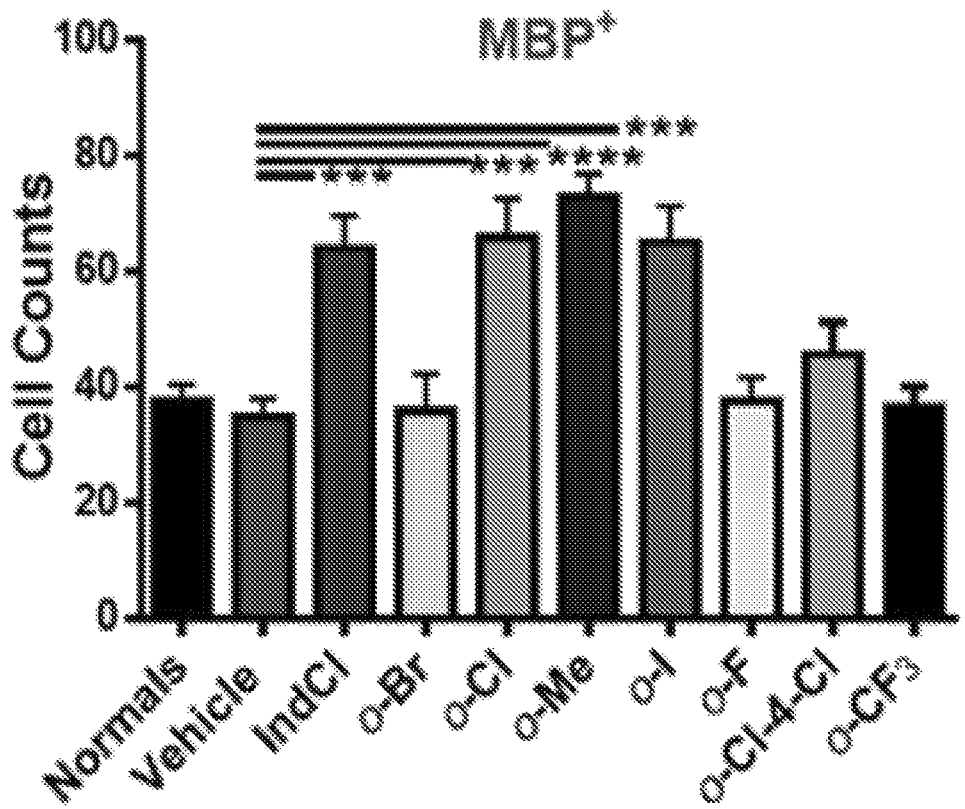
FIG. 1C shows bar graphs quantifying the number of MBP+ OLs for each treatment group in FIG. 1B. Analogues IndCl-o-Me, IndCl-o-Cl and IndCl-o-I showed a significant increase in number of MBP+ OLs that had an increase in the percentage of branched OLs, compared to vehicle-treated cells. There were 3 wells/treatment group. n=3 independent experiments were performed.
Figure 1D:
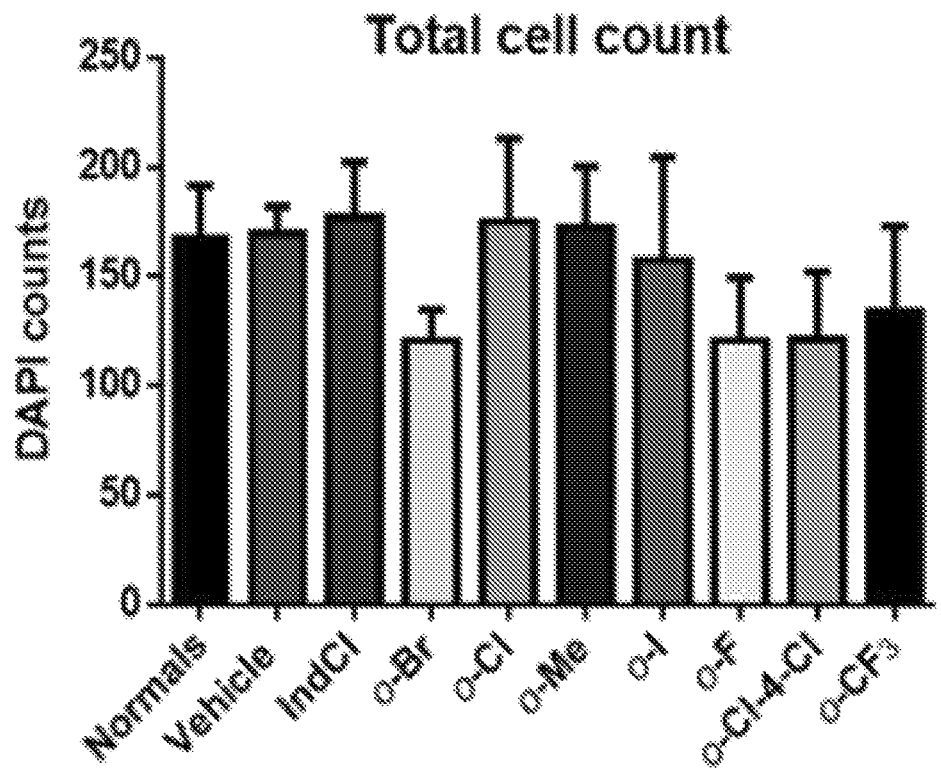
FIG. 1D shows bar graphs quantifying the number of total cells for each treatment group in FIG. 1B. No significant differences in total number of cells were observed between groups. There were 3 wells/treatment group. n=3 independent experiments were performed.

Example 2. Treatment with IndCl Analogues Stimulates Differentiation of OPCs In Vitro Primary OPC cultures were used as a convenient cell-based assay to characterize the proliferation and/or differentiation effects of the new IndCl analogues and to select those most suitable for more extensive studies to be done in comparison with the parental ligand, IndCl. 48 hours after plating OPCs, one of seven IndCl analogues (FIG. 1A) was added to differentiating media at a concentration of 10 nM (De Angelis et al., 2005; Saijo et al., 2011). OPCs were allowed to differentiate for 3 days in the presence of IndCl or analogues, at which point they were fixed, immunostained for OPC/OL markers, and quantified. Number of differentiated OLs immunostained with the myelin basic protein antibody in wells treated with IndCl, IndCl-o-Cl, IndCl-o-Me, and IndCl-o-I were significantly increased as compared to vehicle treated cultures (FIGS. 1B-1C). In addition, all four treatments also increased the number of complex branching cells, indicative of efficient OL differentiation (Tiwari-Woodruff et al., 2006). By contrast, the other 4 analogues did not affect cell differentiation as compared to vehicle-treated groups (FIGS. 1B-1C). The total number of cells in culture was not altered by any treatment (FIGS. 1B and 1D).

Example 3. IndCl Analogues Ameliorate EAE Severity More Effectively than IndCl and Improve Rotarod Performance without Affecting Uterine Weight IndCl has been shown to reduce motor disability in mice with EAE when administered prophylactically or therapeutically (Moore et al., 2014). Having established that IndCl-o-Cl and IndCl-o-Me exhibited comparable effects to IndCl in vitro, their impact was next evaluated in vivo using 8-week-old female C57BL/6 mice in which EAE had been induced following an established protocol (Hasselmann et al., 2017). As a positive control for non-ER isoform specific estrogenic signaling, mice were given prophylactic E2 subcutaneously at the time of initial immunization with MOG35-55 peptide, which continued throughout the course of experiments (preEAE+E2 group). All other groups received therapeutic daily subcutaneous doses of vehicle (postEAE+vehicle), E2 (postEAE+E2), IndCl (postEAE+IndCl), IndCl-o-Cl (postEAE+IndCl-o-Cl), or IndCl-o-Me (postEAE+IndCl-o-Me) that began at the onset of clinical symptoms and continued throughout the course of experiments. The timing of the different dosage regimens is illustrated schematically in FIG. 2A.

Figure 2A:
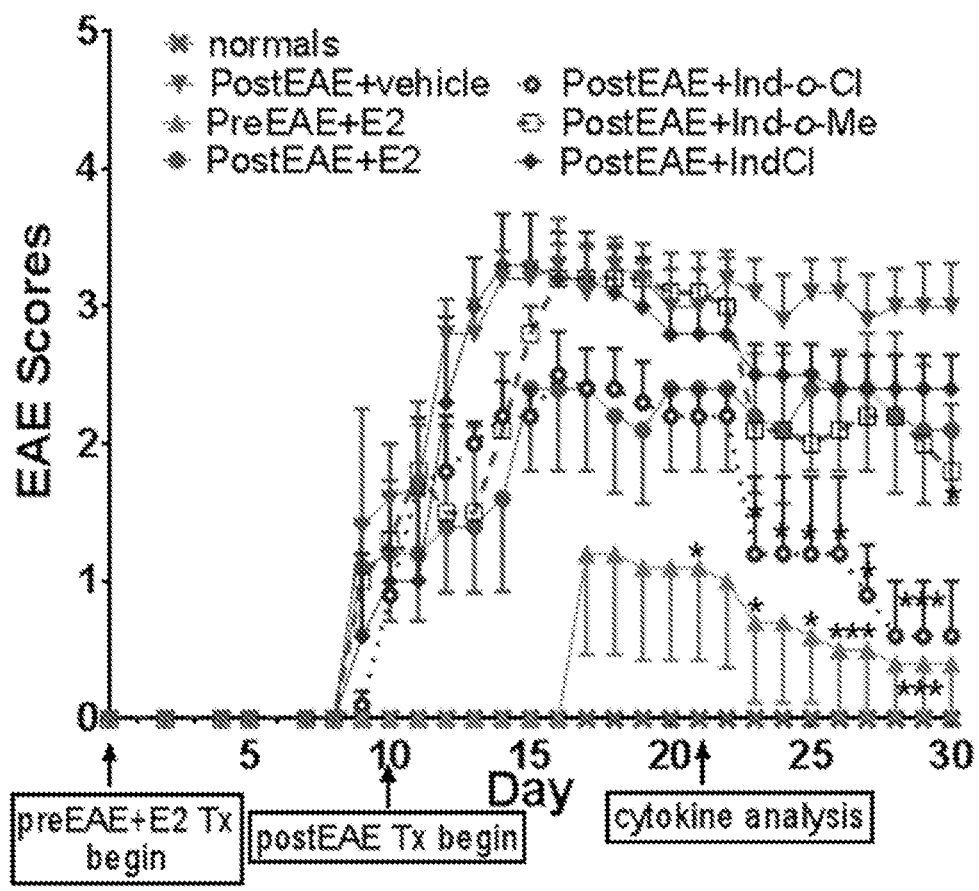
FIG. 2A shows a line graph of mice immunized with $MOG_{35-55}$ and their EAE (experimental autoimmune encephalomyelitis) scores. Normal mice did not receive $MOG_{35-55}$ or treatment. Therapeutic treatment with ERβ ligands, IndCl (5 mg/kg/d), IndCl-o-Cl (5 mg/kg/d), and IndCl-o-Me (5 mg/kg/d), and 17β-estradiol (E2; 0.05 mg/kg/d) began at the onset of clinical disease (day 8) until day 30. Prophylactic E2 (0.05 mg/kg/d) delayed onset of clinical disease. Vehicle-treated EAE mice displayed onset of clinical disease symptoms between days 7-10, with disease severity peaking around day 15. During peak disease, IndCl, IndCl-o-Cl and IndCl-o-Me treatment did not significantly affect EAE clinical symptoms, but reversed disease progression over time. One of two representative EAE experiments is shown. n=8-10 mice/group, Two-Way ANOVA with Dunnett's multiple comparisons test.

Disease course was greatly attenuated in mice that received prophylactic E2 treatment compared to those that received vehicle only, in which accumulating motor deficits appeared between post-immunization days 8-10 and persisted for the duration of experiments (FIG. 2A). Both therapeutic IndCl-o-Cl and IndCl-o-Me significantly reduced EAE clinical scores beginning at post-immunization day 23, roughly two weeks after initiation of treatment (FIG. 2A). This is consistent with previously published reports using IndCl and other ERβ ligands, which demonstrated significant protective effects at later stages of disease (Tiwari-Woodruff et al., 2007; Du et al., 2011; Kumar et al., 2013; Moore et al., 2014).

Figure 2B:
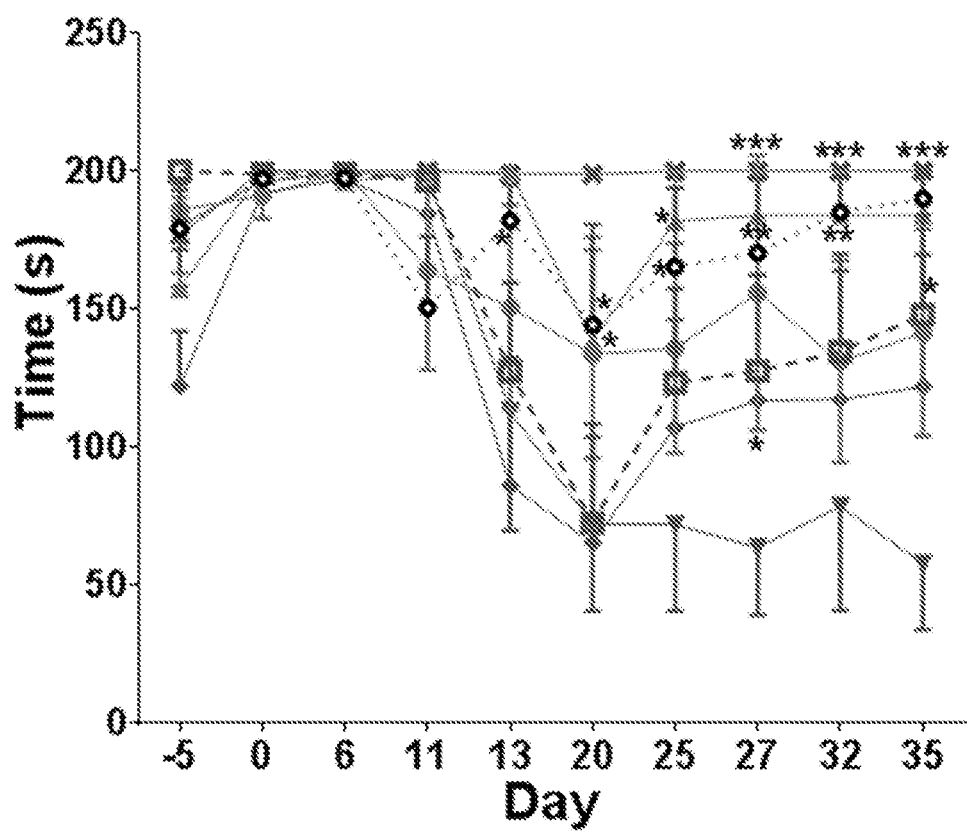
FIG. 2B shows a line graph assessing motor function. Mice were subjected to rotarod motor performance testing. Vehicle-treated EAE mice displayed an abrupt and consistent decrease in time (seconds) remaining on the rotarod. Treatment with IndCl-o-Cl treatment resulted in an increase of EAE mice remaining on the rotarod, representative of improved motor function. Data are representative of experiments repeated three times. n=8-10 mice/group, Ordinary One-Way ANOVA with Dunnett's multiple comparisons test.

As a complementary assay of motor function, mice were tested on a rotarod device following a previously described protocol (Moore et al., 2014). Normal mice and those that received prophylactic E2 did not fall off the rotarod within the time allotted, whereas vehicle and therapeutic E2 and IndCl treated mice had a tendency to fall from the cylinder abruptly. Both IndCl-o-Cl and IndCl-o-Me treatment improved rotarod performance compared to vehicle and IndCl by day 20 post-immunization. IndCl-o-Me treatment group exhibiting the greatest improvement in motor function. (FIG. 2B).

Figure 2C:
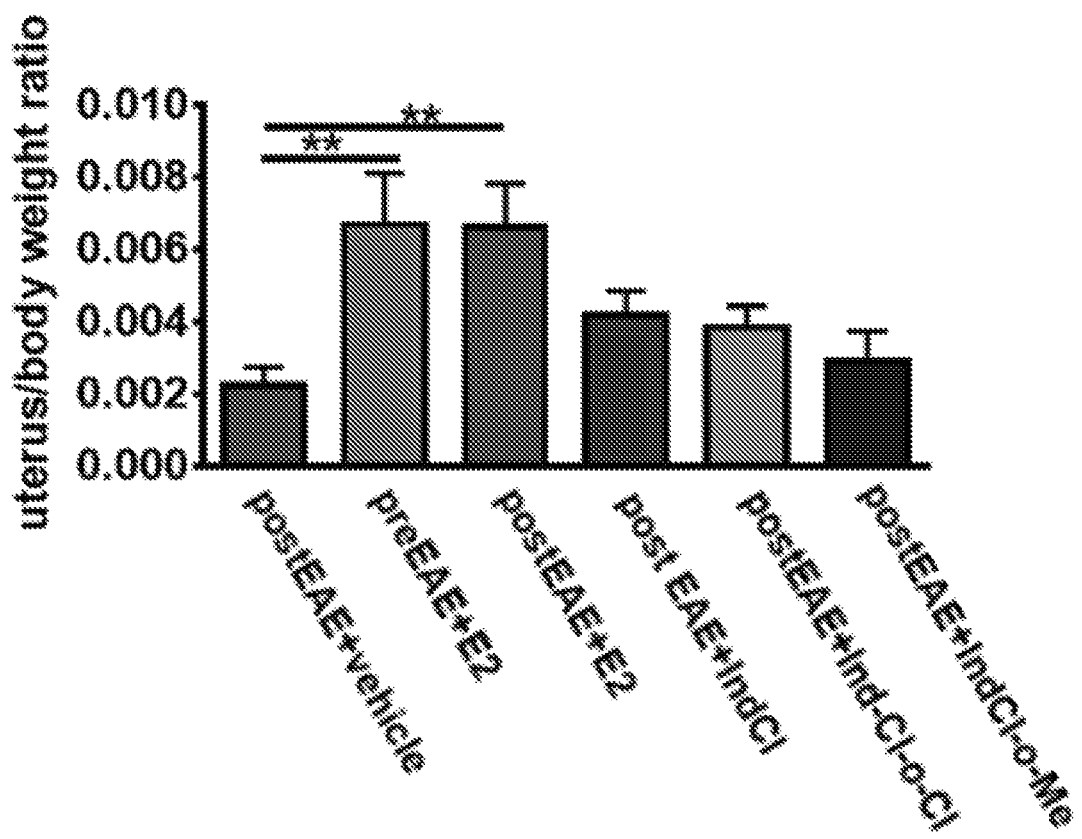
FIG. 2C shows the assessment of post-perfusion uterus to body weight ratios from normal and EAE mice treated with prophylactic E2 (postEAE+E2), or therapeutic E2 (PreEAE+E2), IndCl (PostEAE+IndCl), IndCl-o-Cl (PostEAE+Ind-Cl-o-Cl) and IndCl-o-Me (PostEAE+Ind-Cl-o-Me). Both prophylactic and therapeutic E2 treated female mice showed a fourfold increase of uterus to body weight ratio with no differences between all other treatment groups. n=8-10 mice/group, Kruskal Wallis and Ordinary One-Way ANOVA with Dunnett's multiple comparisons test analysis.

Estrogens increase uterine weight by acting primarily through ERα (Hewitt and Korach, 2003). In order to determine whether analogues tested possessed ERα signaling properties that could contribute to the observed improved motor performance, uterine weight was assessed. As expected, prophylactic and therapeutic E2 treatment significantly increased uterus to bodyweight ratios (FIG. 2C). In contrast, neither IndCl nor its analogues significantly increased this ratio (FIG. 2C).

Figure 3A:
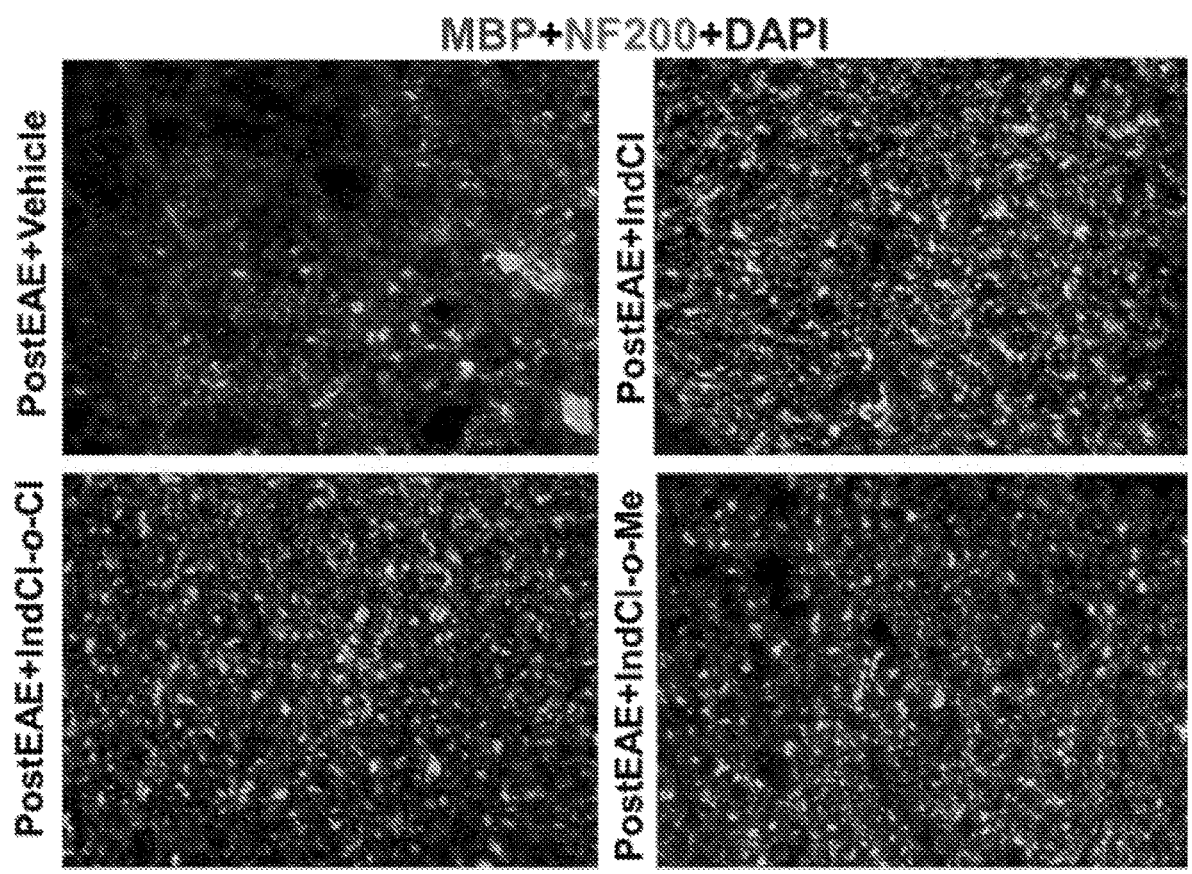
FIG. 3A shows fluorescence images of spinal cords in EAE animals treated with IndCl analogues. Representative 40× magnification coronal images of the ventral column of thoracic spinal cord (area delineated by square in FIG. 3B), showing axons stained with myelin basic protein (MBP), neurofilament 200 (NF200) and nuclear DAPI stain.
Figure 3B:
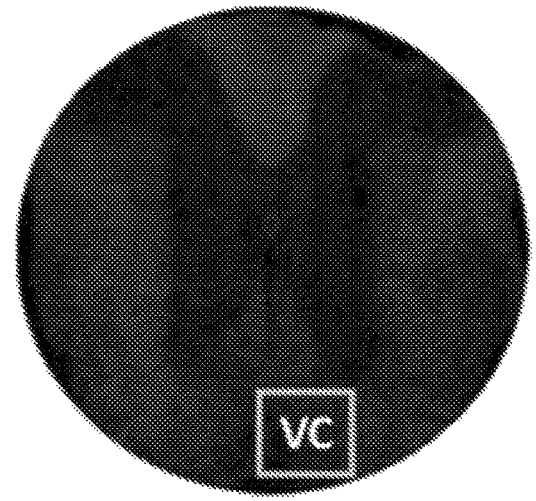
FIG. 3B shows a wide-field fluorescence coronal image of the ventral column of thoracic spinal cord in an EAE animals treated with IndCl analogues.
Figure 3C:
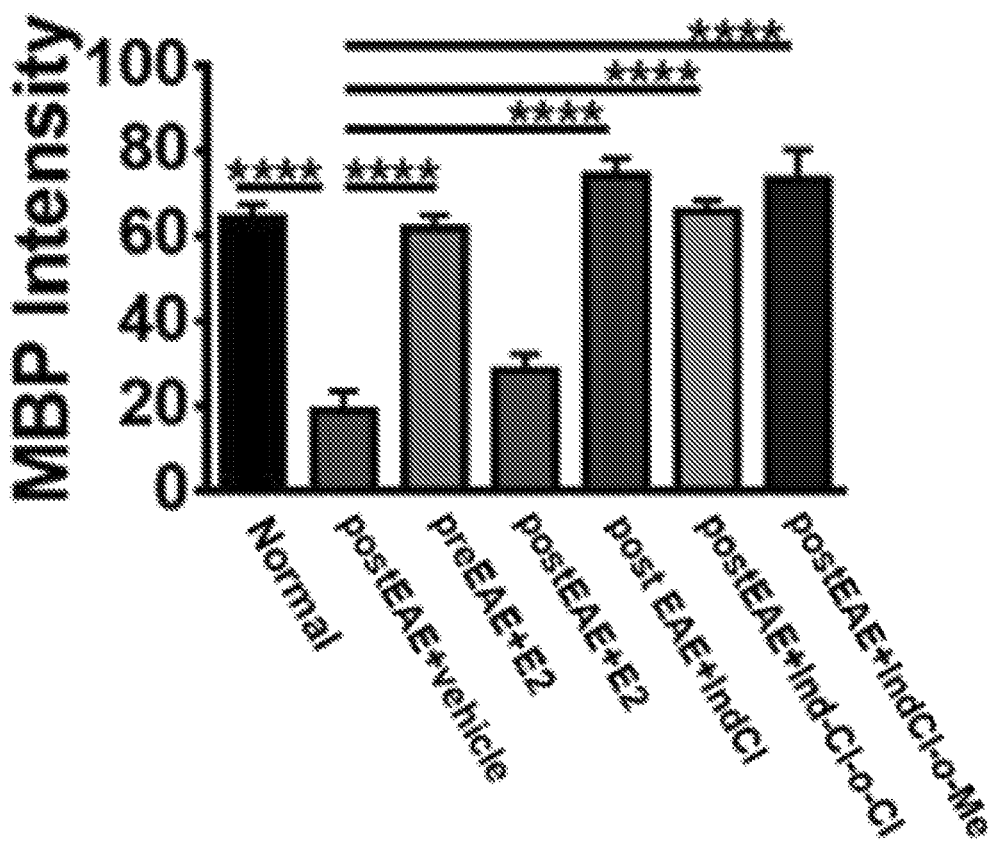
FIG. 3C shows the quantification of the relative fluorescence intensity of MBP from normal, vehicle, prophylactic E2, therapeutic IndCl, IndCl-o-Cl and IndCl-o-Me treated EAE mice. MBP intensity was significantly decreased in vehicle-treated EAE mice compared to normal controls but was maintained at near normal levels with prophylactic E2 and therapeutic IndCl, IndCl-o-Cl and IndCl-o-Me treatment. n=5 mice/group; Ordinary One-Way ANOVA with Dunnett's Multiple Comparisons Analysis.

Example 4. IndCl Analogues Increase Myelination in Spinal Cord White Matter During EAE Treatment with IndCl or other ERβ ligands improves myelination within CNS white tracts of mice with EAE (Khalaj et al., 2013; Kumar et al., 2013; Moore et al., 2014). To establish the pro-myelinating effects of the IndCl analogues tested, thoracic ventral column white matter was assessed for myelin basic protein (MBP) immunoreactivity. Mice that received vehicle treatment showed significantly reduced MBP staining intensity compared to normal, consistent with previous studies (Mangiardi et al., 2011; Moore et al., 2014; Hasselmann et al., 2017) (FIGS. 3A-3C). Therapeutic IndCl, IndCl-o-Cl, and IndCl-o-Me, as well as prophylactic E2 treatment, increased MBP staining intensity relative to vehicle, with all ligands tested having comparable remyelinating effects (FIGS. 3A-3C).

Example 5. IndCl Analogues Modify Peripheral Cytokine and Chemokine Responses in EAE During MS and EAE, peripherally activated leukocytes secrete inflammatory cytokines and chemokines as they migrate into the CNS, where they contribute to demyelination and axon damage (Fletcher et al., 2010). To characterize the effects of IndCl analogues on the peripheral immune response, splenocytes were isolated from mice 21 days post-immunization and stimulated ex vivo with MOG35-55 peptide for cytokine and chemokine analysis using a magnetic bead-based 20-plex cytokine/chemokine detection assay. Cytokines related to inflammation, CD4+ T cell polarization, immune regulation, and chemokines associated with OL apoptosis and myelination that were measured in collected supernatants are presented below.

Figure 4A:
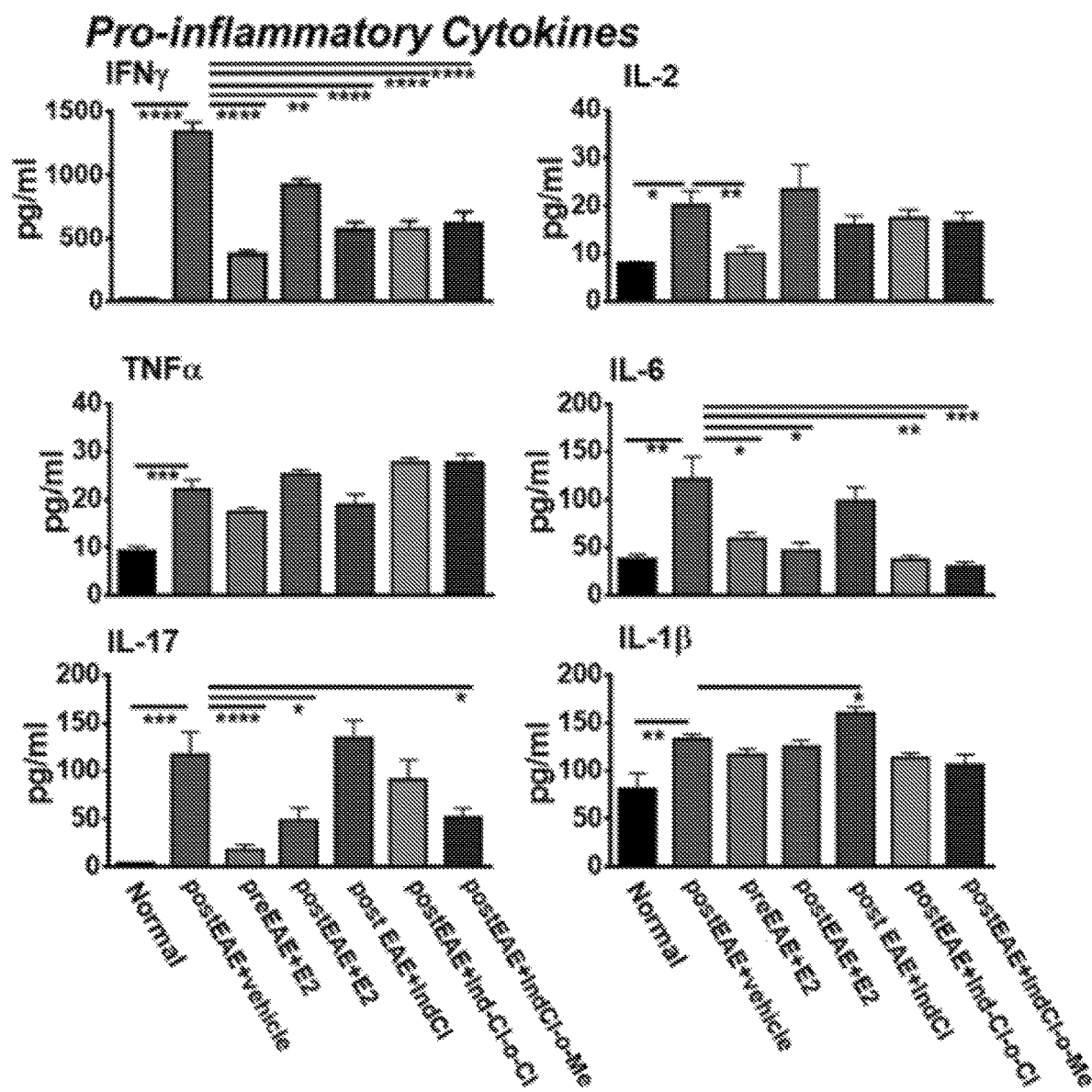
FIG. 4A. Cytokine production by MOG35-55-stimulated splenocytes was assessed from EAE mice killed on post-induction day 21. Vehicle-treated mice exhibited significantly increased levels of pro-inflammatory cytokines: IFNγ, IL-17, IL-1β, TNFα, IL-6 and IL-2 compared to normal controls. Prophylactic E2 significantly decreased IFNγ, IL-17, IL-6 and IL-2 levels compared to vehicle, with therapeutic E2 decreasing IFNγ, IL-17, IL-6 levels. Therapeutic IndCl treatment significantly decreased IFNγ levels compared to vehicle. Treatment with IndCl-o-Cl significantly decreased IFNγ and IL-6, with IndCl-o-Me significantly decreasing IFNγ, IL-17, IL-6 levels compared to vehicle. Data are representative of experiments repeated twice. n=4-6 mice/group, Kruskal Wallis Analysis with Dunn's Multiple Comparisons Analysis and Ordinary One-Way ANOVA with Dunnett's Multiple Comparisons Analysis.

Pro-inflammatory Cytokines (FIG. 4A): As expected, splenocytes from vehicle-treated mice exhibited greater production of IL-1β, IL-2, IL-6, IL-17, IFNγ, and TNFα relative to normal. Prophylactic E2 reduced IL-2, IL-6, IL-17, and IFNγ concentrations, but had no effect on IL-1β or TNFα, whereas therapeutic E2 reduced IL-6, IL-17, and IFNγ only. IndCl and both the o-Me and o-Cl analogues decreased IFNγ concentrations in supernatants relative to vehicle, while decreased IL-6 production was observed in splenocytes of all treatment groups except for IndCl. IndCl-o-Me stood out among ERβ ligands tested as also reducing IL-17 production. None of the ERβ ligands included in this study affected IL-2 or TNFα. Interestingly, IndCl treatment alone led to increased IL-1β production compared to vehicle.

Figure 4B:
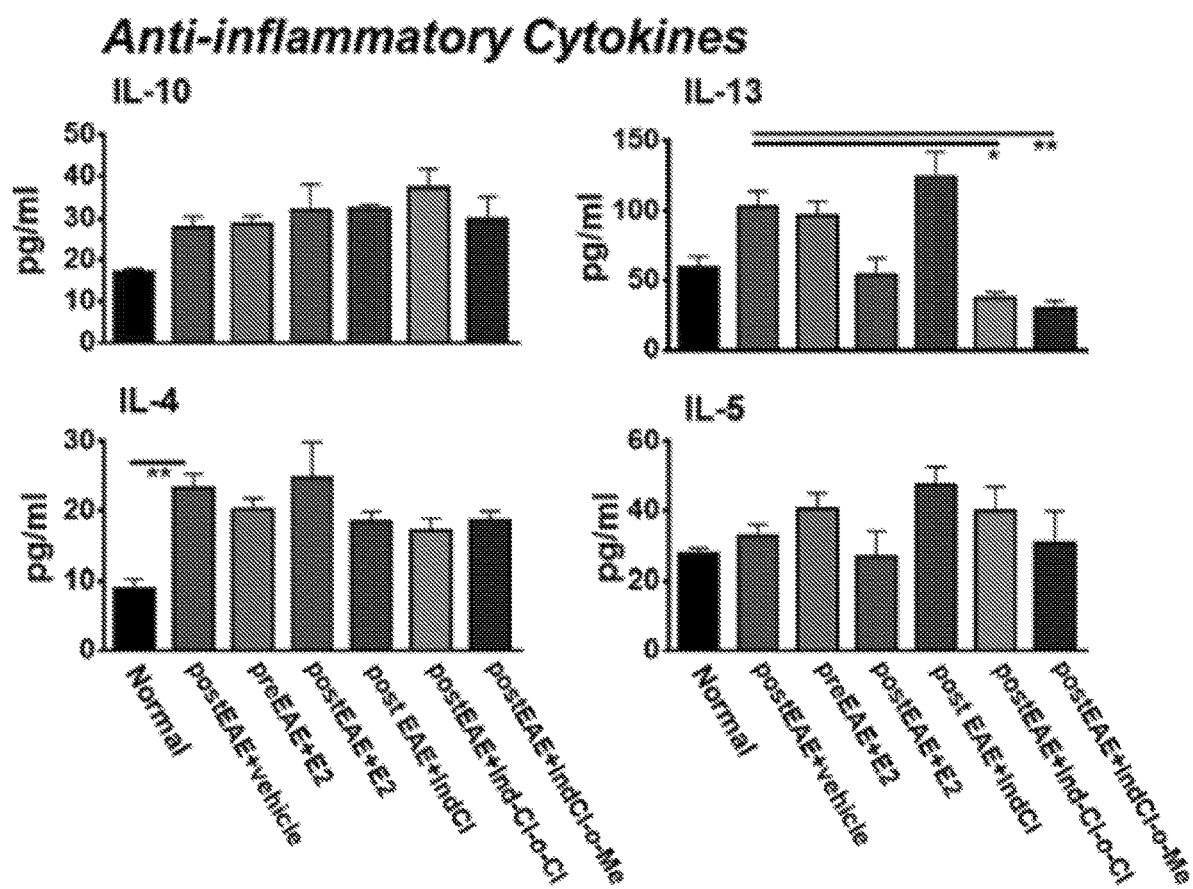
FIG. 4B. Cytokine production by MOG35-55-stimulated splenocytes was assessed from EAE mice sacrificed on post-induction day 21. Anti-inflammatory cytokine production of IL-10, IL-13, IL-4, and IL-5 revealed no significant differences in all treatment groups compared to vehicle. Data are representative of experiments repeated twice. n=4-6 mice/group, Kruskal Wallis Analysis with Dunn's Multiple Comparisons Analysis and Ordinary One-Way ANOVA with Dunnett's Multiple Comparisons Analysis.

Anti-inflammatory Cytokines (FIG. 4B): Skewing the adaptive immune response toward a Th2 profile, which is characterized by production of cytokines such as IL-4, IL-5, and IL-13, ameliorates EAE disability (Moss et al., 2004). Therefore, concentrations of these cytokines, along with the key anti-inflammatory and immunoregulatory cytokine IL-10 (Ouyang et al., 2011), in supernatants were assessed. Splenocytes from vehicle-treated mice exhibited increased IL-4 production compared to normal, but IL-5, IL-10, and IL-13 levels were unchanged. Neither prophylactic nor therapeutic E2 significantly altered Th2 or IL-10 production relative to vehicle. Similarly, IndCl had no effect on cytokine concentrations. In contrast to IndCl, splenocytes from IndCl-o-Cl and IndCl-o-Me-treated mice exhibited attenuated IL-13 production compared to vehicle.

Figure 4C:
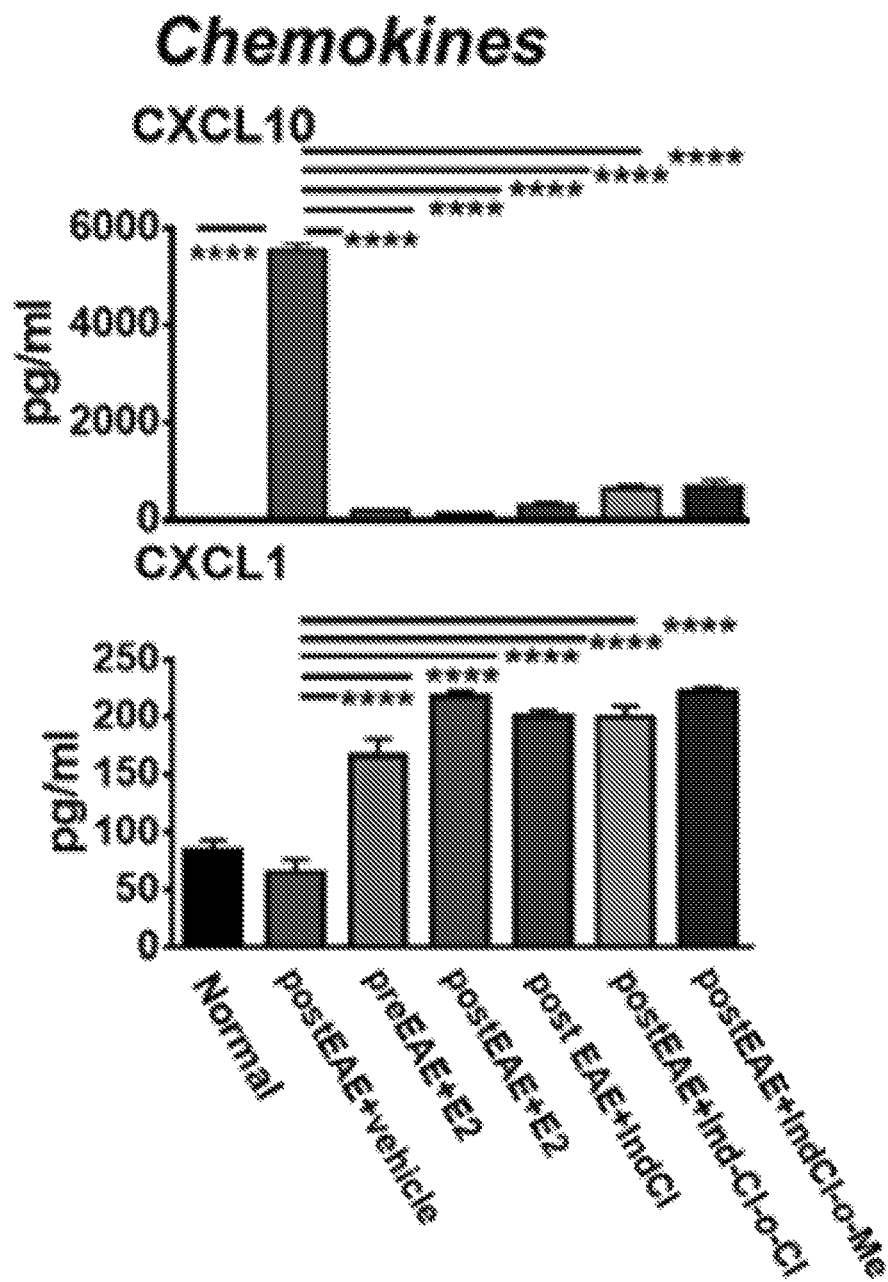
FIG. 4C. Cytokine production by MOG35-55-stimulated splenocytes was assessed from EAE mice killed on post-induction day 21. Therapeutic treatment with E2 and ERβ ligands showed a significant increase in chemokine CXCL1 levels, with no change in prophylactic E2 treatment compared to vehicle. Vehicle-treated mice exhibited significantly elevated levels of CXCL10 compared to normal controls. Prophylactic E2 and therapeutic treatment with E2 and ERβ ligands significantly reduced CXCL10 levels compared to vehicle. Data are representative of experiments repeated twice. n=4-6 mice/group, Kruskal Wallis Analysis with Dunn's Multiple Comparisons Analysis and Ordinary One-Way ANOVA with Dunnett's Multiple Comparisons Analysis.

Chemokines (FIG. 4C): CXCL1 and CXCL10 are leukocyte chemoattractants with critical, but largely divergent, effects on OPC survival. CXCL1 signaling through its receptor, CXCR2, is essential for homeostatic white matter development (Robinson et al., 1998), OPC proliferation (Filipovic and Zecevic, 2008), and survival (Tirotta et al., 2011). In contrast, CXCL10 induces OPC cell death in vitro, which is augmented by the addition of IFNγ (Tirotta et al., 2011). Splenocytes from vehicle-treated mice displayed no change in CXCL1, but significantly upregulated CXCL10 production compared to normal. Splenocytes from prophylactic and therapeutic E2 treated mice produced increased concentrations of CXCL1 and decreased CXCL10 relative to vehicle. Similarly, splenocytes from both IndCl and analogue-treated mice exhibited increased CXCL1 and decreased CXCL10 levels compared to vehicle.

Example 6. IndCl Analogue Treatment does not Affect Leukocyte Infiltration, Macrophage/Microglia Accumulation, or Astrogliosis in Thoracic Spinal Cord White Matter IndCl has been shown to reduce several indicators of inflammation during EAE, including staining intensity of the pan-leukocyte marker cluster of differentiation (CD) 45 and the degree of glial fibrillary acidic protein (GFAP)+ astrogliosis present in dorsal column white matter (Moore et al., 2014). To assess whether IndCl analogues exert similar anti-inflammatory effects, CD45+ leukocyte, ionized calcium-binding adapter molecule 1 (Iba1)+ macrophage/microglia, and GFAP+ astrocytes were assessed in thoracic spinal cord dorsal column sections from normal and EAE mice.

Figure 5A:
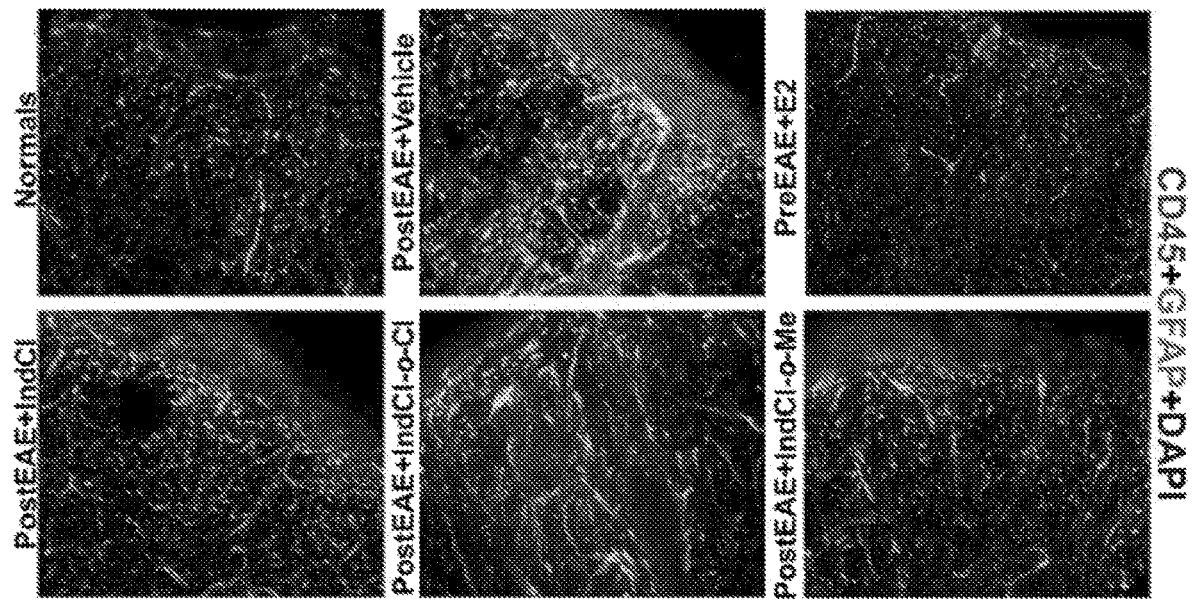
FIG. 5A shows representative 40× magnification confocal images of the spinal cord dorsal column in EAE mice revealing increased intensity of cluster of differentiation (CD) 45 and glial fibrillary acidic protein (GFAP), in vehicle-treated EAE mice compared to normal control mice. Prophylactic E2 treatment decreased GFAP and CD45 intensity. In contrast, IndCl, IndCl-o-Cl and IndCl-o-Me exhibited similar GFAP and CD45 fluorescence intensity as vehicle treated mice.
Figure 5B:
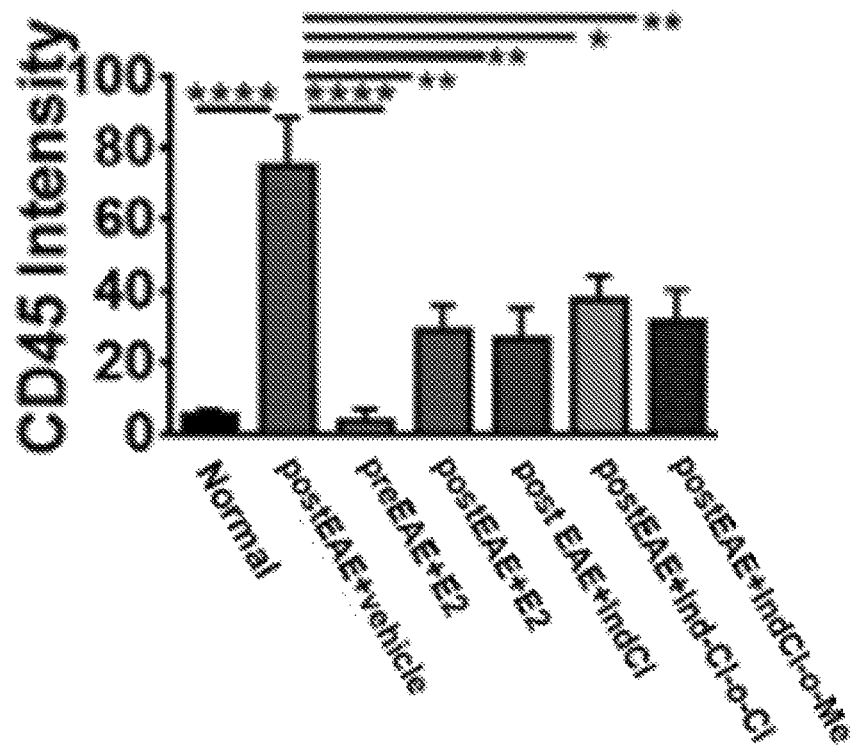
FIG. 5B shows the quantification of the relative fluorescence intensities of CD45 from normal, vehicle, prophylactic E2, therapeutic IndCl, IndCl-o-Cl and IndCl-o-Me treated EAE mice. Vehicle treated mice exhibited increased CD45 fluorescence intensity that was significantly decreased only with prophylactic E2 treatment. ERβ ligand treatment with IndCl, IndCl-o-Cl and IndCl-o-Me exhibited similar degrees of intensity of CD45 as vehicle-treated EAE mice. n=5-8 mice/group, ANOVA.

Leukocytes (FIGS. 5A-5B): In mice given vehicle only, dorsal column white matter displayed extensive CD45+ infiltration into spinal cord parenchyma, with staining intensity significantly elevated relative to normal controls. Prophylactic E2 reduced CD45+ staining intensity compared to vehicle-treated mice.

Figure 5C:
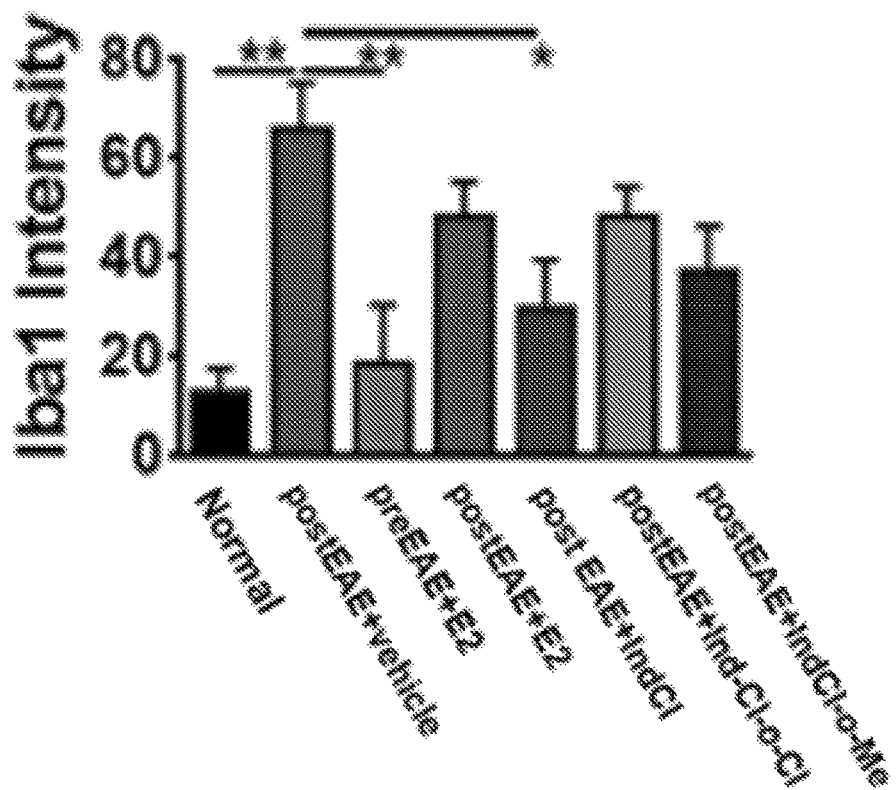
FIG. 5C shows the quantification of the relative fluorescence intensities of Iba1 from normal, vehicle, prophylactic E2, therapeutic IndCl, IndCl-o-Cl and IndCl-o-Me treated EAE mice. Vehicle treated mice exhibited increased Iba1 fluorescence intensity that was significantly decreased only with prophylactic E2 treatment. ERβ ligand treatment with IndCl, IndCl-o-Cl and IndCl-o-Me exhibited similar degrees of intensity of Iba1 as vehicle-treated EAE mice. n=5-8 mice/group, ANOVA.

Macrophages/microglia (FIG. 5C): Vehicle-treated spinal cord sections exhibited increased Iba1+ staining intensity compared to normal. Prophylactic E2 suppressed the increased Iba1+ staining intensity observed in vehicle-treated mice, while therapeutic E2 and the IndCl analogues did not.

Figure 5D:
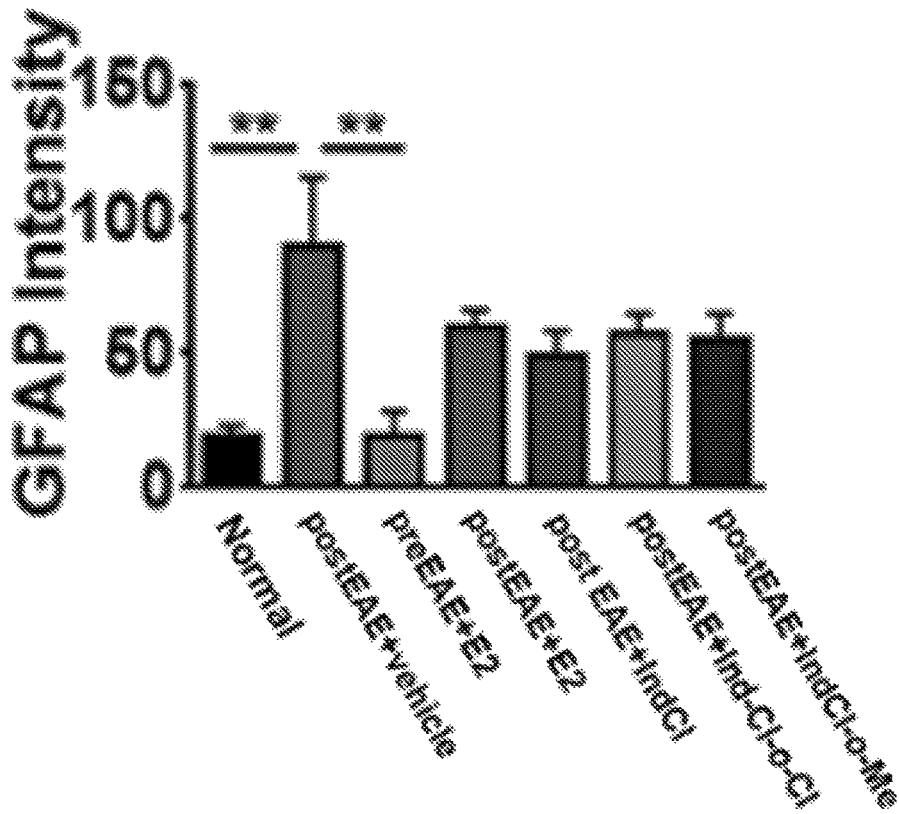
FIG. 5D shows the quantification of the relative fluorescence intensities of GFAP from normal, vehicle, prophylactic E2, therapeutic IndCl, IndCl-o-Cl and IndCl-o-Me treated EAE mice. Vehicle treated mice exhibited increased GFAP fluorescence intensity that was significantly decreased only with prophylactic E2 treatment. ERβ ligand treatment with IndCl, IndCl-o-Cl and IndCl-o-Me exhibited similar degrees of intensity of GFAP as vehicle-treated EAE mice. n=5-8 mice/group, ANOVA.
Figure 5E:
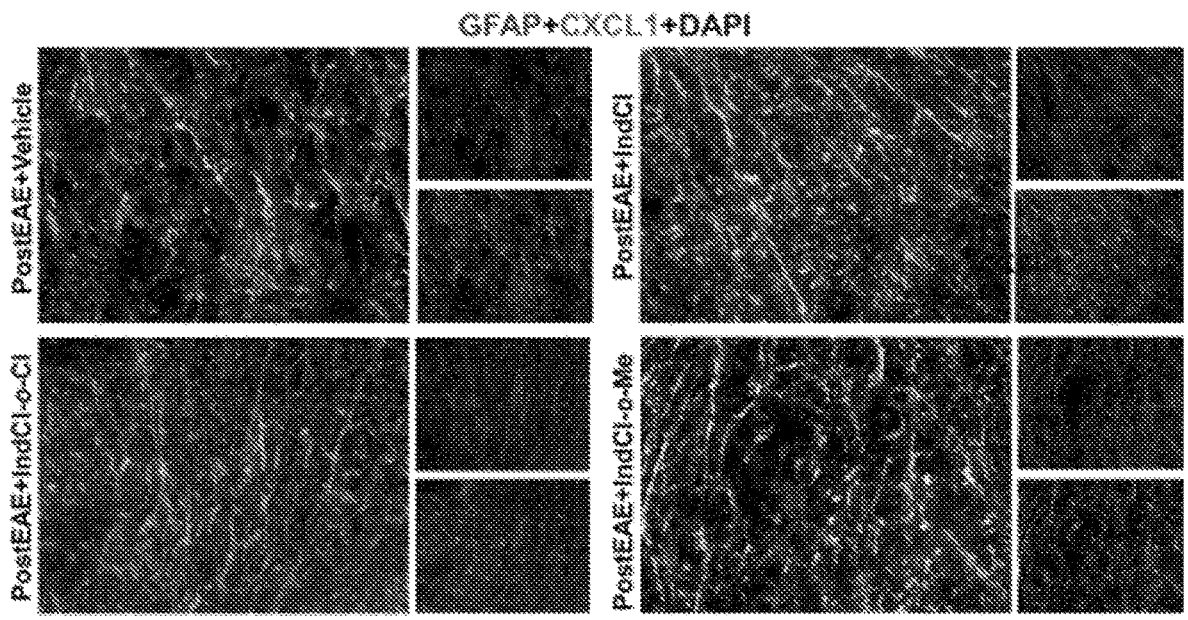
FIG. 5E shows representative 40× magnification coronal images of the ventral column of thoracic spinal cord collected at peak disease (day 21). Sections collected from vehicle, IndCl, IndCl-o-Cl and IndCl-o-Me were immunostained with chemokine (C—X—C motif) ligand 1 (CXCL1), Glial fibrillary acidic protein (GFAP), and nuclear stain (DAPI).
Figure 5F:
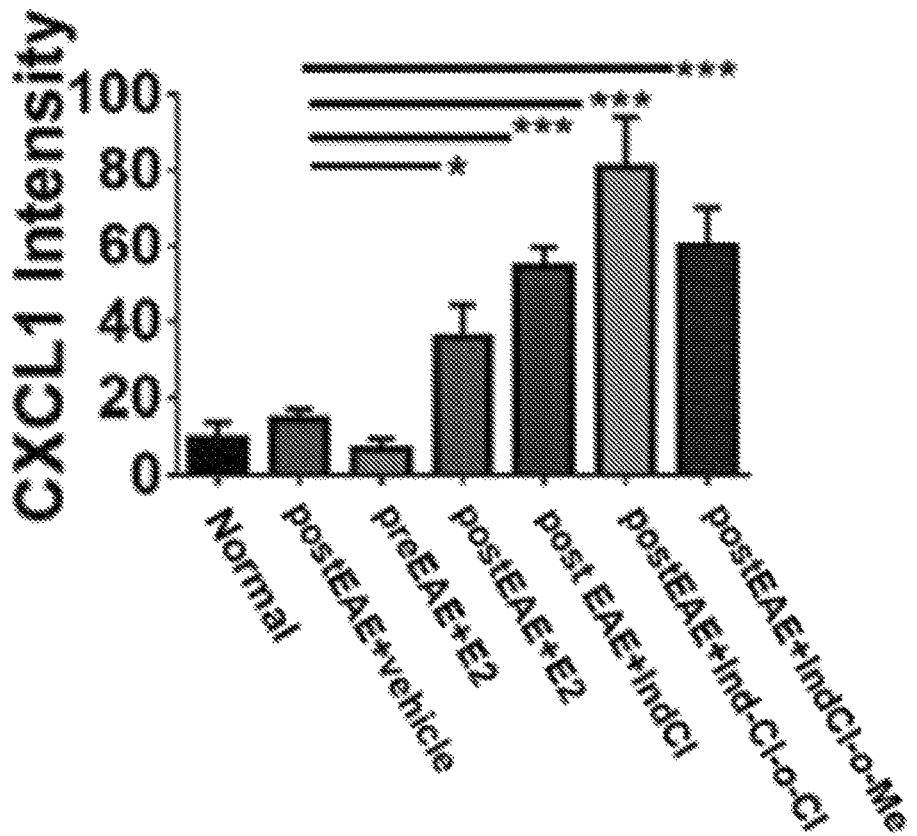
FIG. 5F shows the quantification of the relative fluorescence intensity of CXCL1 from normal, vehicle, IndCl, IndCl-o-Cl and IndCl-o-Me. A significant increase in CXCL1 intensity of IndCl, IndCl-o-Cl and IndCl-o-Me was measured as compared to vehicle-treated EAE mice. n=5-8 mice/group, Ordinary One-Way ANOVA with Dunnett's Multiple Comparisons Analysis.

Astrogliosis (FIGS. 5A and 5D): GFAP+ staining intensity was significantly increased in vehicle-treated dorsal column white matter, indicating widespread astrogliosis. In line with its effects on other measures of inflammation, prophylactic E2 significantly reduced GFAP+ staining intensity. Whereas, therapeutic E2, IndCl, or IndCl analogue treatment did modify GFAP+ staining intensity.

Figure 6A:
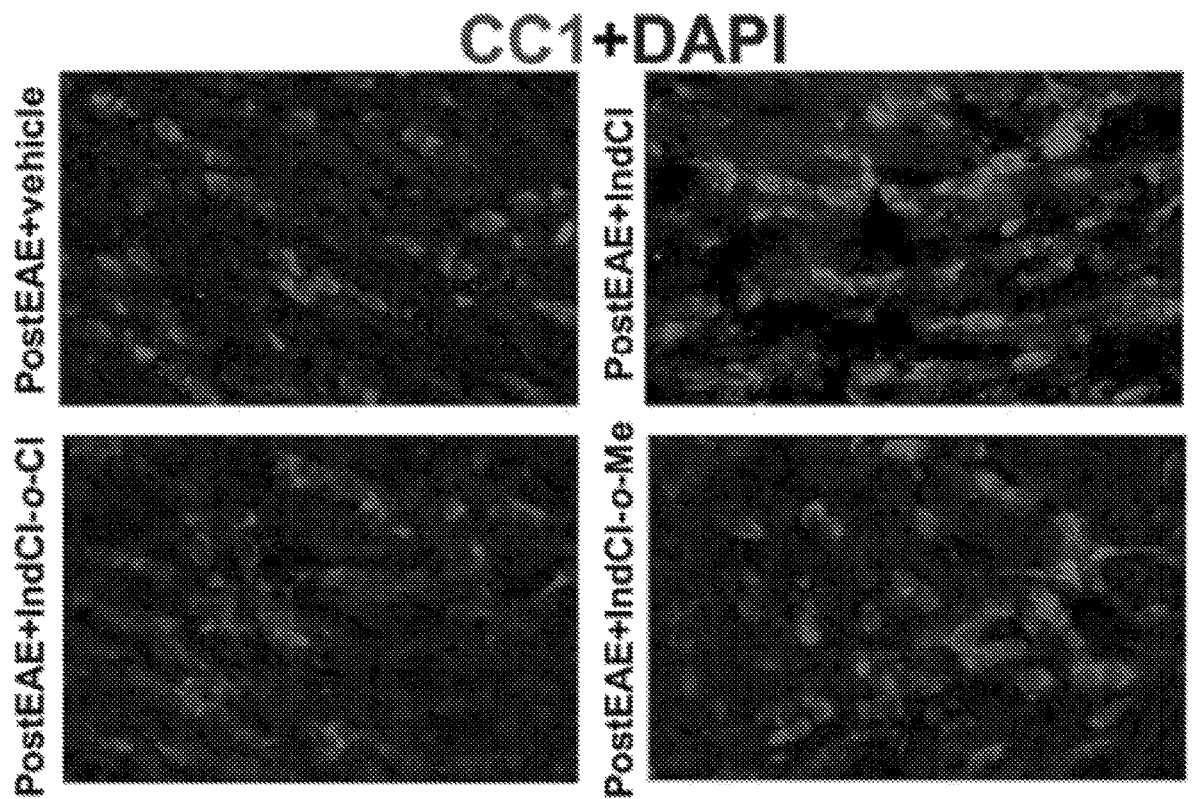
FIG. 6A shows fluorescence images of mature OLs stained for adenomatous polyposis coli (CC1) and myelin basic protein (myelin).
Figure 6B:
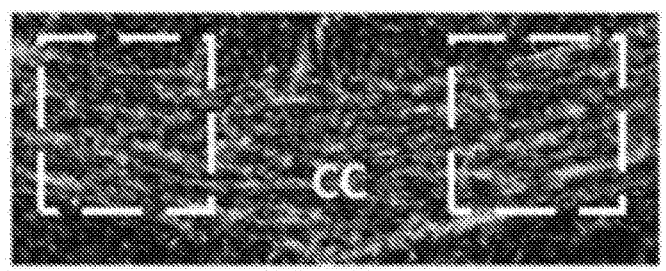
FIG. 6B shows images within the normal corpus callosum where the white-dashed boxes depict the areas examined at 40× magnification in FIG. 6A.
Figure 6C:
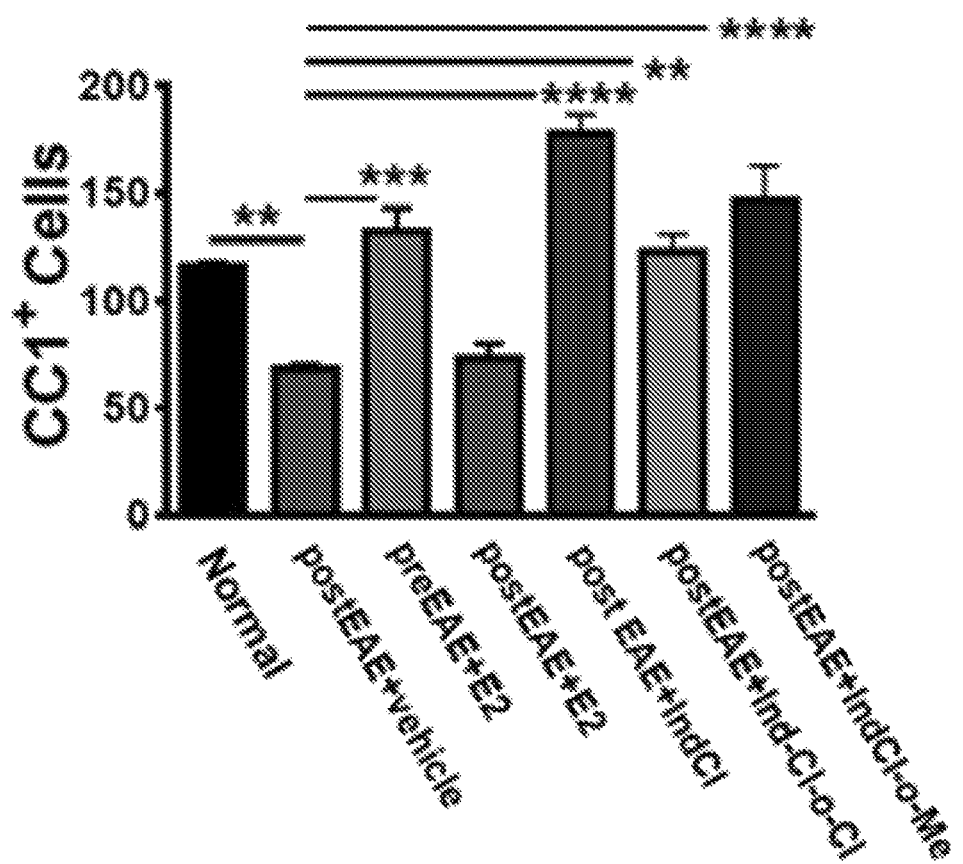
FIG. 6C shows a bar graph quantifying a significant increase in numbers of mature OLs in therapeutic IndCl, IndCl-o-Cl and IndCl-o-Me treated EAE mice.
Figure 6D:
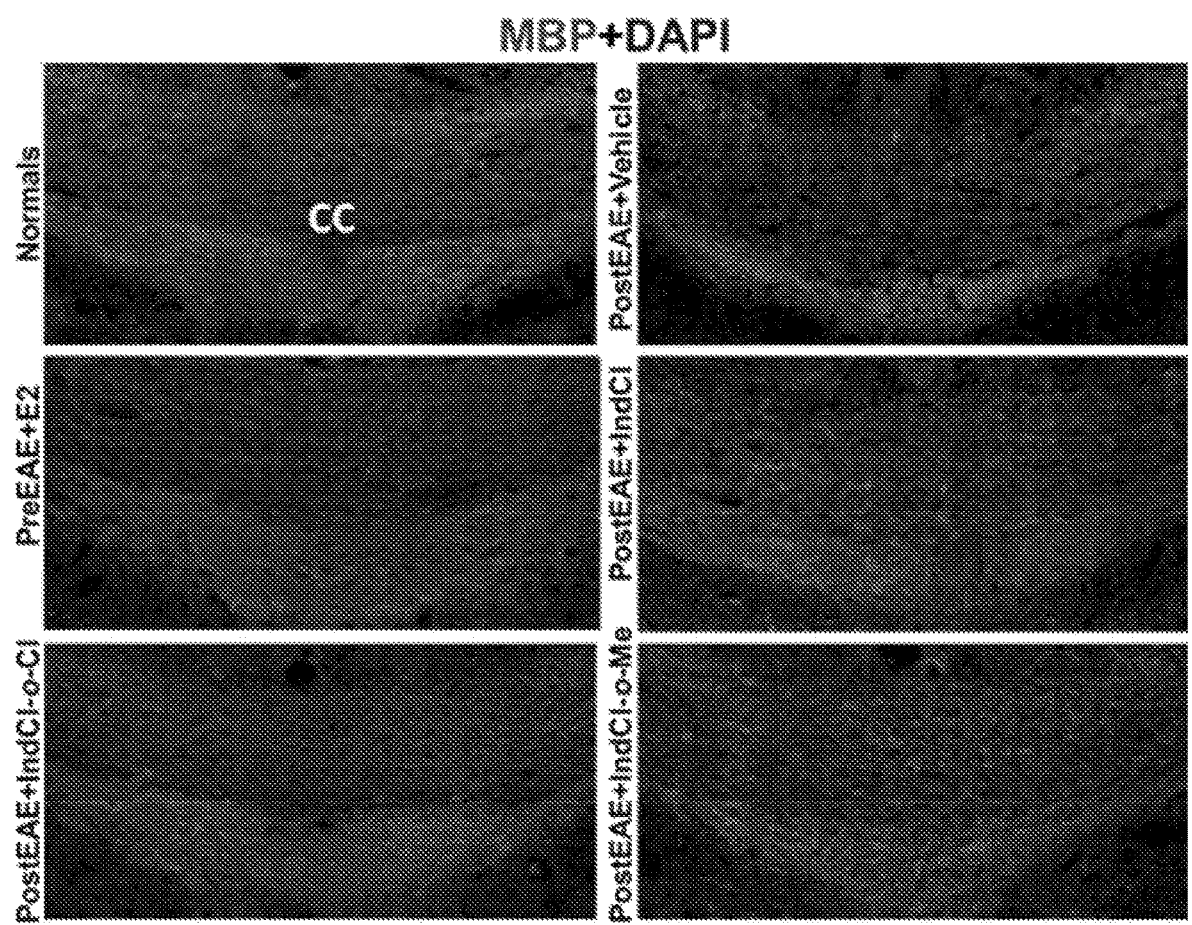
FIG. 6D shows representative 10× magnification images of midline-crossing corpus callosum from coronal brain sections stained for MBP to assess myelination levels.
Figure 6E:
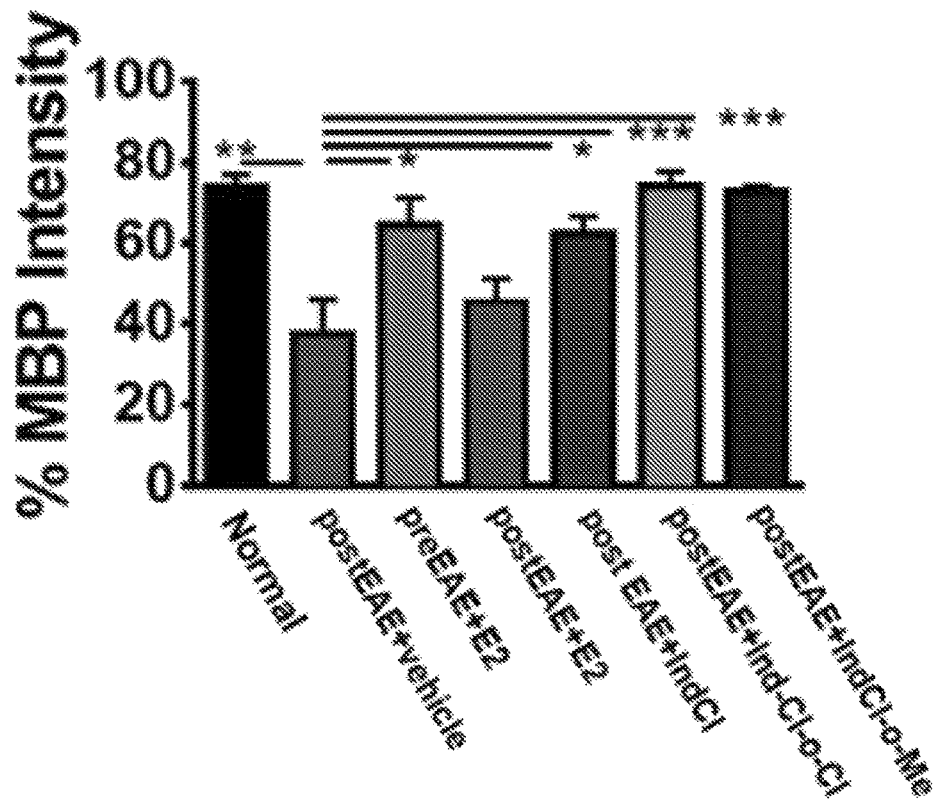
FIG. 6E shows a bar graph quantifying MBP+ intensity for all treatments. n=8 mice/group, ANOVA.

Example 7. Therapeutic IndCl Analogues Enhance Astrocytic CXCL1 Expression During EAE Under inflammatory conditions, such as those generated by MS, astrocytes undergo NF-κB-dependent upregulation of CXCL1, which is thought to recruit OPCs to the site of demyelinating injury (Omari et al., 2006; Xue et al., 2014). Thus, having observed that IndCl raised its production by peripheral leukocytes, CXCL1 expression in thoracic ventral column white matter was next evaluated. Vehicle-treated mice exhibited CXCL1+ staining intensity comparable to normal (FIGS. 6A-6B). In contrast with its effect on CXCL1 production by peripheral leukocytes, prophylactic E2 treatment caused no change in CXCL1+ staining intensity relative to vehicle (FIGS. 6A-6B). However, there was a small but significant increase in CXCL1 intensity with therapeutic E2 treatment. IndCl, IndCl-o-Cl, and IndCl-o-Me treatment significantly increased ventral column CXCL1 staining intensity compared to vehicle, with staining intensity appearing to co-localize more extensively with GFAP+ astrocytes (FIGS. 6A-6B).

Example 8. IndCl Analogues Increase Mature OL Numbers and Restore Myelination in Callosal White Matter Tracts in EAE Mice IndCl and other ERβ ligands have been shown to increase white matter and subventricular zone OPC/OL populations and enhance callosal myelination in translational models of MS (Tiwari-Woodruff et al., 2007; Crawford et al., 2010; Moore et al., 2014). To test whether IndCl analogues promote similar gains in mature OL numbers and myelination, callosal white matter tracts were assessed for adenomatous polyposis *coli* (CC1) and MBP immunoreactivity, respectively. Additionally, ultrastructural analysis of the CC was performed by EM imaging to confirm the integrity of axon myelination.

Figure 7A:
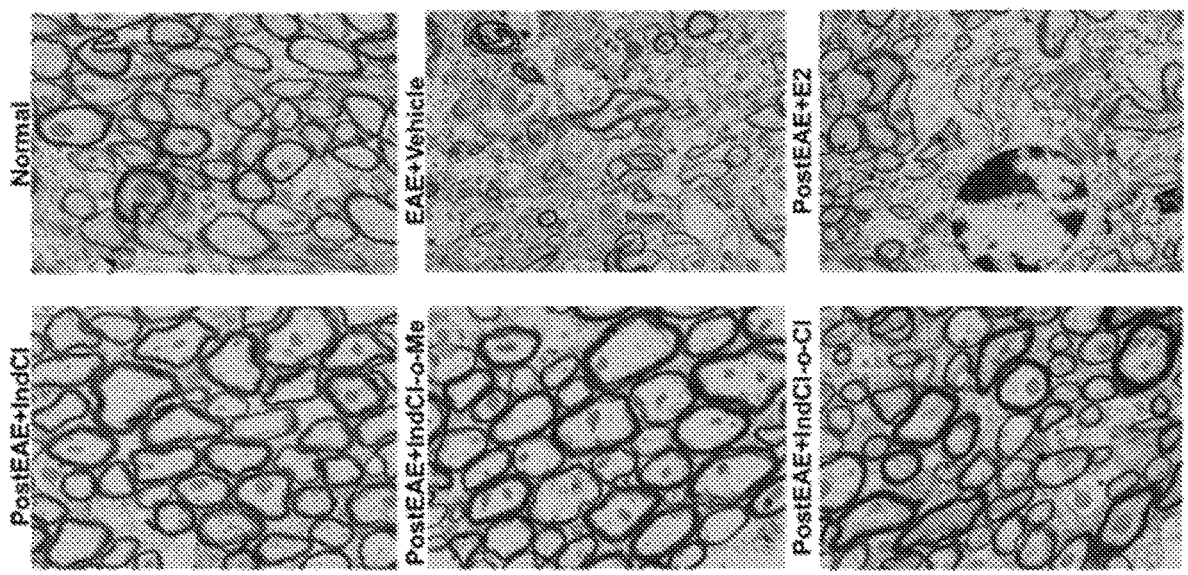
FIG. 7A shows representative electron micrographs of IndCl analogues-treated EAE corpus callosum axons imaged at 14,000× magnification.
Figure 7B:
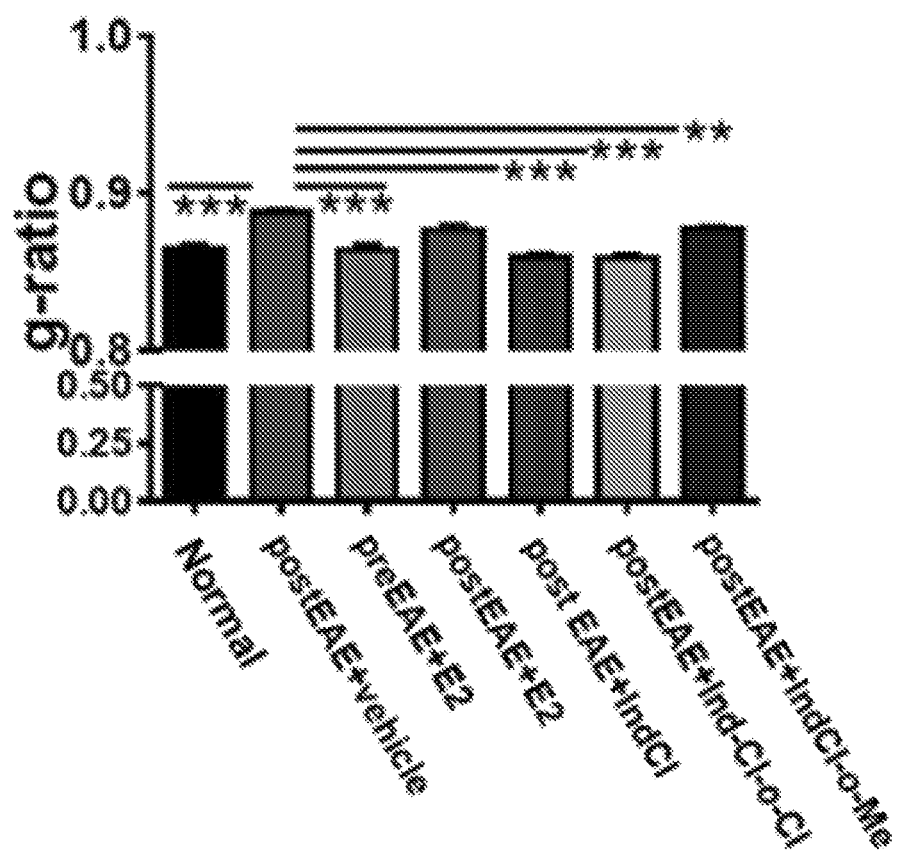
FIG. 7B shows a bar graph quantifying G-ratios in all treatment groups. It reveals lower g-ratios in all IndCl analogue treated groups and increased axon myelination. The IndCl analogue-treated EAE groups had mean g-ratio lower than the postEAE+IndCl (positive control) groups. A minimum of 500 axons were measured per mouse. (Scale bar=1.0 μm.) n=4-8 mice/group Ordinary One-Way ANOVA with Dunnett's Multiple Comparisons Analysis.

Mature OLs (FIGS. 7A and 7C): Vehicle-treated mice exhibited significant loss of CC1+ mature OLs relative to normal mice. Prophylactic E2 treatment did not show a decrease in CC1 cells, however, E2 treatment after disease induction was unable to rescue the decrease in CC1 cells. Whereas, therapeutic treatment with IndCl and IndCl analogues rescued the loss of CC1+ cells observed in vehicle mice MBP+ myelination (FIGS. 7D and 7E): Corresponding with loss of CC1+ mature OLs, MBP+ staining was decreased in vehicle-treated mice relative to control. Prophylactic E2 presence prevented the EAE-induced decrease in MBP+ staining, while therapeutic E2 was unable to rescue the decrease in MBP staining intensity as seen in vehicle-treated EAE corpus callosum. Also, consistent with CC1 data, IndCl, IndCl-o-Cl, and IndCl-o-Me treatment all resulted in increased MBP+ staining with respect to vehicle.

Figure 8A:
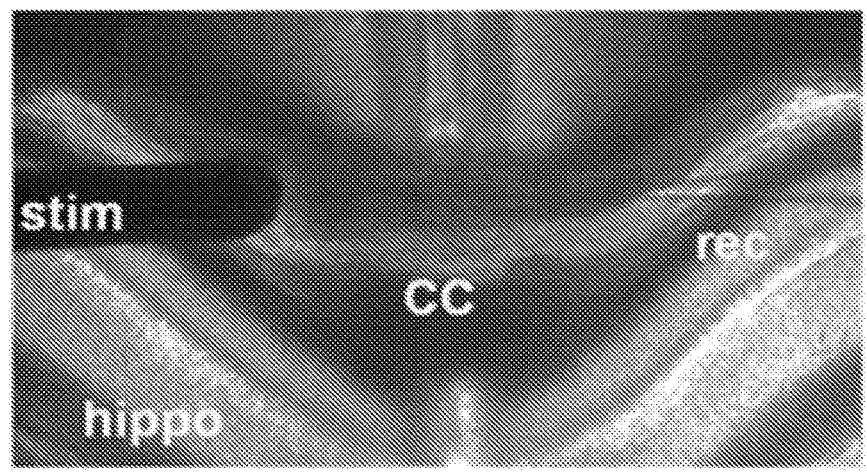
FIG. 8A shows a bright field image of the method used for recording compound action potentials (CAPs) across the corpus callosum (CC) in caudal brain slices (350-μm thick) plate 48-55 (Paxinos atlas) containing the hippocampus (hipp). A recording electrode (rec) was placed 1 mm away from a bipolar stimulating electrode (stim), and voltage traces were recorded with increasing current stimulus of 0-4 mA in steps of 0.5 mA.

EM analysis (FIGS. 8A and 8B): Within a given field imaged, g-ratios were calculated by comparing mean ratio of inner axonal diameter to total outer diameter for all myelinated and non-myelinated fibers. Roughly 50% of callosal fibers were non-myelinated or thinly myelinated in vehicle-treated mice compared to 10% in normal, resulting in a g-ratio that was significantly increased in vehicle-treated mice (Crawford et al., 2010; Mangiardi et al., 2011). Prophylactic E2 reduced g-ratio relative to vehicle treatment; however, therapeutic E2 was ineffective at raising this parameter. Treatment with IndCl or either analogue decreased both non-myelinated axons numbers and g-ratio relative to vehicle.

Figure 8B:
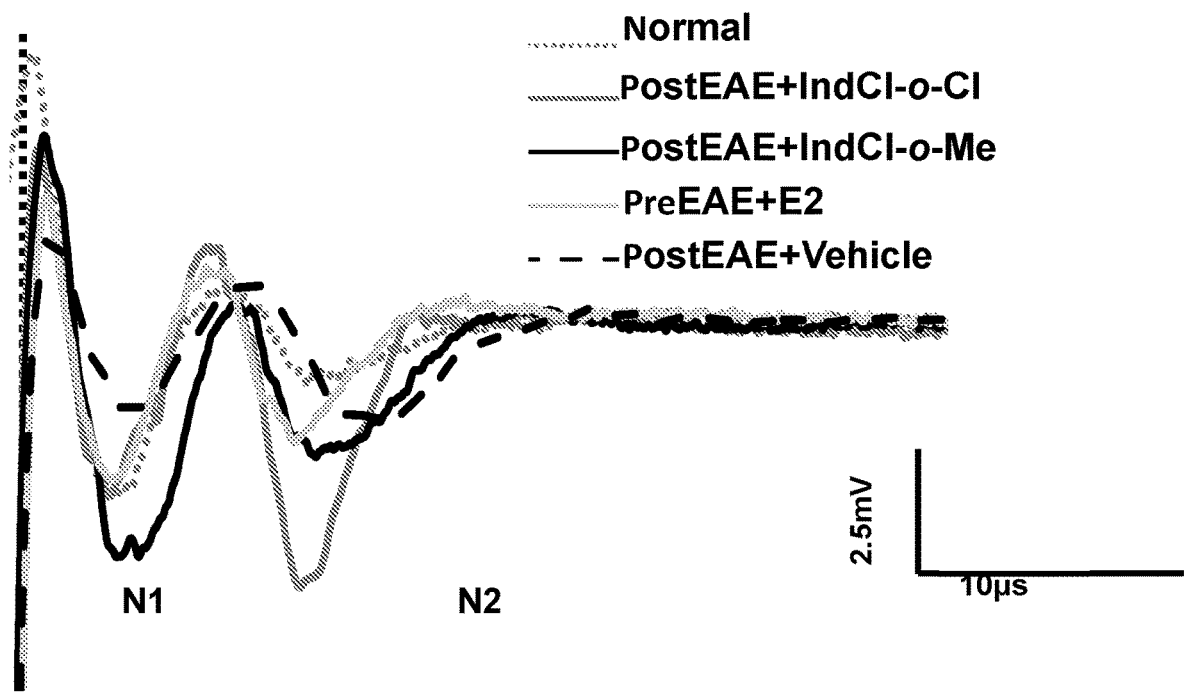
FIG. 8B shows voltage traces acquired with 4 mA stimulation intensity from normal, 30 days postEAE+vehicle, preEAE+E2, postEAE+IndCl-o-Cl, postEAE+IndCl-o-Me, and postEAE+IndCl brain slices. Dashed line indicates the end of the stimulus artifact and the beginning of the CAPs. The faster myelinated axon peak is indicated by "N1", and the CAP component "N2" denotes the slower partially myelinated or unmyelinated axons peak.
Figure 8C:
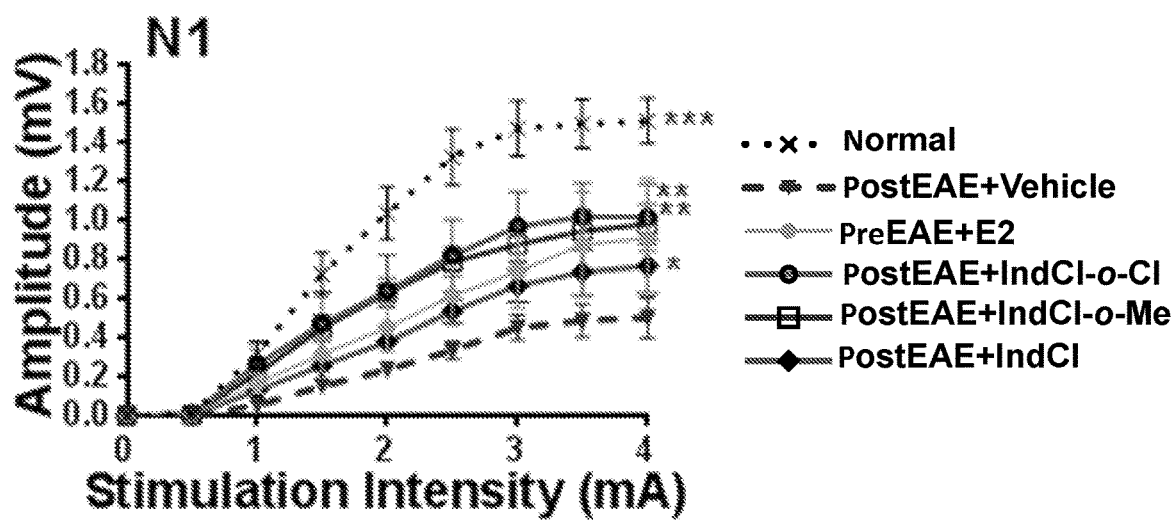
FIG. 8C shows N1 CAP amplitudes of callosal axons recorded from vehicle-treated EAE slices (red) were significantly smaller than in normal controls. Similar to IndCl, IndCl-o-Cl and IndCl-o-Me treatment resulted in improved N1. N2 amplitudes of Ind-o-Cl had a small but significant increase as compared to EAE+vehicle group. Statistical analysis for C and D consisted of Two-Way ANOVA with post hoc tests using Tukey's multiple comparison test. n=6-12 animals per group, Two-Way ANOVA with post hoc tests using Tukey's multiple comparison test.
Figure 8D:
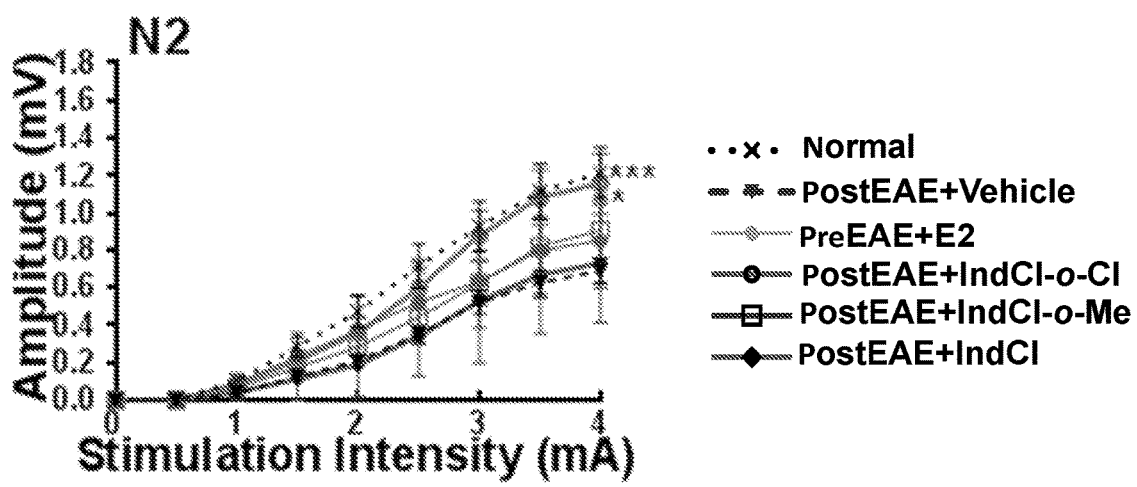
FIG. 8D shows N2 CAP amplitudes of callosal axons recorded from vehicle-treated EAE slices were significantly smaller than in normal controls. Similar to IndCl, IndCl-o-Cl and IndCl-o-Me treatment resulted in improved N1. N2 amplitudes of Ind-o-Cl had a small but significant increase as compared to EAE+vehicle group. Statistical analysis for C and D consisted of Two-Way ANOVA with post hoc tests using Tukey's multiple comparison test. n=6-12 animals per group, Two-Way ANOVA with post hoc tests using Tukey's multiple comparison test.
Figure 10A:
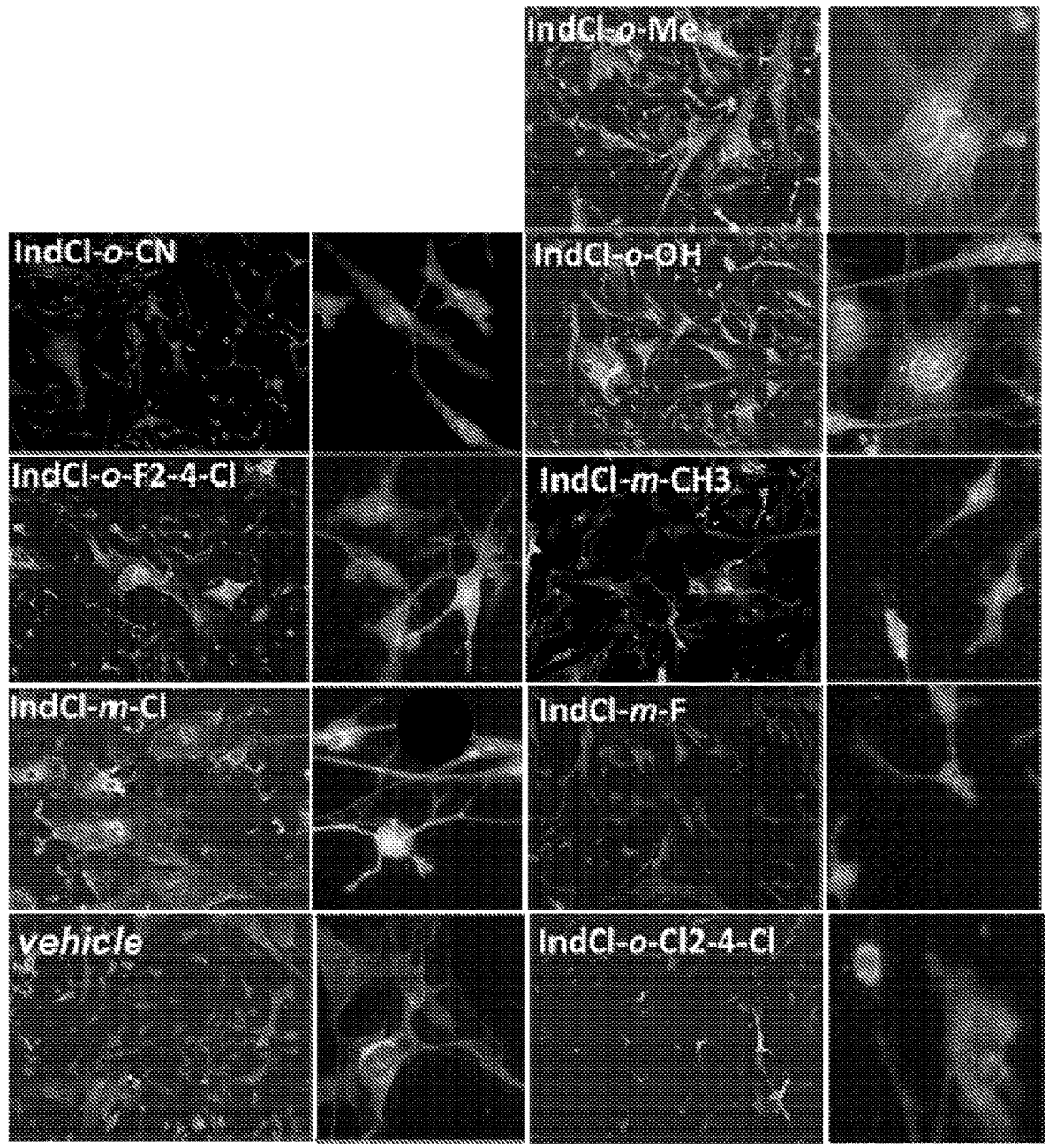
FIG. 10A shows representative images of primary oligodendrocyte and oligodendrocyte precursor cells (OL/OPCs) from wells containing differentiating media alone (normal media), vehicle or 8 different IndCl analogues. OLs were immunostained with myelin basic protein (MBP, green) and co-stained with nuclear stain DAPI (blue). There were 3 wells/treatment group.
Figure 11B:
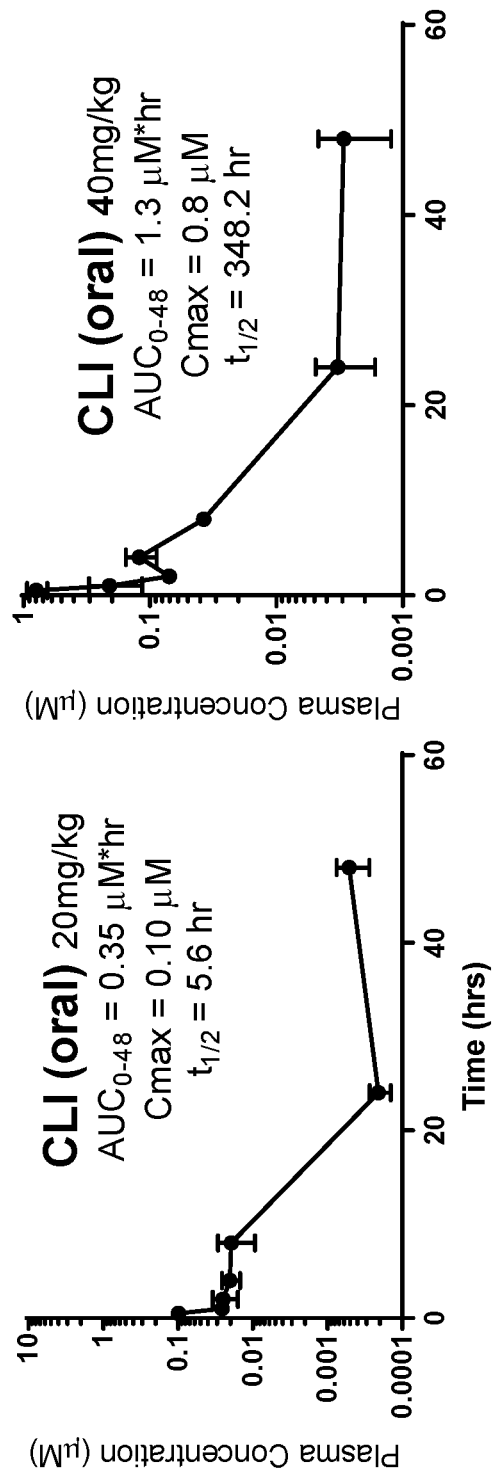
FIG. 11B shows the pharmacokinetics and half-lives of CLI in mice after oral administration at 20 mg/kg (200 μL PEG400/Tween80/Povidone/0.5% Carboxymethyl Cellulose in water=9/0.5/0.5/90 ratio) and 40 mg/kg (200 μL 2-hydroxypropyl-β-CD 40% aqueous solution MW ~1540).
Figure 11D:
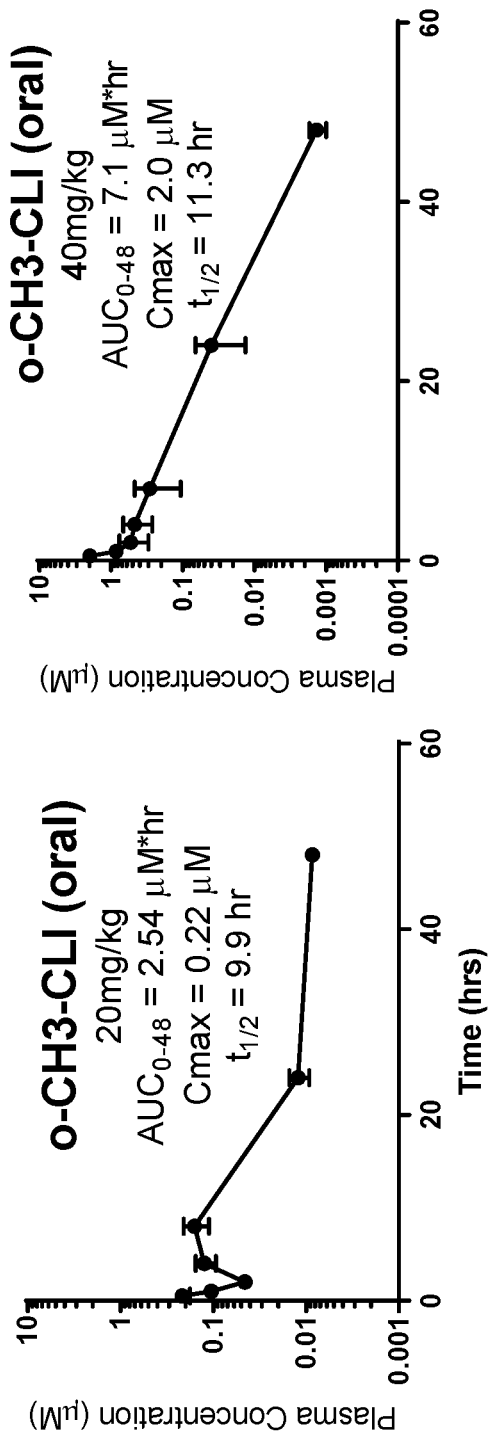
FIG. 11D shows the pharmacokinetics and half-lives of o-CH3-CLI in mice after oral administration at 20 mg/kg (200 μL PEG400/Tween80/Povidone/0.5% Carboxymethyl Cellulose in water=9/0.5/0.5/90 ratio per mouse) and 40 mg/kg (200 μL 2-hydroxypropyl-β-CD 40% aqueous solution MW ~1540 per mouse).

Example 9. IndCl Analogues Improve Fast and Slow Components of Commissural Axon Conduction During EAE Large white matter tracts, such as the CC, are especially vulnerable to demyelination and axonal damage in MS and EAE (Ozturk et al., 2010; Mangiardi et al., 2011). Compound action potential (CAP) recordings are a valuable technique for assessing demyelination and damage in these areas through their impact on functional conductivity (Crawford et al., 2009; Crawford et al., 2010; Moore et al., 2013). Thus, callosal CAPs were recorded in brain slices obtained from normal, IndCl, pre-E2, IndCl-o-Cl and IndCl-o-Me-treated mice (FIGS. 8A-D). N1 and N2 peak amplitudes (representing fast myelinated and slower un/partially myelinated fibers, respectively) were reduced in slices from vehicle-treated mice compared to normal, and were not affected by prophylactic or therapeutic E2 treatment (FIGS. 8B-D). Slices from IndCl and analogue-treated mice showed significant improvement in N1 amplitude, but only IndCl-o-Cl treatment also increased N2 amplitude (FIGS. 8B-D).

The studies in Examples 1-9 found that the IndCl analogues tested shared many therapeutic qualities in common with their parent compound, but also displayed several unique benefitsnotobservedwithIndCltreatmentthatspeak-totheirpromiseforultimateclinical utility. Examination of the functional, histopathological, and immunological basis of the pro-myelinating effects of IndCl-based ERβ ligands has shown that some of the IndCl analogues tested possess therapeutic benefits exceeding their parent compound. A summary of the results for a subset of the IndCl analogues can be found in Table 1.

TABLE 1

Summary of in vivo E2, IndCl, and IndCl analogue treatment effects compared to vehicle.

| Category | Marker | Pre E2 | Post E2 | IndCl | IndCl-o-Cl | IndCl-o-Me |
|---|---|---|---|---|---|---|
| Disability | Disease score§ | − | ○ | ○ | − | − |
| | Rotarod performance§ | + | ○ | ○ | + | + |
| Myelination | OLs | + | + | + | + | + |
| | MBP | + | ○ | + | + | + |
| | g-ratio | − | ○ | − | − | − |
| Peripheral Inflammatory Cytokines | IFNγ | − | − | − | − | − |
| | IL-1β§ | ○ | ○ | + | ○ | ○ |
| | IL-2 | − | ○ | ○ | ○ | ○ |
| | IL-6§ | − | − | ○ | − | − |
| | IL-17§ | − | − | ○ | − | − |
| | TNFα | ○ | ○ | ○ | ○ | ○ |
| Peripheral Th2 & Anti-inflammatory Cytokines | IL-4 | ○ | ○ | ○ | ○ | ○ |
| | IL-5 | ○ | ○ | ○ | ○ | ○ |
| | IL-10 | ○ | ○ | ○ | ○ | ○ |
| | IL-13§ | ○ | ○ | ○ | − | − |
| Peripheral Chemokines | CXCL1 | + | + | + | + | + |
| | CXCL10 | − | − | − | − | − |
| CNS Chemokines | CXCL1 | ○ | + | + | + | + |
| CNS Cellular Inflammation | CD45 | − | − | − | − | − |
| | Iba1 | − | ○ | − | ○ | ○ |
| | GFAP | − | ○ | ○ | ○ | ○ |
| Electrophysiology | N1 amplitude | ○ | ○ | + | + | + |
| | N2 amplitude§# | ○ | ○ | ○ | + | ○ |

Table elements containing '+' indicate marker was significantly (p ≤ 0.05) increased in treatment group relative to vehicle. '−' indicates marker was significantly (p ≤ 0.05) decreased in treatment group relative to vehicle, 'o' indicate marker did not change relative to vehicle; § adjacent to a marker indicates differential performance between IndCl and one or more IndCl analogue. # indicates differential performance between analogues.

Example 10. Pharmacokinetics and Half-Lives of CLI, o-CH3-CLI, and o-Cl-CLI

The pharmacokinetics and half-lives of CLI, o-CH3-CLI, and o-Cl-CLI were examined in mice after single subcutaneous injection or oral gavage administration. Two doses (20 or 40 mg/kg) were used with the vehicles (10% ethanol and 90% Miglyol 812N or 10% DMSO and 90% corn oil for s.c. injection and PEG400/Tween80/Povidone/0.5% Carboxymethyl Cellulose in water (9.0:0.5:0.5:90; compounds in solution) or 2-hydroxypropyl-beta-cyclodextrin 40% aqueous solution MW ~1540 for oral administration) as indicated in FIGS. 11A-E.

Figure 12A:
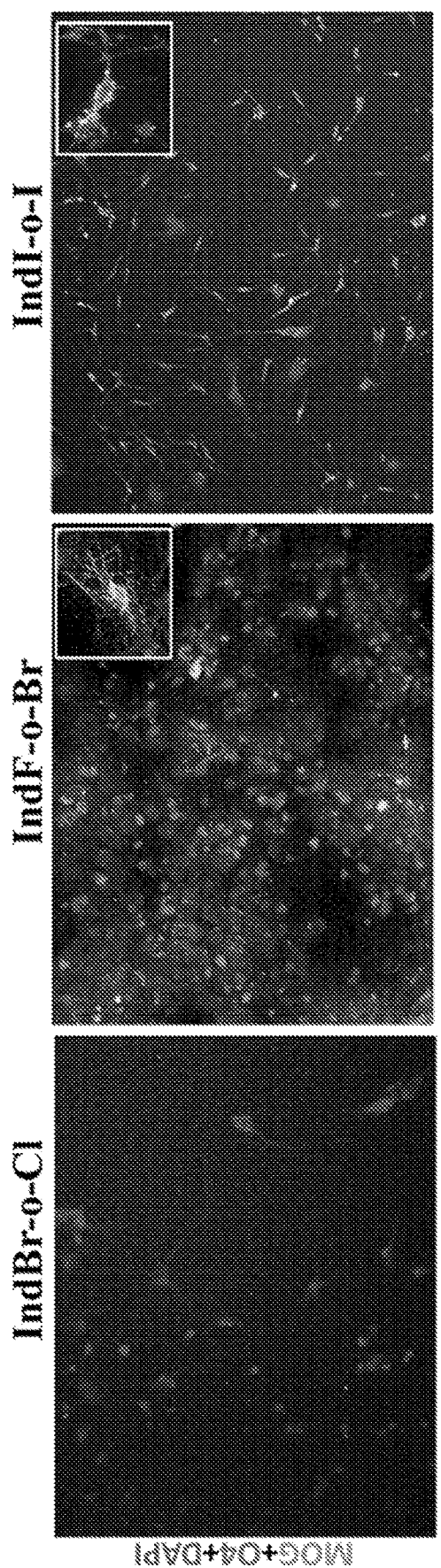
FIG. 12A is representative images of primary OPCs/OLs from wells containing differentiating media in the presence of different analogues. OLs were immunostained with an antigen on the surface of oligodendrocyte progenitors, O4, a marker of mature oligodendrocytes, myelin oligodendrocyte glycoprotein, MOG and co-stained with nuclear stain DAPI.
Figure 12B:
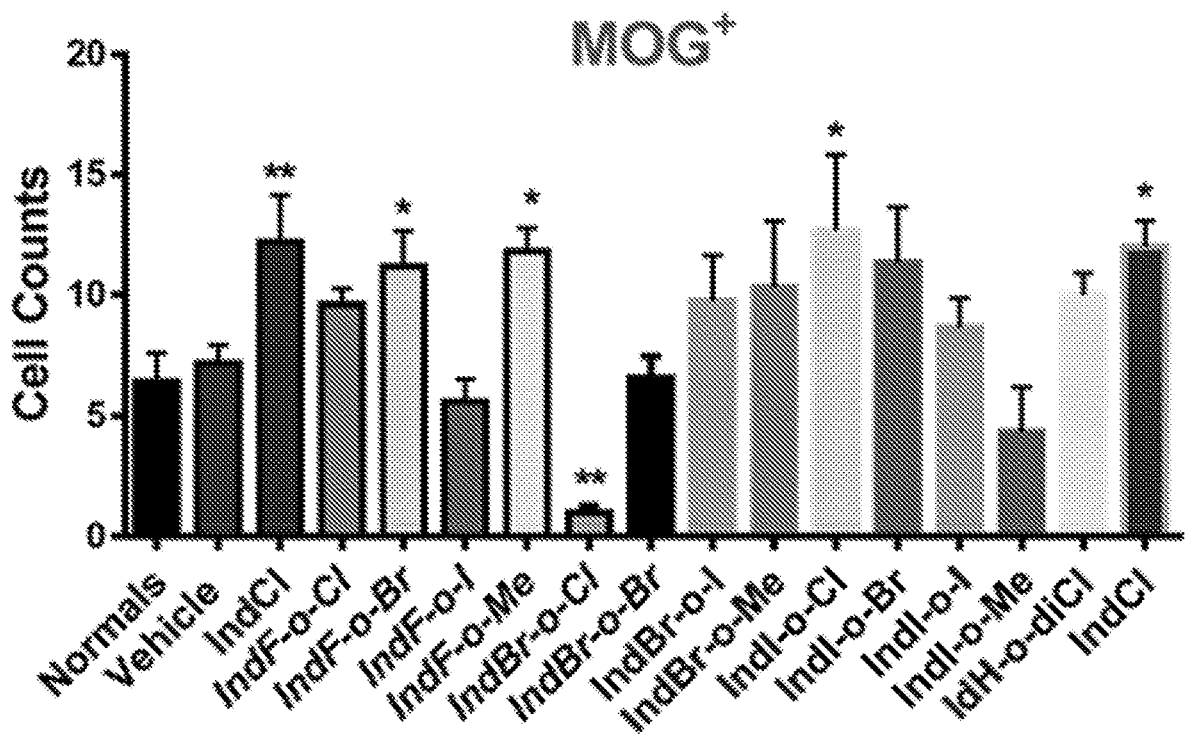
FIG. 12B and FIG. 12C show quantification of the effects of treatment on the number of MOG+ OLs and the number of total cells (DAPI), respectively. Compounds IndCl, IndF-o-Br, IndF-o-Me, and IndBr-o-Me, showed a significant increase in the number of MOG+ OLs compared to vehicle-treated cells (FIG. 12B). A significant increase in total number of cells was observed with IndF-o-Br (FIG. 12C). There were 3 wells/treatment group. n=3 independent experiments were performed. One-Way ANOVA with Dunnett's multiple comparisons test.
Figure 12C:
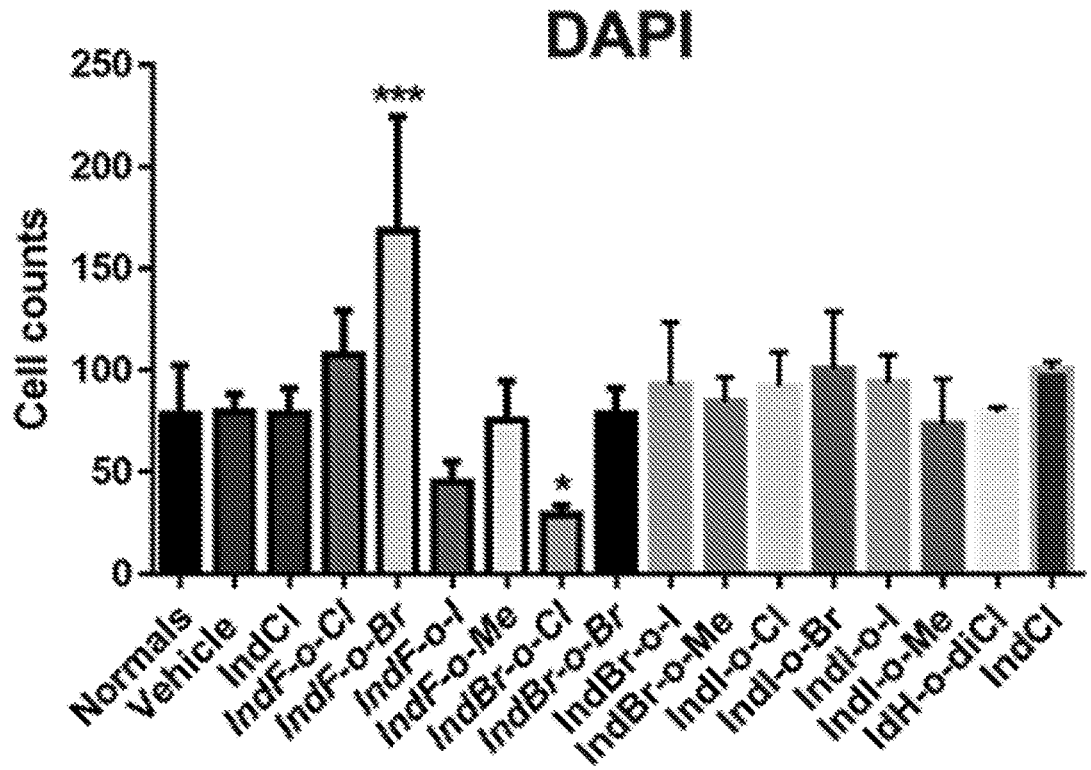

Example 11. Estrogen Receptor β (ERβ) Ligand IndCl and Analogs Effect on Cell Differentiation and Survival The effect on cell differentiation and survival of estrogen receptor § (ERP) ligand IndCl and analogs were investigated. Some estrogen receptor § (ERP) ligands increase primary mouse oligodendrocyte differentiation (FIGS. 12A-12C).

Example 12. IndCl Analogues and a Summary of the Binding Data to Estrogen Receptor Alpha and Beta

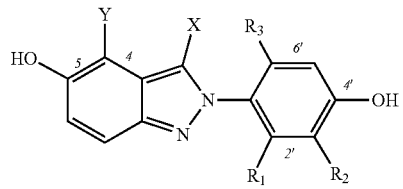

For reasons of completeness, various aspects of the invention are set out in the following numbered clauses:

Clause 1. A compound of formula (I), or a pharmaceutically acceptable salt thereof,

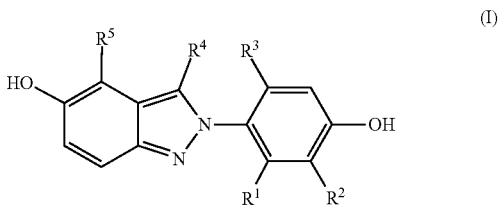

(I)

TABLE 2

| No. | Name | $R_1$ | $R_2$ | $R_3$ | X | Y | RBA$^a$ ER$_\alpha$ | RBA$^a$ ER$_\beta$ | $\beta/\alpha$ Ratio | %MBP$^+$/DAPI$^b$ |
|---|---|---|---|---|---|---|---|---|---|---|
| 1 | IndCl | H | H | H | Cl | H | 0.03 | 32.1 | 107 | ***** |
| 2 | IndCl-o-Br | Br | H | H | Cl | H | 0.47 | 8.31 | 17.9 | * |
| 3 | IndCl-o-Cl | Cl | H | H | Cl | H | 0.40 | 10.9 | 27.1 | ***** |
| 4 | IndCl-o-Me | Me | H | H | Cl | H | 0.43 | 21.1 | 48.9 | ***** |
| 5 | IndCl-o-I | I | H | H | Cl | H | 0.34 | 5.38 | 15.7 | **** |
| 6 | IndCl-o-F | F | H | H | Cl | H | 0.19 | 9.79 | 52.4 | **** |
| 7 | IndCl-o-CN | CN | H | H | Cl | H | 0.05 | 0.77 | 15.7 | --- |
| 8 | IndCl-o-Cl-4-Cl | Cl | H | H | Cl | Cl | 0.33 | 0.73 | 0.46 | * |
| 9 | IndCl-o-F2-4-Cl | F | H | F | Cl | Cl | 0.076 | 0.28 | 3.6 | *** |
| 10 | IndCl-o-Cl$_2$-4-Cl | Cl | H | Cl | Cl | Cl | 0.11 | 2.3 | 21.1 | *** |
| 11 | IndCl-o-CF$_3$ | CF$_3$ | H | H | Cl | H | 2.84 | 10.39 | 3.7 | - |
| 12 | IndCl-o-OH | OH | H | H | Cl | H | 0.062 | 2.99 | 48.2 | **** |
| 13 | IndCl-m-F | H | F | H | Cl | H | 0.14 | 10.5 | 75.7 | ** |
| 14 | IndCl-m-Me | H | Me | H | Cl | H | 0.13 | 0.74 | 5.8 | - |
| 15 | IndF-o-Br | Br | H | H | F | H | 0.37 | 1.22 | 3.3 | *** |
| 16 | IndF-o-Cl | Cl | H | H | F | H | 0.27 | 1.09 | 4.0 | **** |
| 17 | IndF-o-Me | Me | H | H | F | H | 0.11 | 0.37 | 3.4 | ***** |
| 18 | IndF-o-I | I | H | H | F | H | 0.27 | 0.61 | 2.3 | - |
| 19 | IndBr-o-Br | Br | H | H | Br | H | 1.40 | 5.84 | 4.2 | * |
| 20 | IndBr-o-Cl | Cl | H | H | Br | H | 0.81 | 16.12 | 19.9 | ---- |
| 21 | IndBr-o-Me | Me | H | H | Br | H | 1.22 | 11.99 | 9.8 | ***** |
| 22 | IndBr-o-I | I | H | H | Br | H | 0.49 | 6.28 | 12.8 | ***** |
| 23 | IndI-o-Br | Br | H | H | I | H | 1.25 | 6.64 | 5.3 | ***** |
| 24 | IndI-o-Cl | Cl | H | H | I | H | 0.47 | 4.93 | 10.5 | ****** |
| 25 | IndI-o-Me | Me | H | H | I | H | 1.38 | 9.64 | 7.0 | -- |
| 26 | IndI-o-I | I | H | H | I | H | 0.37 | 2.5 | 6.7 | *** |
| 27 | IndH-o-F$_2$ | F | H | F | H | H | 0.03 | 0.06 | 2.0 | n/a |
| 28 | IndH-o-Cl$_2$ | Cl | H | Cl | H | H | 0.088 | 0.82 | 9.3 | **** |
| 29 | Ind-vinyl-o-Br | Br | H | H | Vinyl | H | 0.54 | 8.04 | 14.9 | n/a |
| 30 | Ind-allyl-o-Br | Br | H | H | Allyl | H | 0.34 | 0.86 | 2.5 | n/a |
| 31 | Ind-CH$_2$OH | H | H | H | CH$_2$OH | H | 0.04 | 1.43 | 35.8 | n/a |
| 32 | IndCl-o-CH$_2$OH | CH$_2$OH | H | H | Cl | H | 0.13 | 2.34 | 18.0 | n/a |
| 33 | Ind-Thiolane | H | H | H | Thiolane | H | 0.03 | 0.31 | 10.3 | n/a |
| 34 | IndCl-o-Thiolane | Thiolane | H | H | Cl | H | 0.18 | 2.34 | 13.0 | n/a |
| 35 | Ind-Ph-p-OH | H | H | H | Ph-p-OH | H | 0.08 | 0.63 | 7.8 | n/a | a Relative value to 100% for $E_2$ by radiometric measurement.
b* The level of production of myelin basic protein (MBP), --- reduction of MBP.
c Two binding sites are observed.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

wherein:
$R^1$ and $R^3$ are independently hydrogen, halogen, $C_{1-4}$alkyl, $C_{2-4}$alkenyl, cyano, $C_{1-4}$haloalkyl, OH, —O$C_{1-4}$alkyl, —$C_{1-4}$alkylene-OH, or 1,3-dithiolan-2-yl;

$R^2$ is hydrogen, halogen, $C_{1-4}$alkyl, cyano, $C_{1-4}$haloalkyl, OH, or —O$C_{1-4}$alkyl; wherein at least one of $R^1$-$R^3$ is not hydrogen when $R^4$ is hydrogen, halogen, or $C_{1-4}$alkyl;

$R^4$ is hydrogen, halogen, $C_{1-4}$alkyl, $C_{2-4}$alkenyl, —$C_{1-4}$alkylene-OH, 1,3-dithiolan-2-yl, or phenyl optionally substituted with 1-5 substituents independently selected from the group consisting of halogen, $C_{1-4}$alkyl, cyano, $C_{1-4}$haloalkyl, OH, and —O$C_{1-4}$alkyl; and $R^5$ is hydrogen, halogen, or $C_{1-4}$alkyl;

provided that the compound is not
2-(3-chloro-4-hydroxyphenyl)-2H-indazol-5-ol; or
3-chloro-2-(3-chloro-4-hydroxyphenyl)-2H-indazol-5-ol.

Clause 2. The compound of clause 1, or a pharmaceutically acceptable salt thereof, wherein $R^1$ is halogen, $C_{1-4}$alkyl, $C_{2-4}$alkenyl, cyano, $C_{1-4}$haloalkyl, OH, —$C_{1-4}$alkylene-OH, or 1,3-dithiolan-2-yl.

Clause 3. The compound of clause 1 or 2, or a pharmaceutically acceptable salt thereof, wherein $R^1$ is $C_{2-4}$alkenyl, —$C_{1-4}$alkylene-OH, or 1,3-dithiolan-2-yl.

Clause 4. The compound of any of clauses 1-3, or a pharmaceutically acceptable salt thereof, wherein $R^4$ is hydrogen, halogen, $C_{1-4}$alkyl, $C_{2-4}$alkenyl, —$C_{1-4}$alkylene-OH, 1,3-dithiolan-2-yl, or phenyl optionally substituted with 1-5 substituents independently selected from the group consisting of halogen, $C_{1-4}$alkyl, cyano, $C_{1-4}$haloalkyl, OH, and —$OC_{1-4}$alkyl.

Clause 5. The compound of any of clauses 1-4, or a pharmaceutically acceptable salt thereof, wherein $R^4$ is $C_{2-4}$alkenyl, —$C_{1-4}$alkylene-OH, 1,3-dithiolan-2-yl, or phenyl optionally substituted with 1-5 substituents independently selected from the group consisting of halogen, $C_{1-4}$alkyl, cyano, $C_{1-4}$haloalkyl, OH, and —$OC_{1-4}$alkyl.

Clause 6. The compound of clause 1, or a pharmaceutically acceptable salt thereof, wherein:
$R^1$, $R^2$, and $R^3$ are independently hydrogen, halogen, $C_{1-4}$alkyl, cyano, $C_{1-4}$haloalkyl, OH, or —$OC_{1-4}$alkyl, wherein at least one of $R^1$-$R^3$ is not hydrogen; and
$R^4$ and $R^5$ are independently hydrogen, halogen, or $C_{1-4}$alkyl.

Clause 7. The compound of any of clauses 1-2 or 4-6, or a pharmaceutically acceptable salt thereof, wherein $R^1$ is halogen, $C_{1-4}$alkyl, cyano, $C_{1-4}$haloalkyl, OH, or —$OC_{1-4}$alkyl.

Clause 8. The compound of clause 7, or a pharmaceutically acceptable salt thereof, wherein $R^1$ is halogen, $C_{1-4}$alkyl, cyano, $C_{1-4}$haloalkyl, or OH.

Clause 9. The compound of clause 8, or a pharmaceutically acceptable salt thereof, wherein $R^1$ is chloro or methyl.

Clause 10. The compound of any of clauses 1-9, or a pharmaceutically acceptable salt thereof, wherein $R^2$ is hydrogen, halogen, or $C_{1-4}$alkyl.

Clause 11. The compound of clause 10, or a pharmaceutically acceptable salt thereof, wherein $R^2$ is hydrogen.

Clause 12. The compound of any of clauses 1-11, or a pharmaceutically acceptable salt thereof, wherein $R^3$ is hydrogen or halogen.

Clause 13. The compound of clause 12, or a pharmaceutically acceptable salt thereof, wherein $R^3$ is hydrogen.

Clause 14. The compound of any of clauses 1-13, or a pharmaceutically acceptable salt thereof, wherein $R^4$ is hydrogen or halogen.

Clause 15. The compound of clause 14, or a pharmaceutically acceptable salt thereof, wherein $R^4$ is halogen.

Clause 16. The compound of clause 15, or a pharmaceutically acceptable salt thereof, wherein $R^4$ is chloro.

Clause 17. The compound of any of clauses 1-16, or a pharmaceutically acceptable salt thereof, wherein $R^5$ is hydrogen or halogen.

Clause 18. The compound of clause 17, or a pharmaceutically acceptable salt thereof, wherein $R^5$ is hydrogen.

Clause 19. The compound of clause 1 selected from the group consisting of:
2-(2-bromo-4-hydroxyphenyl)-3-chloro-2H-indazol-5-ol;
3-chloro-2-(2-chloro-4-hydroxyphenyl)-2H-indazol-5-ol;
3-chloro-2-(4-hydroxy-2-methylphenyl)-2H-indazol-5-ol;
3-chloro-2-(4-hydroxy-2-iodophenyl)-2H-indazol-5-ol;
3-chloro-2-(2-fluoro-4-hydroxyphenyl)-2H-indazol-5-ol;
2-(3-chloro-5-hydroxy-2H-indazol-2-yl)-5-hydroxybenzonitrile;
3,4-dichloro-2-(2-chloro-4-hydroxyphenyl)-2H-indazol-5-ol;
3,4-dichloro-2-(2,6-difluoro-4-hydroxyphenyl)-2H-indazol-5-ol;
3,4-dichloro-2-(2,6-dichloro-4-hydroxyphenyl)-2H-indazol-5-ol;
3-chloro-2-(4-hydroxy-2-(trifluoromethyl)phenyl)-2H-indazol-5-ol;
4-(3-chloro-5-hydroxy-2H-indazol-2-yl)benzene-1,3-diol;
3-chloro-2-(3-fluoro-4-hydroxyphenyl)-2H-indazol-5-ol;
3-chloro-2-(4-hydroxy-3-methylphenyl)-2H-indazol-5-ol;
2-(2-bromo-4-hydroxyphenyl)-3-fluoro-2H-indazol-5-ol;
2-(2-chloro-4-hydroxyphenyl)-3-fluoro-2H-indazol-5-ol;
3-fluoro-2-(4-hydroxy-2-methylphenyl)-2H-indazol-5-ol;
3-fluoro-2-(4-hydroxy-2-iodophenyl)-2H-indazol-5-ol;
3-bromo-2-(2-bromo-4-hydroxyphenyl)-2H-indazol-5-ol;
3-bromo-2-(2-chloro-4-hydroxyphenyl)-2H-indazol-5-ol;
3-bromo-2-(4-hydroxy-2-methylphenyl)-2H-indazol-5-ol;
3-bromo-2-(4-hydroxy-2-iodophenyl)-2H-indazol-5-ol;
2-(2-bromo-4-hydroxyphenyl)-3-iodo-2H-indazol-5-ol;
2-(2-chloro-4-hydroxyphenyl)-3-iodo-2H-indazol-5-ol;
2-(4-hydroxy-2-methylphenyl)-3-iodo-2H-indazol-5-ol;
2-(4-hydroxy-2-iodophenyl)-3-iodo-2H-indazol-5-ol;
2-(2,6-difluoro-4-hydroxyphenyl)-2H-indazol-5-ol;
2-(2,6-dichloro-4-hydroxyphenyl)-2H-indazol-5-ol;
2-(2-bromo-4-hydroxyphenyl)-3-vinyl-2H-indazol-5-ol;
3-allyl-2-(2-bromo-4-hydroxyphenyl)-2H-indazol-5-ol;
3-allyl-2-(4-hydroxy-2-vinylphenyl)-2H-indazol-5-ol;
3-(hydroxymethyl)-2-(4-hydroxyphenyl)-2H-indazol-5-ol;
3-chloro-2-(4-hydroxy-2-(hydroxymethyl)phenyl)-2H-indazol-5-ol;
3-(1,3-dithiolan-2-yl)-2-(4-hydroxyphenyl)-2H-indazol-5-ol;
2-(2-(1,3-dithiolan-2-yl)-4-hydroxyphenyl)-3-chloro-2H-indazol-5-ol; and
4,4'-(5-hydroxy-2H-indazole-2,3-diyl)diphenol,
or a pharmaceutically acceptable salt thereof.

Clause 20. A pharmaceutical composition comprising the compound of any of clauses 1-19, or a pharmaceutically acceptable salt thereof, and a pharmaceutically acceptable carrier.

Clause 21. A method of treating a demyelinating disease comprising administering, to a subject in need thereof, a therapeutically effective amount of the compound of any of clauses 1-19, or a pharmaceutically acceptable salt thereof, or the pharmaceutical composition of clause 20.

Clause 22. The method of clause 21, wherein the demyelinating disease is multiple sclerosis.

Clause 23. The method of clause 22, wherein the multiple sclerosis is primary progressive multiple sclerosis, relapsing-remitting multiple sclerosis, secondary progressive multiple sclerosis, or progressive relapsing multiple sclerosis.

Clause 24. A method of promoting remyelination of demyelinated axons comprising administering to a subject in need thereof a therapeutically effective amount of the compound of any of clauses 1-19, or a pharmaceutically acceptable salt thereof, or the pharmaceutical composition of clause 20.

Clause 25. A method of differentiating oligodendrocyte progenitor cells comprising administering to a subject in need thereof a therapeutically effective amount of the compound of any of clauses 1-19, or a pharmaceutically acceptable salt thereof, or the pharmaceutical composition of clause 20.

Clause 26. A method of treating endometriosis comprising administering, to a subject in need thereof, a therapeutically effective amount of the compound of any of clauses 1-19, or a pharmaceutically acceptable salt thereof, or the pharmaceutical composition of clause 20.

Clause 27. The compound of any of clauses 1-19, or a pharmaceutically acceptable salt thereof, or the pharmaceutical composition of clause 20 for use in the treatment of a demyelinating disease, or in the promotion of remyelination of demyelinated axons, or in the differentiation of oligodendrocyte progenitor cells, or in the treatment of endometriosis.

Clause 28. The use of the compound of any of clauses 1-19, or a pharmaceutically acceptable salt thereof, or the pharmaceutical composition of clause 20 in the manufacture of a medicament for the treatment of a demyelinating disease, or for the promotion of remyelination of demyelinated axons, or for the differentiation of oligodendrocyte progenitor cells, or for the treatment of endometriosis.

Clause 29. A kit comprising the compound of any of clauses 1-19, or a pharmaceutically acceptable salt thereof, or the pharmaceutical composition of clause 20, and instructions for use thereof.

REFERENCES

Banks E, Canfell K (2009) Invited Commentary: Hormone therapy risks and benefits—The Women's Health Initiative findings and the postmenopausal estrogen timing hypothesis. Am J Epidemiol 170:24-28.

Barun B, Bar-Or A (2012) Treatment of multiple sclerosis with anti-CD20 antibodies. Clin Immunol 142:31-37.

Beringer A, Noack M, Miossec P (2016) IL-17 in Chronic Inflammation: From Discovery to Targeting. Trends Mol Med 22:230-241.

Burns K A, Korach K S (2012) Estrogen receptors and human disease: an update. Arch Toxicol 86:1491-1504.

Crawford D K, Mangiardi M, Tiwari-Woodruff S K (2009a) Assaying the functional effects of demyelination and remyelination: revisiting field potential recordings. J Neurosci Methods 182:25-33.

Crawford D K, Mangiardi M, Xia X, López-Valdés H E, Tiwari-Woodruff S K (2009b) Functional recovery of callosal axons following demyelination: a critical window. Neuroscience 164:1407-1421.

Crawford D K, Mangiardi M, Song B, Patel R, Du S, Sofroniew M V, Voskuhl R R, Tiwari-Woodruff S K (2010) Oestrogen receptor beta ligand: a novel treatment to enhance endogenous functional remyelination. Brain 133:2999-3016.

Cua D J, Hinton D R, Stohlman S A (1995) Self-antigen-induced Th2 responses in experimental allergic encephalomyelitis (EAE)-resistant mice. Th2-mediated suppression of autoimmune disease. J Immunol 155:4052-4059.

De Angelis M, Stossi F, Carlson K A, Katzenellenbogen B S, Katzenellenbogen J A (2005) Indazole Estrogens: Highly Selective Ligands for the Estrogen Receptor. Journal of Medicinal Chemistry 48:1132-1144.

De Filippo K, Henderson R B, Laschinger M, Hogg N (2008) Neutrophil chemokines KC and macrophage-inflammatory protein-2 are newly synthesized by tissue macrophages using distinct TLR signaling pathways. Journal of Immunology 180:4308-4315.

de Waal Malefyt R, Figdor C G, Huijbens R, Mohan-Peterson S, Bennett B, Culpepper J, Dang W, Zurawski G, de Vries J E (1993) Effects of IL-13 on phenotype, cytokine production, and cytotoxic function of human monocytes. Comparison with IL-4 and modulation by IFN-gamma or IL-10. J Immunol 151:6370-6381.

Denic A, Johnson A J, Bieber A J, Warrington A E, Rodriguez M, Pirko I (2011) The relevance of animal models in multiple sclerosis research. Pathophysiology 18:21-29.

Du S, Sandoval F, Trinh P, Umeda E, Voskuhl R (2011) Estrogen receptor-beta ligand treatment modulates dendritic cells in the target organ during autoimmune demyelinating disease. Eur J Immunol 41:140-150.

Filipovic R, Zecevic N (2008) The effect of CXCL1 on human fetal oligodendrocyte progenitor cells. Glia 56:1-15.

Fletcher J M, Lalor S J, Sweeney C M, Tubridy N, Mills K H (2010) T cells in multiple sclerosis and experimental autoimmune encephalomyelitis. Clin Exp Immunol 162:1-11.

Hasselmann J P C, Karim H, Khalaj A J, Ghosh S, Tiwari-Woodruff S K (2017) Consistent induction of chronic experimental autoimmune encephalomyelitis in C57BL/6 mice for the longitudinal study of pathology and repair. J Neurosci Methods 284:71-84.

Hewitt S C, Korach K S (2003) Oestrogen receptor knockout mice: roles for oestrogen receptors alpha and beta in reproductive tissues. Reproduction 125:143-149.

Inoue M, Chen P H, Siecinski S, Li Q J, Liu C, Steinman L, Gregory S G, Benner E, Shinohara M L (2016) An interferon-beta-resistant and NLRP3 inflammasome-independent subtype of EAE with neuronal damage. Nat Neurosci 19:1599-1609.

Jansson L, Holmdahl R (1998) Estrogen-mediated immunosuppression in autoimmune diseases. Inflamm Res 47:290-301.

Khalaj A J (2016) Nudging oligodendrocyte intrinsic signaling to remyelinate and repair: Estrogen receptor ligand effects. 160:43-52.

Khalaj A J, Yoon J, Nakai J, Winchester Z, Moore S M, Yoo T, Martinez-Torres L, Kumar S, Itoh N, Tiwari-Woodruff S K (2013) Estrogen receptor (ER) beta expression in oligodendrocytes is required for attenuation of clinical disease by an ERbeta ligand. Proc Natl Acad Sci USA 110:19125-19130.

Kim S, Liva S M, Dalal M A, Verity M A, Voskuhl R R (1999) Estriol ameliorates autoimmune demyelinating disease: implications for multiple sclerosis. Neurology 52:1230-1238.

Kumar S, Patel R, Moore S, Crawford D K, Suwanna N, Mangiardi M, Tiwari-Woodruff S K (2013) Estrogen receptor beta ligand therapy activates PI3K/Akt/mTOR signaling in oligodendrocytes and promotes remyelination in a mouse model of multiple sclerosis. Neurobiol Dis 56:131-144.

Lauderdale K, Murphy T, Tung T, Davila D, Binder D K, Fiacco T A (2015) Osmotic Edema Rapidly Increases Neuronal Excitability Through Activation of NMDA Receptor-Dependent Slow Inward Currents in Juvenile and Adult Hippocampus. ASN Neuro 7.

Luchtman D W, Ellwardt E, Larochelle C, Zipp F (2014) IL-17 and related cytokines involved in the pathology and immunotherapy of multiple sclerosis: Current and future developments. Cytokine Growth Factor Rev 25:403-413.

Mangiardi M, Crawford D K, Xia X, Du S, Simon-Freeman R, Voskuhl R R, Tiwari-Woodruff S K (2011) An animal model of cortical and callosal pathology in multiple sclerosis. Brain Pathol 21:263-278.

Minutolo F, Macchia M, Katzenellenbogen B S, Katzenellenbogen J A (2011) Estrogen receptor beta ligands: recent advances and biomedical applications. Med Res Rev 31:364-442.

Monnerie H, Romer M, Jensen B K, Millar J S, Jordan-Sciutto K L, Kim S F, Grinspan J B (2017) Reduced sterol regulatory element-binding protein (SREBP) processing through site-1 protease (SiP) inhibition alters oligodendrocyte differentiation in vitro. J Neurochem 140:53-67.

Moore S, Khalaj A J, Yoon J, Patel R, Hannsun G, Yoo T, Sasidhar M, Martinez-Torres L, Hayardeny L, Tiwari-Woodruff S K (2013) Therapeutic laquinimod treatment decreases inflammation, initiates axon remyelination, and improves motor deficit in a mouse model of multiple sclerosis. Brain Behav 3:664-682.

Moore S M, Khalaj A J, Kumar S, Winchester Z, Yoon J, Yoo T, Martinez-Torres L, Yasui N, Katzenellenbogen J A, Tiwari-Woodruff S K (2014) Multiple functional therapeutic effects of the estrogen receptor beta agonist indazole-Cl in a mouse model of multiple sclerosis. Proc Natl Acad Sci USA 111:18061-18066.

Moss R B, Moll T, El-Kalay M, Kohne C, Soo Hoo W, Encinas J, Carlo D J (2004) Th1/Th2 cells in inflammatory disease states: therapeutic implications. Expert Opin Biol Ther 4:1887-1896. Nicot A (2009) Gender and sex hormones in multiple sclerosis pathology and therapy. Front Biosci 14:4477-4515.

Omari K M, John G, Lango R, Raine C S (2006) Role for CXCR2 and CXCL1 on glia in multiple sclerosis. Glia 53:24-31.

Omari K M, Lutz S E, Santambrogio L, Lira S A, Raine C S (2009) Neuroprotection and remyelination after autoimmune demyelination in mice that inducibly overexpress CXCL1. Am J Pathol 174:164-176.

Ouyang W, Rutz S, Crellin N K, Valdez P A, Hymowitz S G (2011) Regulation and functions of the IL-10 family of cytokines in inflammation and disease. Annu Rev Immunol 29:71-109.

Ozturk A, Smith S A, Gordon-Lipkin E M, Harrison D M, Shiee N, Pham D L, Caffo B S, Calabresi P A, Reich D S (2010) MRI of the corpus callosum in multiple sclerosis: association with disability. Mult Scler 16:166-177.

Paterni I, Granchi C, Katzenellenbogen J A, Minutolo F (2014) Estrogen receptors alpha (ERalpha) and beta (ERbeta): subtype-selective ligands and clinical potential. Steroids 90:13-29.

Pettinelli C B, McFarlin D E (1981) Adoptive transfer of experimental allergic encephalomyelitis in SJL/J mice after in vitro activation of lymph node cells by myelin basic protein: requirement for Lyt 1+2-T lymphocytes. Journal of immunology 127:1420-1423.

Popko B, Baerwald K D (1999) Oligodendroglial response to the immune cytokine interferon gamma. Neurochem Res 24:331-338.

Preston R J, Waxman S G, Kocsis J D (1983) Effects of 4-aminopyridine on rapidly and slowly conducting axons of rat corpus callosum. Exp Neurol 79:808-820.

Robinson S, Tani M, Strieter R M, Ransohoff R M, Miller R H (1998) The chemokine growth-regulated oncogene-alpha promotes spinal cord oligodendrocyte precursor proliferation. J Neurosci 18:10457-10463.

Rossi S, Mancino R, Bergami A, Mori F, Castelli M, De Chiara V, Studer V, Mataluni G, Sancesario G, Parisi V, Kusayanagi H, Bernardi G, Nucci C, Bernardini S, Martino G, Furlan R, Centonze D (2011) Potential role of IL-13 in neuroprotection and cortical excitability regulation in multiple sclerosis. Mult Scler 17:1301-1312.

Saijo K, Collier J G, Li A C, Katzenellenbogen J A, Glass C K (2011) An ADIOL-ERbeta-CtBP transrepression pathway negatively regulates microglia-mediated inflammation. Cell 145:584-595.

Sinha S, Kaler L J, Proctor T M, Teuscher C, Vandenbark A A, Offner H (2008) IL-13-mediated gender difference in susceptibility to autoimmune encephalomyelitis. J Immunol 180:2679-2685.

Sospedra M, Martin R (2005) Immunology of multiple sclerosis. Annu Rev Immunol 23:683-747.

Tirotta E, Ransohoff R M, Lane T E (2011) CXCR2 signaling protects oligodendrocyte progenitor cells from IFN-gamma/CXCL10-mediated apoptosis. Glia 59:1518-1528.

Tiwari-Woodruff S, Crawford D, Song B, Sofroniew M, Mangiardi M (2009) A critical window: functional recovery of callosal axons following demyelination. JOURNAL OF NEUROCHEMISTRY 108:65-66.

Tiwari-Woodruff S, Beltran-Parrazal L, Charles A, Keck T, Vu T, Bronstein J (2006a) K+ channel KV3.1 associates with OSP/claudin-11 and regulates oligodendrocyte development. Am J Physiol Cell Physiol 291:C687-698.

Tiwari-Woodruff S, Morales L, Loo K, Liu H, Peterson C, Voskuhl R (2006b) Treatment with an estrogen receptor a ligand is both anti-inflammatory and neuroprotective in experimental autoimmune encephalomyelitis. JOURNAL OF NEUROCHEMISTRY 96:23-23.

Tiwari-Woodruff S K, Morales L-B J, Lee R, Voskuhl R (2007) Differential effects of estrogen receptor (ER) alpha versus ER beta ligand treatment: Anti-inflammatory versus directly neuroprotective. NEUROLOGY 68:A316-A316.

Tiwari-Woodruff S K, Buznikov A G, Vu T Q, Micevych P E, Chen K, Kornblum H I, Bronstein J M (2001) OSP/claudin-11 forms a complex with a novel member of the tetraspanin super family and beta1 integrin and regulates proliferation and migration of oligodendrocytes. J Cell Biol 153:295-305.

Tsai H H, Frost E, To V, Robinson S, Ffrench-Constant C, Geertman R, Ransohoff R M, Miller R H (2002) The chemokine receptor CXCR2 controls positioning of oligodendrocyte precursors in developing spinal cord by arresting their migration. Cell 110:373-383.

Vartanian T, Li Y, Zhao M, Stefansson K (1995) Interferon-gamma-induced oligodendrocyte cell death: implications for the pathogenesis of multiple sclerosis. Mol Med 1:732-743.

Xue B, Zhang Z, Beltz T G, Guo F, Hay M, Johnson A K (2014) Estrogen regulation of the brain renin-angiotensin system in protection against angiotensin II-induced sensitization of hypertension. Am J Physiol Heart Circ Physiol 307:H191-198.

Zhao Y, Gong P, Chen Y, Nwachukwu J C, Srinivasan S, Ko C, Bagchi M K, Taylor R N, Korach K S, Nettles K W, Katzenellenbogen J A, Katzenellenbogen B S (2015) Dual suppression of estrogenic and inflammatory activities for targeting of endometriosis. Sci Transl Med 7:271ra279.

Zorzella-Pezavento S F, Chiuso-Minicucci F, Franca T G, Ishikawa L L, da Rosa L C, Marques C, Ikoma M R, Sartori A (2013) Persistent inflammation in the CNS during chronic EAE despite local absence of IL-17 production. Mediators Inflamm 2013:519627.

We claim:
1. A compound of formula (I), or a pharmaceutically acceptable salt thereof,

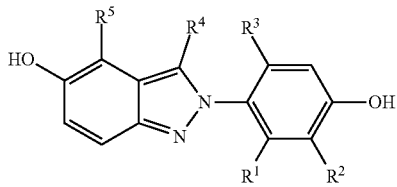

wherein:
R$^1$ is halogen, C$_{1-4}$alkyl, C$_{2-4}$alkenyl, cyano, C$_{1-4}$haloalkyl, OH, —OC$_{1-4}$alkyl, —C$_{1-4}$alkylene-OH, or 1,3-dithiolan-2-yl;
R$^2$ is hydrogen, halogen, C$_{1-4}$alkyl, cyano, C$_{1-4}$haloalkyl, OH, or —OC$_{1-4}$alkyl;
R$^3$ is hydrogen, halogen, C$_{1-4}$alkyl, C$_{2-4}$alkenyl, cyano, C$_{1-4}$haloalkyl, OH, —OC$_{1-4}$alkyl, —C$_{1-4}$alkylene-OH, or 1,3-dithiolan-2-yl;
R$^4$ is halogen; and
R$^5$ is hydrogen, halogen, or C$_{1-4}$alkyl.

2. The compound of claim 1, or a pharmaceutically acceptable salt thereof, wherein R$^1$ is halogen, C$_{1-4}$alkyl, C$_{2-4}$alkenyl, cyano, C$_{1-4}$haloalkyl, OH, —C$_{1-4}$alkylene-OH, or 1,3-dithiolan-2-yl.

3. The compound of claim 2, or a pharmaceutically acceptable salt thereof, wherein R$^1$ is C$_{2-4}$alkenyl, —C$_{1-4}$alkylene-OH, or 1,3-dithiolan-2-yl.

4. The compound of claim 2, or a pharmaceutically acceptable salt thereof, wherein R$^1$ is halogen, C$_{1-4}$alkyl, cyano, C$_{1-4}$haloalkyl, or OH.

5. The compound of claim 2, or a pharmaceutically acceptable salt thereof, wherein R$^1$ is halogen or C$_{1-4}$alkyl.

6. The compound of claim 2, or a pharmaceutically acceptable salt thereof, wherein R$^1$ is chloro or methyl.

7. The compound of claim 6, or a pharmaceutically acceptable salt thereof, wherein R$^4$ is chloro.

8. The compound of claim 5, or a pharmaceutically acceptable salt thereof, wherein R$^1$ is hydrogen, halogen, or C$_{1-4}$alkyl.

9. The compound of claim 7, or a pharmaceutically acceptable salt thereof, wherein R$^2$ is hydrogen.

10. The compound of claim 5, or a pharmaceutically acceptable salt thereof, wherein R$^3$ is hydrogen, halogen, or C$_{1-4}$alkyl.

11. The compound of claim 7, or a pharmaceutically acceptable salt thereof, wherein R$^3$ is hydrogen.

12. The compound of claim 9, or a pharmaceutically acceptable salt thereof, wherein R$^3$ is hydrogen.

13. The compound of claim 5, or a pharmaceutically acceptable salt thereof, wherein R$^5$ is hydrogen or halogen.

14. The compound of claim 7, or a pharmaceutically acceptable salt thereof, wherein R$^5$ is hydrogen.

15. The compound of claim 12, or a pharmaceutically acceptable salt thereof, wherein R$^5$ is hydrogen.

16. The compound of claim 1 selected from the group consisting of:
2-(2-bromo-4-hydroxyphenyl)-3-chloro-2H-indazol-5-ol;
3-chloro-2-(2-chloro-4-hydroxyphenyl)-2H-indazol-5-ol;
3-chloro-2-(4-hydroxy-2-methylphenyl)-2H-indazol-5-ol;
3-chloro-2-(4-hydroxy-2-iodophenyl)-2H-indazol-5-ol;
3-chloro-2-(2-fluoro-4-hydroxyphenyl)-2H-indazol-5-ol;
2-(3-chloro-5-hydroxy-2H-indazol-2-yl)-5-hydroxybenzonitrile;
3,4-dichloro-2-(2-chloro-4-hydroxyphenyl)-2H-indazol-5-ol;
3,4-dichloro-2-(2,6-difluoro-4-hydroxyphenyl)-2H-indazol-5-ol;
3,4-dichloro-2-(2,6-dichloro-4-hydroxyphenyl)-2H-indazol-5-ol;
3-chloro-2-(4-hydroxy-2-(trifluoromethyl)phenyl)-2H-indazol-5-ol;
4-(3-chloro-5-hydroxy-2H-indazol-2-yl)benzene-1,3-diol;
2-(2-bromo-4-hydroxyphenyl)-3-fluoro-2H-indazol-5-ol;
2-(2-chloro-4-hydroxyphenyl)-3-fluoro-2H-indazol-5-ol;
3-fluoro-2-(4-hydroxy-2-methylphenyl)-2H-indazol-5-ol;
3-fluoro-2-(4-hydroxy-2-iodophenyl)-2H-indazol-5-ol;
3-bromo-2-(2-bromo-4-hydroxyphenyl)-2H-indazol-5-ol;
3-bromo-2-(2-chloro-4-hydroxyphenyl)-2H-indazol-5-ol;
3-bromo-2-(4-hydroxy-2-methylphenyl)-2H-indazol-5-ol;
3-bromo-2-(4-hydroxy-2-iodophenyl)-2H-indazol-5-ol;
2-(2-bromo-4-hydroxyphenyl)-3-iodo-2H-indazol-5-ol;
2-(2-chloro-4-hydroxyphenyl)-3-iodo-2H-indazol-5-ol;
2-(4-hydroxy-2-methylphenyl)-3-iodo-2H-indazol-5-ol;
2-(4-hydroxy-2-iodophenyl)-3-iodo-2H-indazol-5-ol;
3-chloro-2-(4-hydroxy-2-(hydroxymethyl)phenyl)-2H-indazol-5-ol; and
2-(2-(1,3-dithiolan-2-yl)-4-hydroxyphenyl)-3-chloro-2H-indazol-5-ol; and
or a pharmaceutically acceptable salt thereof.

17. A pharmaceutical composition comprising the compound of claim 1, or a pharmaceutically acceptable salt thereof, and a pharmaceutically acceptable carrier.

18. A method of treating a demyelinating disease comprising administering, to a subject in need thereof, a therapeutically effective amount of the compound of claim 1, or a pharmaceutically acceptable salt thereof.

19. The method of claim 18, wherein the demyelinating disease is multiple sclerosis.

20. The method of claim 19, wherein the multiple sclerosis is primary progressive multiple sclerosis, relapsing-remitting multiple sclerosis, secondary progressive multiple sclerosis, or progressive relapsing multiple sclerosis.

21. A method of promoting remyelination of demyelinated axons comprising administering to a subject in need thereof a therapeutically effective amount of the compound of claim 1, or a pharmaceutically acceptable salt thereof.

22. A method of differentiating oligodendrocyte progenitor cells comprising administering to a subject in need thereof a therapeutically effective amount of the compound of claim 1, or a pharmaceutically acceptable salt thereof.

23. A method of treating endometriosis comprising administering, to a subject in need thereof, a therapeutically effective amount of the compound of claim 1, or a pharmaceutically acceptable salt thereof.

24. A kit comprising the compound of claim 1, or a pharmaceutically acceptable salt thereof, and instructions for use thereof.

25. The compound of claim 16, or a pharmaceutically acceptable salt thereof, wherein the compound is 3-chloro-2-(4-hydroxy-2-methylphenyl)-2H-indazol-5-ol.

26. The compound of claim 16, or a pharmaceutically acceptable salt thereof, wherein the compound is 3-chloro-2-(2-chloro-4-hydroxyphenyl)-2H-indazol-5-ol.

27. The compound of claim 16, or a pharmaceutically acceptable salt thereof, wherein the compound is 4-(3-chloro-5-hydroxy-2H-indazol-2-yl)benzene-1,3-diol.

\* \* \* \* \*